(12) United States Patent
Schofield et al.

(10) Patent No.: US 11,560,424 B2
(45) Date of Patent: Jan. 24, 2023

(54) ANTIBODIES TO ALPHA-SYNUCLEIN AND USES THEREOF

(71) Applicant: MedImmune Limited, Cambridge (GB)

(72) Inventors: Darren Schofield, Cambridge (GB); Michael Perkinton, Cambridge (GB); Lorraine Irving, Cambridge (GB); George Thom, Cambridge (GB)

(73) Assignee: MEDIMMUNE LIMITED, Cambridge (GB)

(*) Notice: Subject to any disclaimer, the term of this patent is extended or adjusted under 35 U.S.C. 154(b) by 127 days.

(21) Appl. No.: 17/111,159

(22) Filed: Dec. 3, 2020

(65) Prior Publication Data

US 2021/0179698 A1 Jun. 17, 2021

Related U.S. Application Data

(63) Continuation of application No. 16/170,468, filed on Oct. 25, 2018, now Pat. No. 10,889,639, which is a (Continued)

(51) Int. Cl.
*A61K 45/00* (2006.01)
*G01N 33/567* (2006.01)
(Continued)

(52) U.S. Cl.
CPC .......... *C07K 16/18* (2013.01); *G01N 33/537* (2013.01); *G01N 33/543* (2013.01); *G01N 33/577* (2013.01); *G01N 33/6896* (2013.01); *A61K 2039/505* (2013.01); *C07K 2317/21* (2013.01); *C07K 2317/24* (2013.01);
(Continued)

(58) Field of Classification Search
None
See application file for complete search history.

(56) References Cited

U.S. PATENT DOCUMENTS 7,727,957 B2 6/2010 Schenk et al.
7,919,088 B2 4/2011 Schenk et al.
(Continued)

FOREIGN PATENT DOCUMENTS

CN 102869680 A 1/2013
CN 105121473 A 12/2015
(Continued)

OTHER PUBLICATIONS

Brys et al., "Randomized Phase I Clinical Trial of Anti-alpha-Synuclein Antibody BIIB054," Movement Disorders, vol. 34(8): 1154-1163 (2019).
(Continued)

*Primary Examiner* — Aurora M Fontainhas
(74) *Attorney, Agent, or Firm* — White & Case LLP

(57) ABSTRACT

The invention provides antibodies that specifically bind human α-synuclein with a high affinity and reduces α-synuclein spreading in vivo, recombinant polypeptides comprising said antibodies or antigen-binding fragment thereof and methods for generating such polypeptides, as well as compositions and methods for generating α-synuclein antibodies, and methods of using α-synuclein antibodies for the treatment of diseases of the central nervous system, in particular alpha-synucleinopathies.

Figure 1:
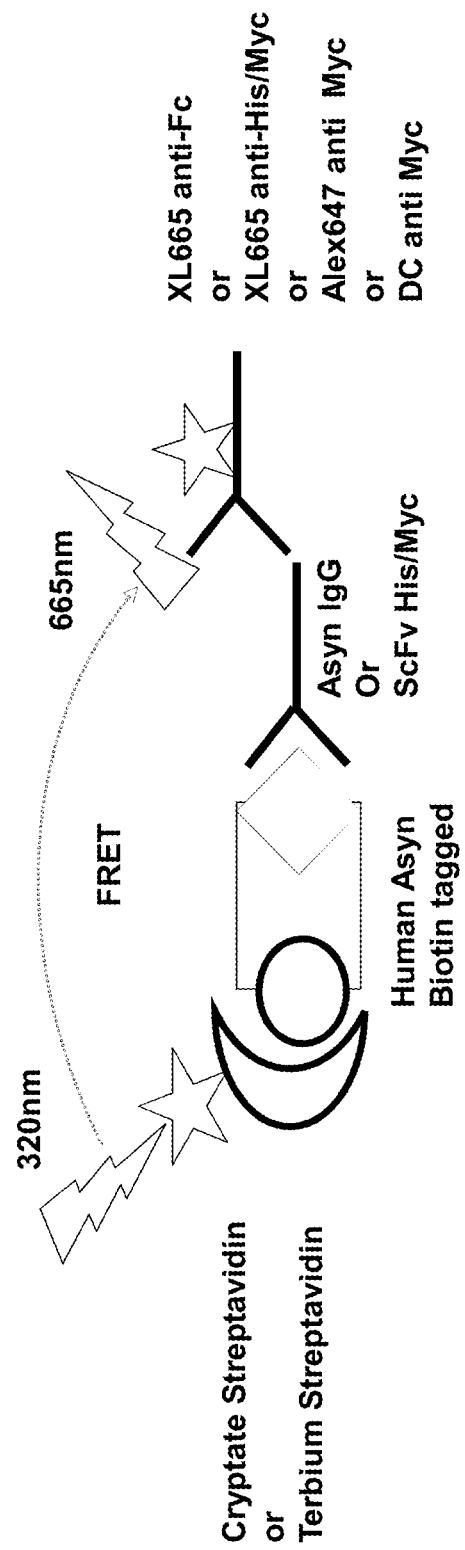

35 Claims, 23 Drawing Sheets
Specification includes a Sequence Listing.

Related U.S. Application Data continuation of application No. 15/611,416, filed on Jun. 1, 2017, now Pat. No. 10,160,800.

(60) Provisional application No. 62/344,746, filed on Jun. 2, 2016.

(51) Int. Cl.

| | |
|---|---|
| *C07K 16/18* | (2006.01) |
| *G01N 33/537* | (2006.01) |
| *G01N 33/543* | (2006.01) |
| *G01N 33/577* | (2006.01) |
| *G01N 33/68* | (2006.01) |
| *A61K 39/00* | (2006.01) |

(52) U.S. Cl.
CPC ...... *C07K 2317/31* (2013.01); *C07K 2317/33* (2013.01); *C07K 2317/524* (2013.01); *C07K 2317/565* (2013.01); *C07K 2317/622* (2013.01); *C07K 2317/71* (2013.01); *C07K 2317/92* (2013.01)

(56) References Cited

U.S. PATENT DOCUMENTS

| | | | |
|---|---|---|---|
| 7,943,129 | B2 | 5/2011 | Muruganandam et al. |
| 8,092,801 | B2 | 1/2012 | Schenk et al. |
| 8,809,506 | B2 | 8/2014 | Lannfelt et al. |
| 8,968,734 | B2 | 3/2015 | Nordstrom et al. |
| 9,034,337 | B2 | 5/2015 | Schenk et al. |
| 9,315,569 | B2 | 4/2016 | Lannfelt et al. |
| 9,580,493 | B2 | 2/2017 | Weihofen et al. |
| 9,605,056 | B2 | 3/2017 | Barbour et al. |
| 2008/0175838 | A1 | 7/2008 | Schenk et al. |
| 2009/0047300 | A1 | 2/2009 | Abulrob et al. |
| 2009/0208487 | A1 | 8/2009 | Schenk et al. |
| 2012/0156222 | A1 | 6/2012 | Lannfelt |
| 2013/0072663 | A1 | 3/2013 | Chilcote et al. |
| 2016/0060331 | A1 | 3/2016 | Schenk et al. |
| 2016/0194407 | A1 | 7/2016 | Hay et al. |
| 2016/0244515 | A1 | 8/2016 | Weihofen et al. |
| 2017/0152310 | A1 | 6/2017 | Barbour et al. |

FOREIGN PATENT DOCUMENTS

| | | |
|---|---|---|
| JP | 2010-526028 A | 7/2010 |
| JP | 2013-525266 | 6/2013 |
| JP | 2016-511254 A | 4/2016 |
| WO | WO-2005013889 A2 | 2/2005 |
| WO | WO-2005047860 A2 | 5/2005 |
| WO | WO-2006020581 A2 | 2/2006 |
| WO | WO-2007012061 A2 | 1/2007 |
| WO | WO-2008103472 A2 | 8/2008 |
| WO | WO-2008/108472 A1 | 9/2008 |
| WO | WO-2011/104898 A1 | 9/2011 |
| WO | WO-2011104696 A1 | 9/2011 |
| WO | WO-2013063516 A1 | 5/2013 |
| WO | WO-2014058924 A2 | 4/2014 |
| WO | WO-2014132210 A1 | 9/2014 |
| WO | WO-2015075011 A | 5/2015 |

OTHER PUBLICATIONS

Jankovic et al., "Safety and Tolerability of Multiple Ascending Doses of PRX002/RG7935, and Anti-alpha-Synuclein Monoclonal Antibody in Patients with Parkinson Disease A Randomized Clinical Trial," vol. 75(10): 1206-1214 (2018).
First Office Action; Chinese Patent Application No. 201780045951.2; 4 pages; dated Dec. 29, 2021.
Search Report for Chinese Patent Application No. 201780045951.2, 2 pages. dated Nov. 23, 2021.
Angot et al., "Dissecting the potential molecular mechanisms underlying α-synuclein cell-to-cell transfer in Parkinson's disease," Parkinsonism and Related Disorders, vol. 15S3: S143-S147 (2009).
Bae et al., "Antibody-Aided Clearance of Extracellular α-Synuclein Prevents Cell-to-Cell Aggregate Transmission," The Journal of Neuroscience, vol. 32(39): 13454-13469 (2012).
Bartels et al., "The N-Terminus of the Intrinsically Disordered Protein α-Synuclein Triggers Membrane Binding and Helix Folding," Biophysical Journal, vol. 99: 2116-2124 (2010).
Bisaglia et al., "Structural insights on physiological functions and pathological effects of α-synuclein," The FASEB Journal, vol. 23: 329-340 (2009).
Boado et al., "Pharmacokinetics and Brain Uptake of a Genetically Engineered Bi-functional Fusion Antibody Targeting the Mouse Transferrin Receptor," Molecular Pharmacology, vol. 7(1): 237-244 (2010).
Brightman et al., "Junctions between intimately apposed cell membranes in the vertebrate brain," The Journal of Cell Biology, vol. 40: 648-677 (1969).
Cremades et al., "Direct Observation of the Interconversion of Normal and Toxic Forms of α-Synuclein," Cell, vol. 149: 1048-1059 (2012).
Danzer et al., "Different Species of α-Synuclein Oligomers Induce Calcium Influx and Seeding," The Journal of Neuroscience, vol. 27(34): 9220-9232 (2007).
Desplats et al., "Inclusion formation and neuronal cell death through neuron-to-neuron transmission of α-synuclein," Proceedings of the National Academy of Sciences, vol. 106(31):13010-13015 (2009).
Emmanouilidou et al., "Assessment of α-Synuclein Secretion in Mouse and Human Brain Parenchyma," PLoS ONE, vol. 6(7), e22225: 1-9 (2011).
Fortin et al., "Neural Activity Controls the Synaptic Accumulation of α-Synuclein," The Journal of Neuroscience, vol. 25(47): 10913-10921 (2005).
Gaillard et al., "Pharmacological investigations on lipopolysaccharide-induced permeability changes in the blood-brain barrier in vitro," Microvascular Research, vol. 65: 24-31 (2003).
Games et al., "Reducing C-Terminal-Truncated Alpha-Synuclein by Immunotherapy Attenuates Neurodegeneration and Propagation in Parkinson's Disease-Like Models," The Journal of Neuroscience, vol. 34(28): 9441-9454 (2014).
Iwai et al., "The Precursor Protein of Non-Aβ Component of Alzheimer's Disease Amyloid Is a Presynaptic Protein of the Central Nervous System," Neuron, vol. 14: 467-475 (1995).
Jellinger K., "Neuropathological Spectrum of Synucleinopathies," Movement Disorders, vol. 18(Suppl. 6): S2-S12 (2003).
Kalia et al., "Parkinson's disease," Lancet, vol. 386: 896-912 (2015).
Kordower et al., "Lewy body-like pathology in long-term embryonic nigral transplants in Parkinson's disease," Nature Medicine, vol. 14(5): 504-506 (2008).
Lashuel et al., "Amyloid pores from pathogenic mutations," Nature, vol. 418: 291 (2002).
Lawand, et al., "Targeting α-synuclein as a therapeutic strategy for Parkinson's disease," Expert Opin. Ther. Targets 19(10) 1351-1360 (2015).
Lee et al., "Cell-to-cell transmission of non-prion protein aggregates," Nature Reviews Neurol., vol. 6:702-706 (2010).
Lee et al., "Direct Transfer of α-Synuclein from Neuron to Astroglia Causes Inflammatory Responses in Synucleinopathies," The Journal of Biological Chemistry, vol. 285(12): 9262-9272 (2010).
Lee, J.S. et al., "Mechanism of Anti-[alpha]-Synuclein Immunotherapy," Journal of Movement Disorders, vol. 9(1): 14-19 (2016).
Li et al., "Lewy bodies in grafted neurons in subjects with Parkinson's disease suggest host-to-graft disease propagation," Nature Medicine, vol. 14(5): 501-503 (2008).
Luk et al., "Exogenous α-synuclein fibrils seed the formation of Lewy body-like intracellular inclusions in cultured cells," Proceedings of the National Academy of Sciences, vol. 106(47): 20051-20056 (2009).
Luk et al., "Intracerebral inoculation of pathological a-synuclein initiates a rapidly progressive neurodegenerative α-synucleinopathy in mice," The Journal of Experimental Medicine, vol. 209(5): 975-986 (2012).

(56) References Cited

OTHER PUBLICATIONS

Luk et al., "Pathological α-Synuclein Transmission Initiates Parkinson-like Neurodegeneration in Nontransgenic Mice," Science, vol. 338: 949-953 (2012).
Masliah, et al., "Passive Immunization Reduces Behavorial and Neuropathological Deficts in an Alpha-Synuclein Transgenic Model of Lewy Body Disease," PLOS One, vol. 6(4) e19338 1-17 (2011).
Masuda-Suzukake et al., "Prion-like spreading of pathological α-synuclein in brain," Brain, vol. 136: 1128-1138 (2013).
Mollenhauer et al.,"α-Synuclein in human cerebrospinal fluid is principally derived from neurons of the central nervous system," Journal of Neural Transmission, vol. 119: 739-746 (2012).
Oganesyan et al., "Structural characterization of a human Fc fragment engineered for lack of effector functions," Acta Crystallographica Section D, vol. D64: 700-704 (2008).
Oueslati et al., "Role of post-translational modifications in modulating the structure, function and toxicity of α-synuclein: implications for Parkinson's disease pathogenesis and therapies," Progress in Brain Research, vol. 183: 115-145 (2010).
Pepinsky, et al., "LINGO-1 negatively regulates myelination by oligodendroctyes," Nature Neuroscience, vol. 8(6) 745-751(2005).
Recasens et al., "Alpha-synuclein spreading in Parkinson's disease," Frontiers in Neuroanatomy, vol. 8(159): 1-9 (2014).
Recasens et al., "Lewy Body Extracts from Parkinson Disease Brains Trigger a-Synuclein Pathology and Neurodegeneration in Mice and Monkeys," Annals of Neurology, vol. 75(3): 351-362 (2014).
Reese et al., "Fine structural localization of a blood-brain barrier to exogenous peroxidase," The Journal of Cell Biology, vol. 34: 207-217 (1967).
Rey et al., "Transfer of human α-synuclein from the olfactory bulb to interconnected brain regions in mice," Acta Neuropathologica, vol. 126: 555-573 (2013).
Rubin et al., "The cell biology of the blood-brain barrier," Annual Reviews in Neuroscience, vol. 22: 11-28 (1999).
Spillantini et al., "The α-Synucleinopathies: Parkinson's Disease, Dementia with Lewy Bodies, and Multiple System Atrophy," Annals of the New York Academy of Sciences: 16-27 (2000).
Tran et al., "α-Synuclein Immunotherapy Blocks Uptake and Templated Propagation of Misfolded α-Synuclein and Neurodegeneration," Cell Reports, vol. 7: 2054-2065 (2014).
Tsigelny et al., "Dynamics of α-synuclein aggregation and inhibition of pore-like oligomer development by β-synuclein," The FEBS Journal, vol. 274: 1862-1877 (2007).
Volpicelli-Daley et al., "Exogenous α-Synuclein Fibrils Induce Lewy Body Pathology Leading to Synaptic Dysfunction and Neuron Death," Neuron, vol. 72: 57-71 (2011).
Watts et al., "Transmission of multiple system atrophy prions to transgenic mice," Proceedings of the National Academy of Sciences, vol. 110(48): 19555-19560 (2013).
Winner et al., "In vivo demonstration that α-synuclein oligomers are toxic," Proceedings of the National Academy of Sciences, vol. 108(10): 4194-4199 (2011).
Heise et al. «Molecular-level secondary structure, polymorphism, and dynamics of full-length a-synuclein fibrils studied by solid-state NMR», PNAS Nov. 1, 2005 vol. 102 No. 44, 15871-15876.
Bousset et al. «Structural and functional characterization of two alpha-synuclein strains, Nature Communications, Oct. 10, 2013.
Mandler et al., "Active immunization against alpha-synuclein ameliorates the degenerative pathology and prevents demyelination in a model of multiple system atrophy," Molecular Neurodegeneration vol. 10(1): 15 pages (2015).
Kussie et al., "A Single Engineered Amino Acid Substitution Changes Antibody Fine Specificity," The Journal of Immunology, vol. 152(1): 146-52 (1994).
Edwards et al., "The Remarkable Flexibility of the Human Antibody Repertoire; Isolation of Over One Thousand Different Antibodies to a Single Protein, BLyS," The Journal of Molecular Biology, vol. 334: 103-118 (2003).
Chen et al., "Enhancement and destruction of antibody function by somatic mutation: unequal occurrence is controlled by V gene combinatorial associations," The EMBO Journal, vol. 14(12): 2784-2794 (1995).

Figure 2

```
VH Alignment       EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAG
                                             CDR1                              CDR2
asyn0087           ............................................................................................
aslo0452 ngl-3     ..............................S..HL.........................................................
aslo0543           .............................................................................................

CDR3
                   GAVNYYYYGMDYWGQGTMVTVSS
asyn0087           .......................
aslo0452 ngl-3     MHGK........T..........
aslo0543           RHGRI.......T..........

VL Alignment       QAVLTQPSSLSASPGASASLTCTLRSGINVGNYRIHWYQQKPGSPPQYLLRYKSDSDKHQGSGVPSRFSGSNDASANAGILLFISGLQSEDEADYYC
                                             CDR1                              CDR2
asyn0087           ............................................................................................
aslo0452 ngl-3     ...............A.........APLRK..............................................................L
aslo0543           .........................SGDSR..............................................................L CDR3
                   MIWHSGAWVFGGGTKLTVL
asyn0087           ...................
aslo0452 ngl-3     ...IH.V.Y..........
aslo0543           ...S...Y...........
```

Figure 3A

```
GAG GTG CAG CTG TTG GAG TCT GGG GGA GGC TTG GTA CAG CCT GGG GGG TCC CTG
 E   V   Q   L   L   E   S   G   G   G   L   V   Q   P   G   G   S   L

AGA CTC TCC TGT GCA GCC TCT GGA TTC ACC TTT AGC TAT GCC ATG AGC TGG
 R   L   S   C   A   A   S   G   F   T   F   S   Y   A   M   S   W
                                                     ‾‾‾‾‾‾‾‾‾‾‾‾‾
                                                         VHCDR1

GTC CGC CAG GCT CCA GGG AAG GGG CTG GAG TGG GTC TCA ATT TCC CAC CTT
 V   R   Q   A   P   G   K   G   L   E   W   V   S   I   S   H   L
                                                 ‾‾‾‾‾‾‾‾‾‾‾‾‾‾‾‾‾
                                                      VHCDR2

GGT GGT AGC ACA TAC TAT GCA GAC TCC GTG AAG GGC CGG TTC ACC ATC TCC AGA
 G   G   S   T   Y   Y   A   D   S   V   K   G   R   F   T   I   S   R

GAC AAT TCC AAG AAC ACG CTG TAT CTG CAA ATG AAC AGC CTG AGA GCC GAG GAC
 D   N   S   K   N   T   L   Y   L   Q   M   N   S   L   R   A   E   D

ACG GCC GTG TAT TAC TGT GCA AGA GGG AAG CAC GGG AAG TAC TAC TAC GGA
 T   A   V   Y   Y   C   A   R   G   K   H   G   K   Y   Y   Y   G
                             ‾‾‾‾‾‾‾‾‾‾‾‾‾‾‾‾‾‾‾‾‾‾‾‾‾‾‾‾‾‾‾‾‾‾‾‾‾
                                           VHCDR3

ATG GAC AAG TGG GGC CAA GGG ACC ACG GTC ACC GTC TCC TCA
 M   D   K   W   G   Q   G   T   T   V   T   V   S   S
```

Figure 3B

```
CAG GCT GTG CTG ACT CAG CCG GCT TCC CTC TCT GCG TCT CCT GGA GCA TCA GCC
 Q   A   V   L   T   Q   P   A   S   L   S   A   S   P   G   A   S   A

AGT CTC ACC TGC ACC TTG CGC AGT GGG GCG CCC CTG CCG AAG TAT AGG ATA TAC
 S   L   T   C   T   L   R   S   G   A   P   L   P   K   Y   R   I   Y
                              VLCDR1

TGG TAT CAG CAG AAG CCA CAG GGT CTT GGA GTC CCC CAG TAT CTC CTG AGG TAC AAA TCA
 W   Y   Q   Q   K   P   Q   G   S   G   V   P   Q   Y   L   L   R   Y   K   S
                                                                    VLCDR2

GAC GCA GAT AAA CAC CAG GGG ATC TCT GGG TCT CCC AGC CGC TTT TCT GGA TCC AAA
 D   A   D   K   H   Q   G   I   S   G   S   P   S   R   F   S   G   S   K

GAT GCT TCG GCC AAT GCA GGG ATT TTA CTC ATC TCT GGG CTC CAG TCT GAG GAT
 D   A   S   A   N   A   G   I   L   L   I   S   G   L   Q   S   E   D

GAG GCT GAC TAT TAT TGT ATG GTT TGG GAC CAC GGC GTC TGG TAT TTC GGC GGA
 E   A   D   Y   Y   C   M   V   W   D   H   G   V   W   Y   F   G   G
                                                VLCDR3

GGG ACC AAG CTG ACC GTC CTA
 G   T   K   L   T   V   L
```

Figure 3C

```
asic0452 ng1-3        EVQLLESGGGLVQPGGSLRLSCAASGFTFSSYAMSWVRQAPGKGLEWVS
IGHV3-23*01           EVQLLESGGGLVQPGGSLRLSCAASGFTFSSYAMSWVRQAPGKGLEWVS
Vernier (*)                                  ****         ****
                                                     VHCDR1 asic0452 ng1-3        SISHLGGSTYYADSVKGRFTISRDNSKNTLYLQMNSLRAEDTAVYYCAG
IGHV3-23*01           AISGSGGSTYYADSVKGRFTISRDNSKNTLYLQMNSLRAEDTAVYYCAK
Vernier (*)            *                *    *
                         VHCDR2 asic0452 ng1-3        GAMHGKYYYGMDKWGQGTTVTVSS
IGHJ6                            WGQGTTVTVSS
Vernier (*)                        *
                      VHCDR3
```

Figure 3D

```
asic0452 ng1-3        QAVLTQPASLSASPGASASLTCTLRSGAPLPKYRIYWYQQRPGSPPQILLR
IGLV5-45*01           QAVLTQPASLSASPGASASLTCTLRSGINVGTYRIYWYQQRPGSPPQILLR
Vernier (*)                                  *       ** *
                                        VLCDR1 asic0452 ng1-3        YKSDADKHQGSGVPSRFSGSKDASANAGILLISGLQSEDEADYYCMVNDHGVWV
IGLV5-45*01           YKSDSDKQQGSGVPSRFSGSKDASANAGILLISGLQSEDEADYYCMIWH...WV
Vernier (*)               *   *                                *
                      VLCDR2                                 VLCDR3 asic0452 ng1-3        FGGGTKLTV---L
IGVL2,3               FGGGTKLTV---L
Vernier (*)               *
```

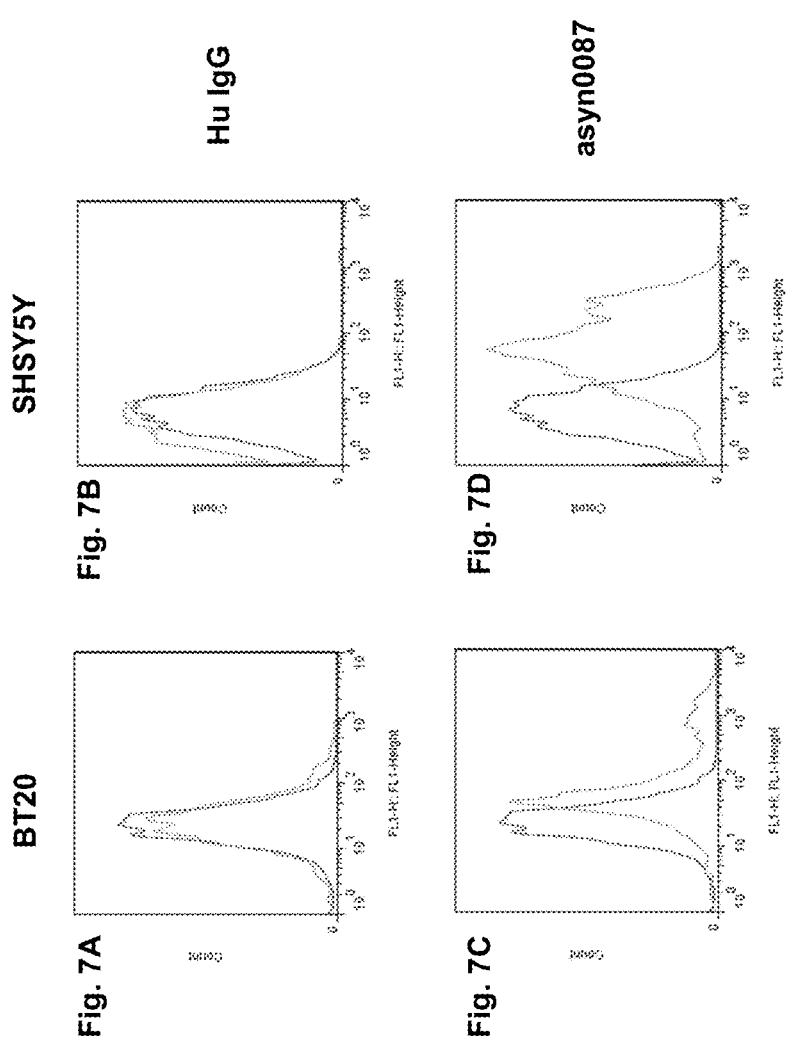

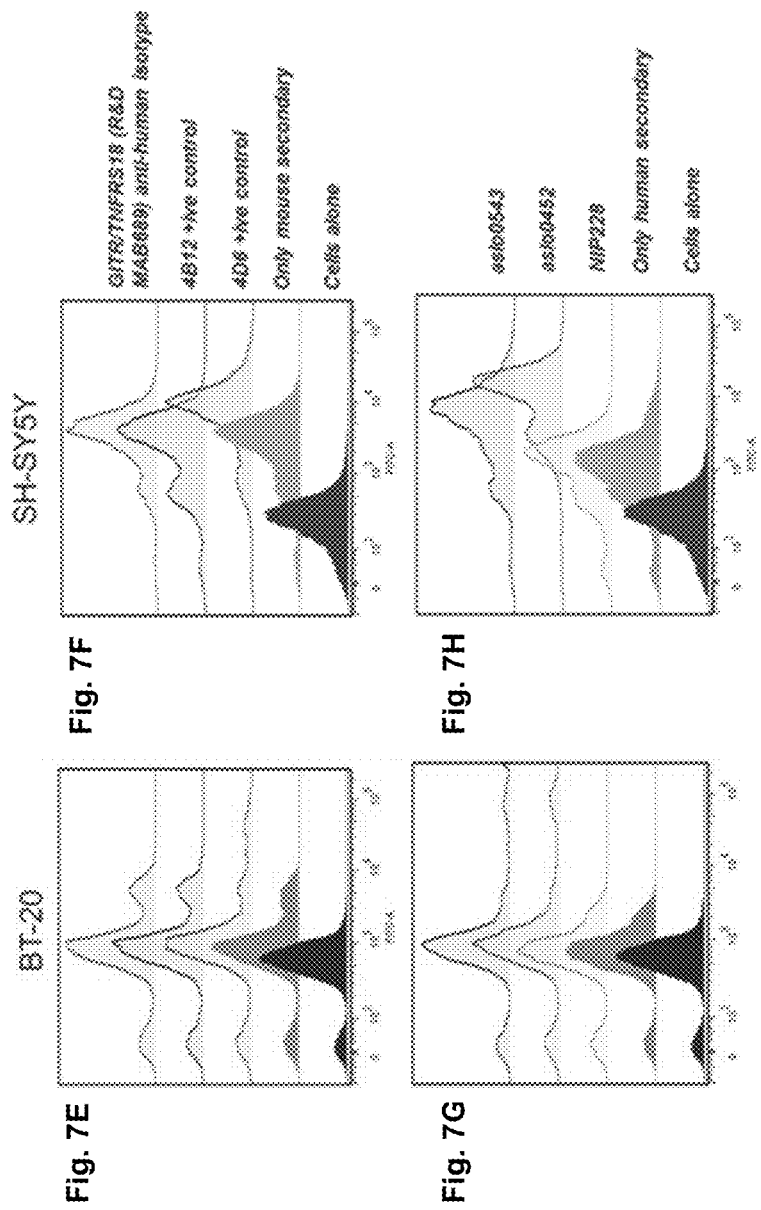

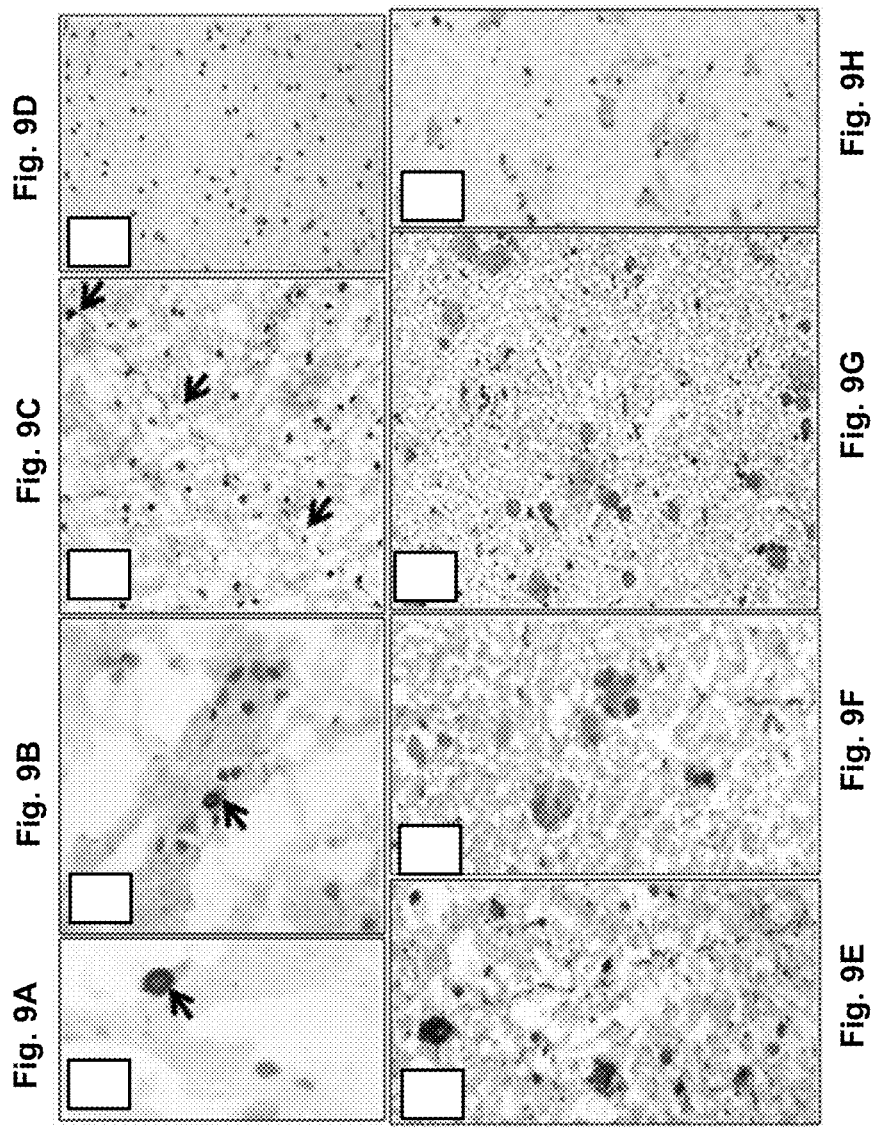

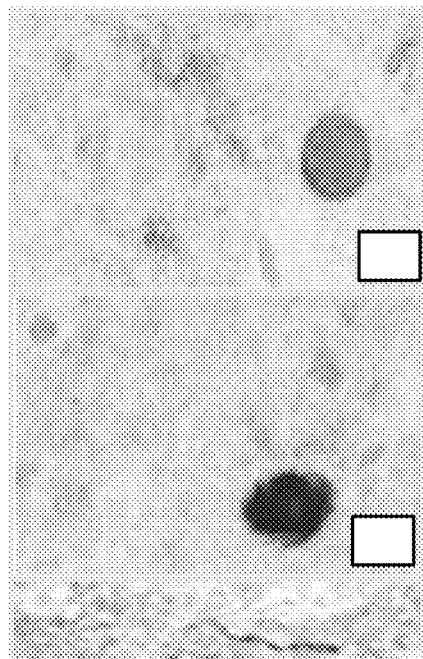
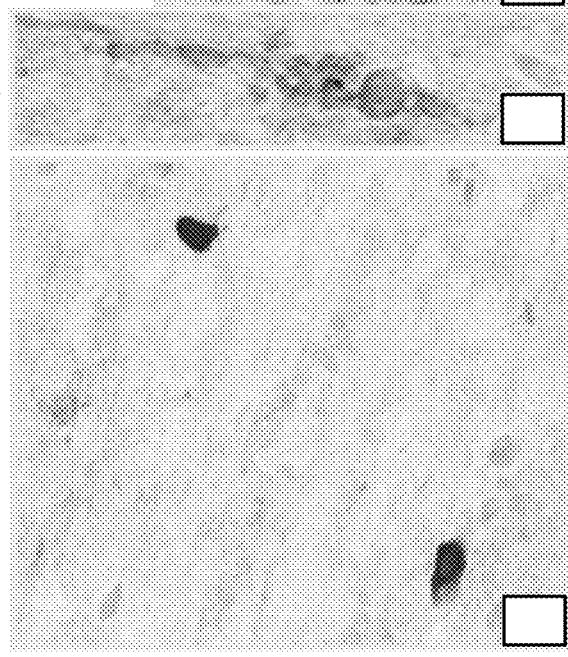
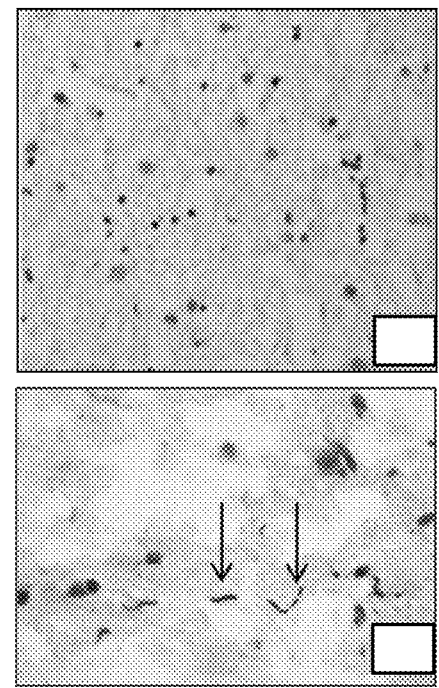
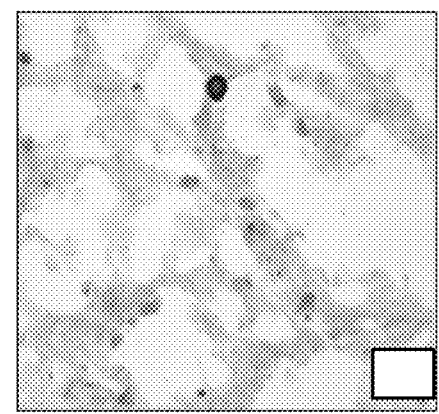

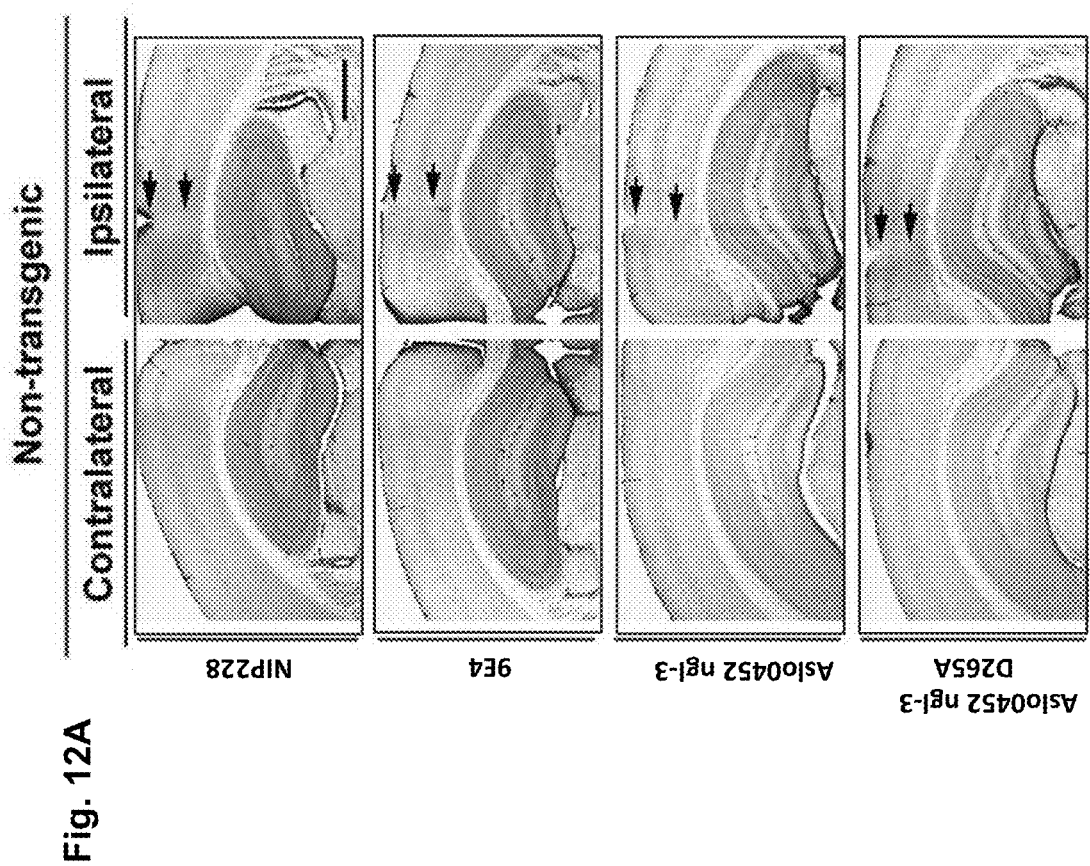

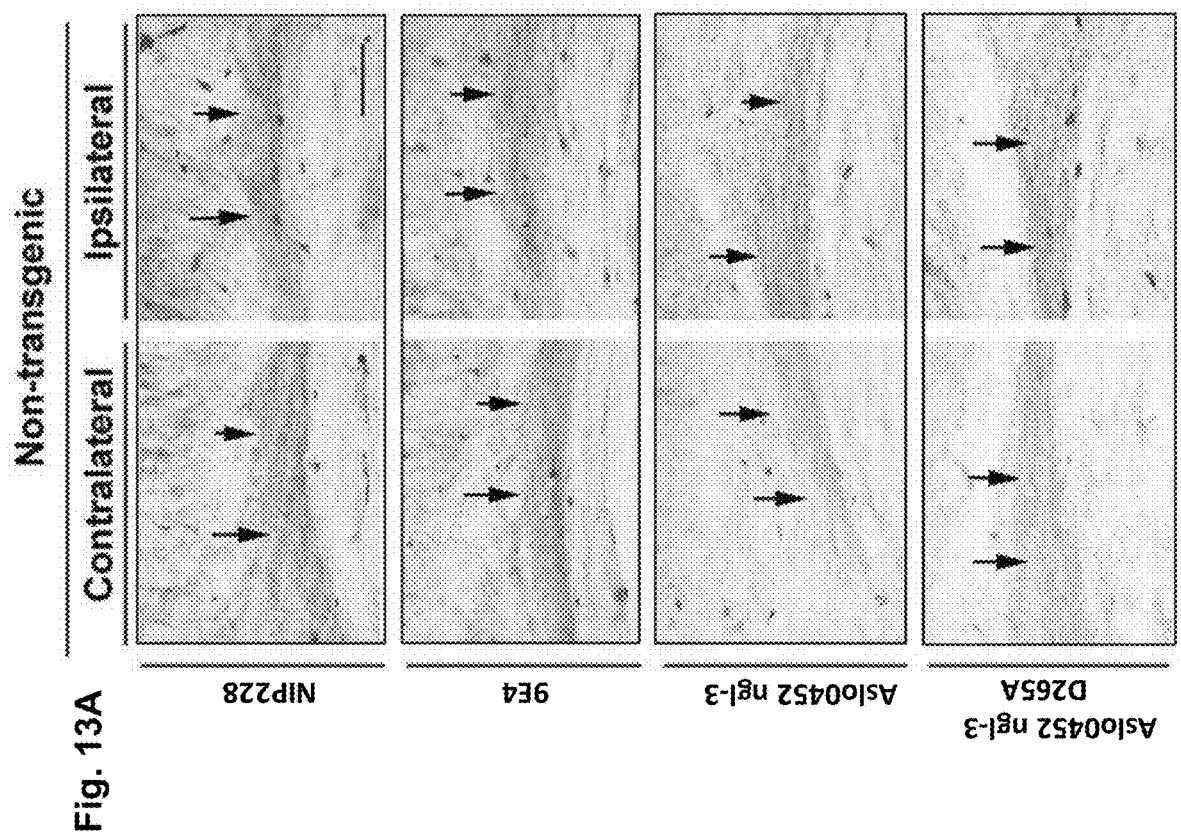

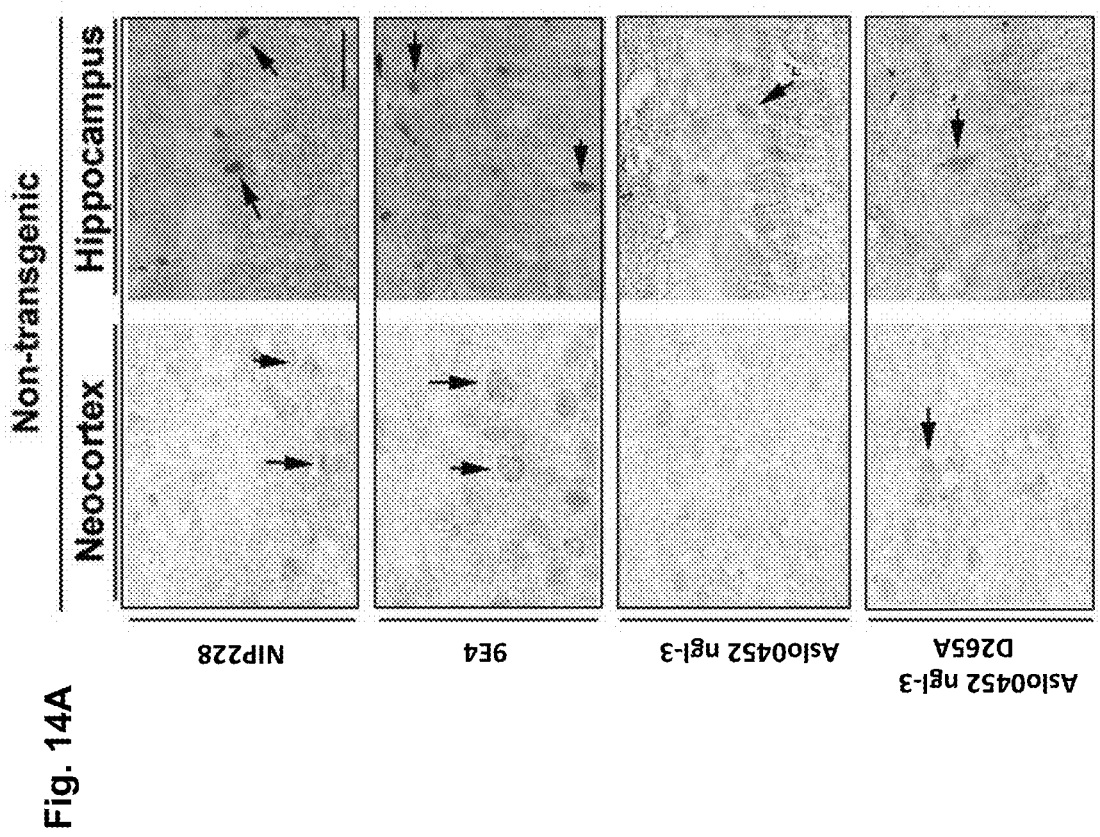

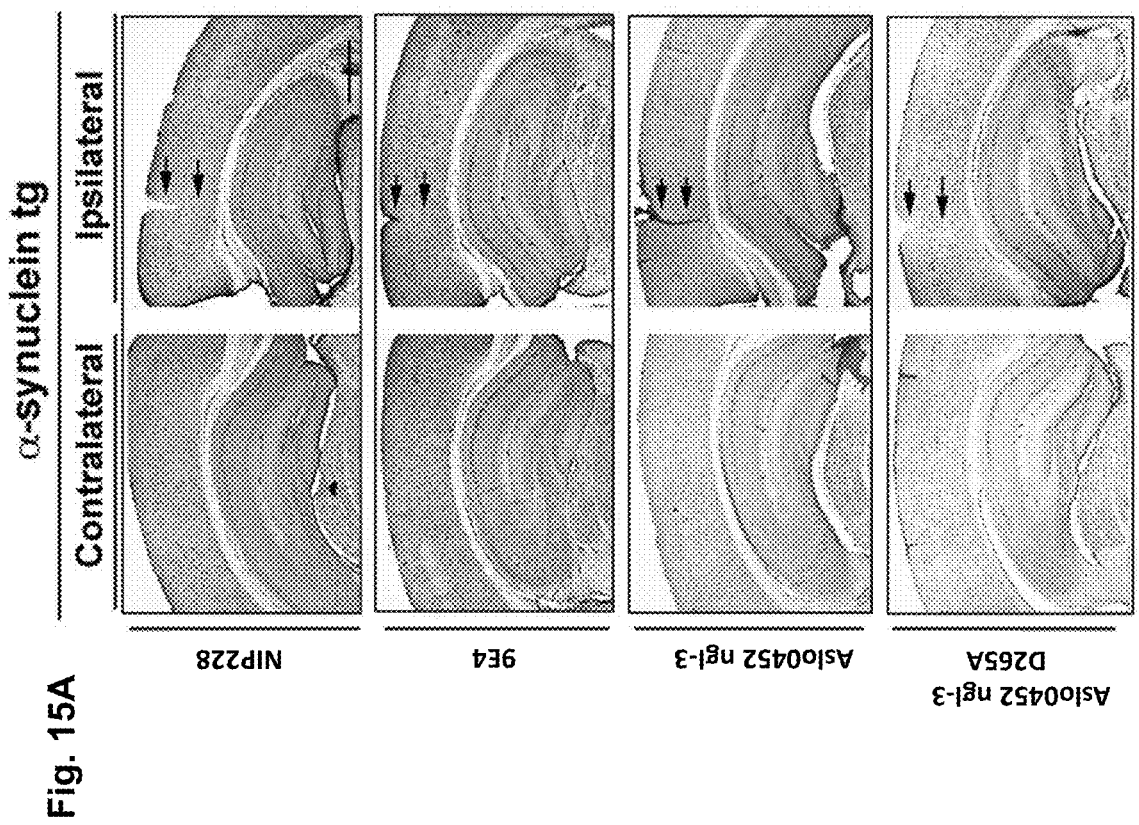

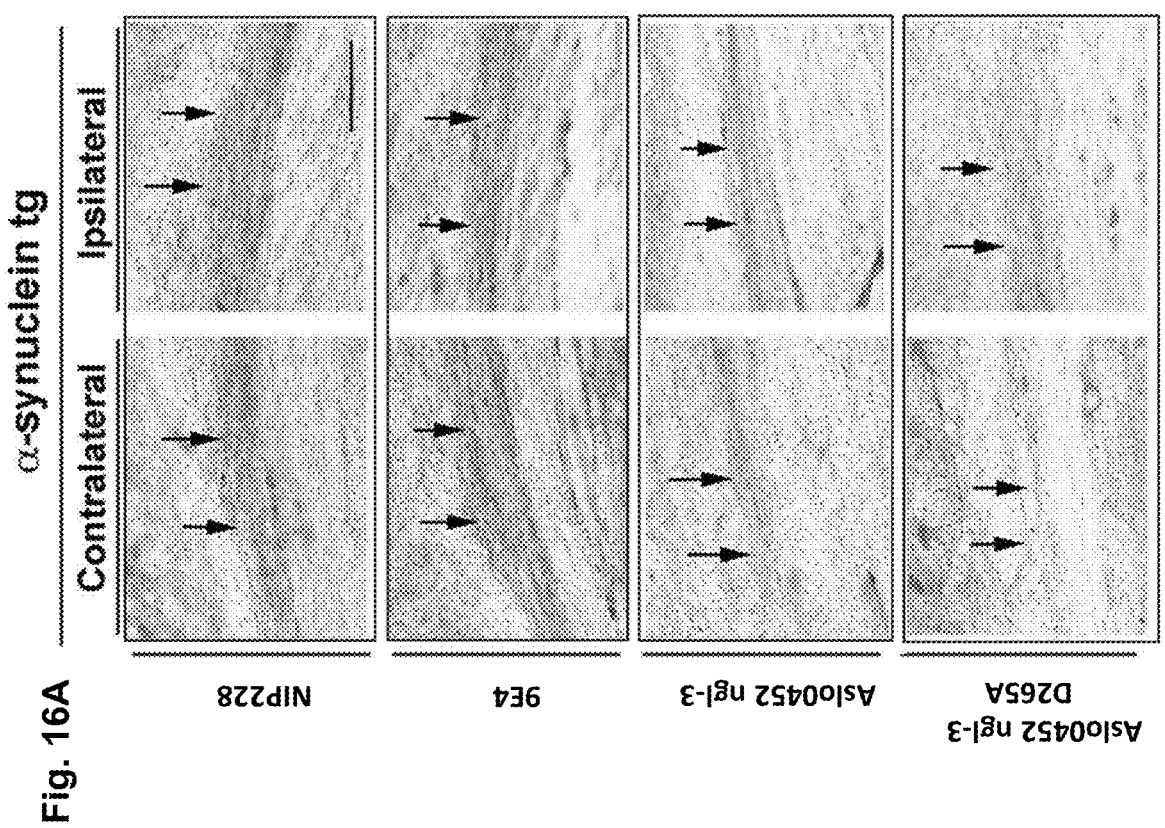

SEQUENCE LISTING

<160> NUMBER OF SEQ ID NOS: 61

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
        50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
            85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
            130                 135                 140

<210> SEQ ID NO 2
<211> LENGTH: 122
<212> TYPE: PRT
<213> ORGANISM: Homo sapiens

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Ala Val Asn Val Tyr Tyr Tyr Tyr Gly Met Asp Val Trp
            100                 105                 110

Gly Gln Gly Thr Met Val Thr Val Ser Ser
            115                 120

<210> SEQ ID NO 3
<211> LENGTH: 115
<212> TYPE: PRT
<213> ORGANISM: Homo sapiens

<400> SEQUENCE: 3

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Gly Asn Asn Val Gly Asn
            20                  25                  30

Tyr Arg Ile Tyr Trp Tyr Gln Gln Lys Ser Gly Ser Pro Pro Gln Tyr
            35                  40                  45

Leu Leu Arg Tyr Lys Ser Asp Ala Asp Lys His Gln Gly Ser Gly Val
    50                  55                  60

Pro Ser Arg Phe Ser Gly Ser Lys Asp Ala Ser Ala Asn Ala Gly Ile
65                  70                  75                  80

Leu Phe Ile Ser Gly Leu Gln Ser Glu Asp Glu Ala Asp Tyr Tyr Cys
            85                  90                  95

```
Met Val Trp His Ser Gly Ala Trp Val Phe Gly Gly Gly Thr Lys Leu
            100                 105                 110

Thr Val Leu
        115

<210> SEQ ID NO 4
<211> LENGTH: 122
<212> TYPE: PRT
<213> ORGANISM: Homo sapiens
<220> FEATURE:
<221> NAME/KEY: MOD_RES
<222> LOCATION: (50)..(50)
<223> OTHER INFORMATION: Ser or Ala
<220> FEATURE:
<221> NAME/KEY: MOD_RES
<222> LOCATION: (53)..(53)
<223> OTHER INFORMATION: His or Gly
<220> FEATURE:
<221> NAME/KEY: MOD_RES
<222> LOCATION: (54)..(54)
<223> OTHER INFORMATION: Leu or Ser
<220> FEATURE:
<221> NAME/KEY: MOD_RES
<222> LOCATION: (101)..(101)
<223> OTHER INFORMATION: Asn or Arg
<220> FEATURE:
<221> NAME/KEY: MOD_RES
<222> LOCATION: (102)..(102)
<223> OTHER INFORMATION: His or Arg
<220> FEATURE:
<221> NAME/KEY: MOD_RES
<222> LOCATION: (103)..(103)
<223> OTHER INFORMATION: Val or Gly
<220> FEATURE:
<221> NAME/KEY: MOD_RES
<222> LOCATION: (104)..(104)
<223> OTHER INFORMATION: Lys or Arg
<220> FEATURE:
<221> NAME/KEY: MOD_RES
<222> LOCATION: (105)..(105)
<223> OTHER INFORMATION: Tyr or Ile

<400> SEQUENCE: 4

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Xaa Ile Ser Xaa Xaa Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Ala Xaa Xaa Xaa Xaa Xaa Tyr Tyr Gly Met Asp Val Trp
            100                 105                 110

Gly Gln Gly Thr Met Val Thr Val Ser Ser
            115                 120

<210> SEQ ID NO 5
<211> LENGTH: 5
<212> TYPE: PRT
<213> ORGANISM: Homo sapiens

<400> SEQUENCE: 5
```

Ser Tyr Ala Met Ser
1               5

<210> SEQ ID NO 6
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Ser or Ala
<220> FEATURE:
<221> NAME/KEY: MOD_RES
<222> LOCATION: (4)..(4)
<223> OTHER INFORMATION: His or Gly
<220> FEATURE:
<221> NAME/KEY: MOD_RES
<222> LOCATION: (5)..(5)
<223> OTHER INFORMATION: Leu or Ser

<400> SEQUENCE: 6

Xaa Ile Ser Xaa Xaa Gly Gly Ser Thr Tyr Tyr Ala Asp Ser Val Lys
1               5                   10                  15

Gly

<210> SEQ ID NO 7
<211> LENGTH: 13
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Asn or Arg
<220> FEATURE:
<221> NAME/KEY: MOD_RES
<222> LOCATION: (4)..(4)
<223> OTHER INFORMATION: His or Arg
<220> FEATURE:
<221> NAME/KEY: MOD_RES
<222> LOCATION: (5)..(5)
<223> OTHER INFORMATION: Val or Gly
<220> FEATURE:
<221> NAME/KEY: MOD_RES
<222> LOCATION: (6)..(6)
<223> OTHER INFORMATION: Lys or Arg
<220> FEATURE:
<221> NAME/KEY: MOD_RES
<222> LOCATION: (7)..(7)
<223> OTHER INFORMATION: Tyr or Ile

<400> SEQUENCE: 7

Gly Ala Xaa Xaa Xaa Xaa Xaa Tyr Tyr Gly Met Asp Val
1               5                   10

<210> SEQ ID NO 8
<211> LENGTH: 114
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: Gly or Ser
<220> FEATURE:
<221> NAME/KEY: MOD_RES
<222> LOCATION: (28)..(28)
<223> OTHER INFORMATION: Ala or Gly
<220> FEATURE:
<221> NAME/KEY: MOD_RES
<222> LOCATION: (29)..(29)
<223> OTHER INFORMATION: Pro or Asp
<220> FEATURE:
<221> NAME/KEY: MOD_RES
<222> LOCATION: (30)..(30)

```
<223> OTHER INFORMATION: Leu or Phe
<220> FEATURE:
<221> NAME/KEY: MOD_RES
<222> LOCATION: (31)..(31)
<223> OTHER INFORMATION: Pro or Ser
<220> FEATURE:
<221> NAME/KEY: MOD_RES
<222> LOCATION: (32)..(32)
<223> OTHER INFORMATION: Lys or Arg
<220> FEATURE:
<221> NAME/KEY: MOD_RES
<222> LOCATION: (42)..(42)
<223> OTHER INFORMATION: Ser or Pro
<220> FEATURE:
<221> NAME/KEY: MOD_RES
<222> LOCATION: (82)..(82)
<223> OTHER INFORMATION: Phe or Leu
<220> FEATURE:
<221> NAME/KEY: MOD_RES
<222> LOCATION: (99)..(99)
<223> OTHER INFORMATION: Asp or Ser
<220> FEATURE:
<221> NAME/KEY: MOD_RES
<222> LOCATION: (100)..(100)
<223> OTHER INFORMATION: His or Ser
<220> FEATURE:
<221> NAME/KEY: MOD_RES
<222> LOCATION: (102)..(102)
<223> OTHER INFORMATION: Val or Ala
<220> FEATURE:
<221> NAME/KEY: MOD_RES
<222> LOCATION: (104)..(104)
<223> OTHER INFORMATION: Val or Tyr

<400> SEQUENCE: 8

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Xaa Xaa Xaa Xaa Xaa
            20                  25                  30

Tyr Arg Ile Tyr Trp Tyr Gln Gln Lys Xaa Gly Ser Pro Pro Gln Tyr
        35                  40                  45

Leu Leu Arg Tyr Lys Ser Asp Ala Asp Lys His Gln Gly Ser Gly Val
    50                  55                  60

Pro Ser Arg Phe Ser Gly Ser Lys Asp Ala Ser Ala Asn Ala Gly Ile
65                  70                  75                  80

Leu Xaa Ser Gly Leu Gln Ser Glu Asp Glu Ala Asp Tyr Tyr Cys Met
            85                  90                  95

Val Trp Xaa Xaa Gly Xaa Trp Xaa Phe Gly Gly Gly Thr Lys Leu Thr
            100                 105                 110

Val Leu

<210> SEQ ID NO 9
<211> LENGTH: 14
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Gly or Ser
<220> FEATURE:
<221> NAME/KEY: MOD_RES
<222> LOCATION: (6)..(6)
<223> OTHER INFORMATION: Ala or Gly
<220> FEATURE:
<221> NAME/KEY: MOD_RES
<222> LOCATION: (7)..(7)
<223> OTHER INFORMATION: Pro or Asp
<220> FEATURE:
<221> NAME/KEY: MOD_RES
<222> LOCATION: (8)..(8)
```

```
<223> OTHER INFORMATION: Leu or Phe
<220> FEATURE:
<221> NAME/KEY: MOD_RES
<222> LOCATION: (9)..(9)
<223> OTHER INFORMATION: Pro or Ser
<220> FEATURE:
<221> NAME/KEY: MOD_RES
<222> LOCATION: (10)..(10)
<223> OTHER INFORMATION: Lys or Arg

<400> SEQUENCE: 9

Thr Leu Arg Ser Xaa Xaa Xaa Xaa Xaa Xaa Tyr Arg Ile Tyr
1               5                   10

<210> SEQ ID NO 10
<211> LENGTH: 11
<212> TYPE: PRT
<213> ORGANISM: Homo sapiens

<400> SEQUENCE: 10

Tyr Lys Ser Asp Ala Asp Lys His Gln Gly Ser
1               5                   10

<210> SEQ ID NO 11
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Asp or Ser
<220> FEATURE:
<221> NAME/KEY: MOD_RES
<222> LOCATION: (5)..(5)
<223> OTHER INFORMATION: His or Ser
<220> FEATURE:
<221> NAME/KEY: MOD_RES
<222> LOCATION: (7)..(7)
<223> OTHER INFORMATION: Val or Ala
<220> FEATURE:
<221> NAME/KEY: MOD_RES
<222> LOCATION: (9)..(9)
<223> OTHER INFORMATION: Val or Tyr

<400> SEQUENCE: 11

Met Val Trp Xaa Xaa Gly Xaa Trp Xaa
1               5

<210> SEQ ID NO 12
<211> LENGTH: 452
<212> TYPE: PRT
<213> ORGANISM: Homo sapiens

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser His Leu Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

```
Ala Gly Gly Ala Asn His Gly Lys Tyr Tyr Gly Met Asp Lys Trp
                100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 13
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 13
```

```
gag gtg cag ctg ttg gag tct ggg gga ggc ttg gta cag cct ggg ggg     48
Glu Val Gln Leu Leu Glu Ser Gly Gly Gly Leu Val Gln Pro Gly Gly
1               5                   10                  15 tcc ctg aga ctc tcc tgt gca gcc tct gga ttc acc ttt agc agc tat     96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc    144
Ala Met Ser Trp Val Arg Gln Ala Pro Gly Lys Gly Leu Glu Trp Val
        35                  40                  45 tca tcc att tcc cac ctt ggt ggt agc aca tac tac gca gac tcc gtg    192
Ser Ser Ile Ser His Leu Gly Gly Ser Thr Tyr Tyr Ala Asp Ser Val
    50                  55                  60 aag ggc cgg ttc acc atc tcc aga gac aat tcc aag aac acg ctg tat    240
Lys Gly Arg Phe Thr Ile Ser Arg Asp Asn Ser Lys Asn Thr Leu Tyr
65                  70                  75                  80 ctg caa atg aac agc ctg aga gcc gag gac acg gcc gtg tat tac tgt    288
Leu Gln Met Asn Ser Leu Arg Ala Glu Asp Thr Ala Val Tyr Tyr Cys
                85                  90                  95 gcg gga ggg gca aac cac ggg aag tac tac tac gga atg gac aag tgg    336
Ala Gly Gly Ala Asn His Gly Lys Tyr Tyr Tyr Gly Met Asp Lys Trp
            100                 105                 110 ggc caa ggg acc acg gtc acc gtc tcc tca                            366
Gly Gln Gly Thr Thr Val Thr Val Ser Ser
        115                 120
```

<210> SEQ ID NO 14
<211> LENGTH: 122
<212> TYPE: PRT
<213> ORGANISM: Homo sapiens

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser His Leu Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Ala Asn His Gly Lys Tyr Tyr Tyr Gly Met Asp Lys Trp
            100                 105                 110

Gly Gln Gly Thr Thr Val Thr Val Ser Ser
        115                 120

<210> SEQ ID NO 15
<211> LENGTH: 17
<212> TYPE: PRT
<213> ORGANISM: Homo sapiens

<400> SEQUENCE: 15

Ser Ile Ser His Leu Gly Gly Ser Thr Tyr Tyr Ala Asp Ser Val Lys
1               5                   10                  15

Gly

-continued

<210> SEQ ID NO 16
<211> LENGTH: 13
<212> TYPE: PRT
<213> ORGANISM: Homo sapiens

<400> SEQUENCE: 16

Gly Ala Asn His Gly Lys Tyr Tyr Tyr Gly Met Asp Lys
1               5                   10

<210> SEQ ID NO 17
<211> LENGTH: 221
<212> TYPE: PRT
<213> ORGANISM: Homo sapiens

<400> SEQUENCE: 17

Gln Ala Val Leu Thr Gln Pro Ala Ser Leu Ser Ala Ser Pro Gly Ala
1               5                   10                  15

Ser Ala Ser Leu Thr Cys Thr Leu Arg Ser Gly Ala Pro Leu Pro Lys
                20                  25                  30

Tyr Arg Ile Tyr Trp Tyr Gln Gln Lys Pro Gly Ser Pro Pro Gln Tyr
            35                  40                  45

Leu Leu Arg Tyr Lys Ser Asp Ala Asp Lys His Gln Gly Ser Gly Val
50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Val Trp Asp His Gly Val Trp Tyr Phe Gly Gly Gly Thr Lys Leu
            100                 105                 110

Thr Val Leu Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
    210                 215                 220

<210> SEQ ID NO 18
<211> LENGTH: 345
<212> TYPE: DNA
<213> ORGANISM: Homo sapiens

<400> SEQUENCE: 18
caggctgtgc tgactcagcc ggcttccctc tctgcgtctc ctggagcatc agccagtctc      60
acctgcacct tgcgcagtgg ggcgcccctg ccgaagtata ggatatactg gtatcagcag     120
aagccaggga gtcctcccca gtatctcctg aggtacaaat cagacgcaga taaacaccag     180
ggctctggag tccccagccg ctttctgga tccaaagatg cttcggccaa tgcaggatt       240 ttactcatct ctgggctcca gtctgaggat gaggctgact attattgtat ggtttgggac     300
cacggcgtct ggtatttcgg cggagggacc aagctgaccg tccta                     345

<210> SEQ ID NO 19
<211> LENGTH: 115
<212> TYPE: PRT
<213> ORGANISM: Homo sapiens

<400> SEQUENCE: 19

Gln Ala Val Leu Thr Gln Pro Ala Ser Leu Ser Ala Ser Pro Gly Ala
1               5                   10                  15

Ser Ala Ser Leu Thr Cys Thr Leu Arg Ser Gly Ala Pro Leu Pro Lys
                20                  25                  30

Tyr Arg Ile Tyr Trp Tyr Gln Gln Lys Pro Gly Ser Pro Pro Gln Tyr
            35                  40                  45

Leu Leu Arg Tyr Lys Ser Asp Ala Asp Lys His Gln Gly Ser Gly Val
        50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Val Trp Asp His Gly Val Trp Tyr Phe Gly Gly Gly Thr Lys Leu
            100                 105                 110

Thr Val Leu
        115

<210> SEQ ID NO 20
<211> LENGTH: 14
<212> TYPE: PRT
<213> ORGANISM: Homo sapiens

<400> SEQUENCE: 20

Thr Leu Arg Ser Gly Ala Pro Leu Pro Lys Tyr Arg Ile Tyr
1               5                   10

<210> SEQ ID NO 21
<211> LENGTH: 9
<212> TYPE: PRT
<213> ORGANISM: Homo sapiens

<400> SEQUENCE: 21

Met Val Trp Asp His Gly Val Trp Tyr
1               5

<210> SEQ ID NO 22
<211> LENGTH: 452
<212> TYPE: PRT
<213> ORGANISM: Homo sapiens

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
            85                  90                  95
Ala Gly Gly Ala Arg Gly Arg Ile Tyr Tyr Gly Met Asp Lys Trp
            100                 105                 110
Gly Gln Gly Thr Thr Val Thr Val Ser Ser Ala Ser Thr Lys Gly Pro
            115                 120                 125
Ser Val Phe Pro Leu Ala Pro Ser Ser Lys Ser Thr Ser Gly Gly Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Gln Thr Tyr Ile Cys Asn Val Asn
                195                 200                 205
His Lys Pro Ser Asn Thr Lys Val Asp Lys Arg Val Glu Pro Lys Ser
            210                 215                 220
Cys Asp Lys Thr His Thr Cys Pro Pro Cys Pro Ala Pro Glu Phe Glu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
                260                 265                 270
His Glu Asp Pro Glu Val Lys Phe Asn Trp Tyr Val Asp Gly Val Glu
            275                 280                 285
Val His Asn Ala Lys Thr Lys Pro Arg Glu Glu Gln Tyr Asn Ser Thr
290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Ser
                325                 330                 335
Ile Glu Lys Thr Ile Ser Lys Ala Lys Gly Gln Pro Arg Glu Pro Gln
                340                 345                 350
Val Tyr Thr Leu Pro Pro Ser Arg Glu Glu Met Thr Lys Asn Gln Val
            355                 360                 365
Ser Leu Thr Cys Leu Val Lys Gly Phe Tyr Pro Ser Asp Ile Ala Val
            370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
                420                 425                 430
Met His Glu Ala Leu His Asn His Tyr Thr Gln Lys Ser Leu Ser Leu
                435                 440                 445
Ser Pro Gly Lys
    450

<210> SEQ ID NO 23
<211> LENGTH: 366
<212> TYPE: DNA
<213> ORGANISM: Homo sapiens

<400> SEQUENCE: 23
```

```
gaggtgcagc tgttggagtc tggggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtgt attactgtgc gggaggggca   300
cggcgcgggc gcatctacta cggaatggac aaatgggggcc aagggacaac ggtcaccgtc   360
tcctca                                                              366
```

<210> SEQ ID NO 24
<211> LENGTH: 122
<212> TYPE: PRT
<213> ORGANISM: Homo sapiens

<400> SEQUENCE: 24

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Ala Arg Arg Gly Arg Ile Tyr Tyr Gly Met Asp Lys Trp
            100                 105                 110

Gly Gln Gly Thr Thr Val Thr Val Ser Ser
        115                 120
```

<210> SEQ ID NO 25
<211> LENGTH: 5
<212> TYPE: PRT
<213> ORGANISM: Homo sapiens

<400> SEQUENCE: 25

```
Ser Tyr Ala Met Ser
1               5
```

<210> SEQ ID NO 26
<211> LENGTH: 17
<212> TYPE: PRT
<213> ORGANISM: Homo sapiens

<400> SEQUENCE: 26

```
Ala Ile Ser Gly Ser Gly Gly Ser Thr Tyr Tyr Ala Asp Ser Val Lys
1               5                   10                  15

Gly
```

<210> SEQ ID NO 27
<211> LENGTH: 13
<212> TYPE: PRT
<213> ORGANISM: Homo sapiens

<400> SEQUENCE: 27

```
Gly Ala Arg Arg Gly Arg Ile Tyr Tyr Gly Met Asp Lys
```

<210> SEQ ID NO 28
<211> LENGTH: 221
<212> TYPE: PRT
<213> ORGANISM: Homo sapiens

<400> SEQUENCE: 28

```
Gln Ala Val Leu Thr Gln Pro Ala Ser Leu Ser Ala Ser Pro Gly Ala
1               5                   10                  15

Ser Ala Ser Leu Thr Cys Thr Leu Arg Ser Ser Gly Asp Phe Ser Arg
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ala Asp Lys His Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Val Trp Ser Ser Gly Ala Trp Tyr Phe Gly Gly Thr Lys Leu
            100                 105                 110

Thr Val Leu Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
    130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
    210                 215                 220
```

<210> SEQ ID NO 29
<211> LENGTH: 345
<212> TYPE: DNA
<213> ORGANISM: Homo sapiens

<400> SEQUENCE: 29

```
caggctgtgc tgactcagcc ggcttccctc tctgcgtctc ctggagcatc agccagtctc      60
acctgcacct tgcgcagttc cggggacttc tcccggtata ggatatactg gtatcagcag     120
aagccaggga gtcctcccca gtatctcctg aggtacaaat cagacgcaga taaacaccag     180
ggctctggag tccccagccg ctttctgga tccaaagatg cttcggccaa tgcagggatt      240
ttactcatct ctgggctcca gtctgaggat gaggctgact attattgtat ggtttggtcc     300
agcggcgctt ggtacttcgg cggagggacc aagctgaccg tccta                     345
```

<210> SEQ ID NO 30
<211> LENGTH: 115
<212> TYPE: PRT
<213> ORGANISM: Homo sapiens

<400> SEQUENCE: 30

Gln Ala Val Leu Thr Gln Pro Ala Ser Leu Ser Ala Ser Pro Gly Ala
1               5                   10                  15

Ser Ala Ser Leu Thr Cys Thr Leu Arg Ser Ser Gly Asp Phe Ser Arg
            20                  25                  30

Tyr Arg Ile Tyr Trp Tyr Gln Gln Lys Pro Gly Ser Pro Gln Tyr
        35                  40                  45

Leu Leu Arg Tyr Lys Ser Asp Ala Asp Lys His Gln Gly Ser Gly Val
50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Val Trp Ser Ser Gly Ala Trp Tyr Phe Gly Gly Gly Thr Lys Leu
            100                 105                 110

Thr Val Leu
    115

<210> SEQ ID NO 31
<211> LENGTH: 14
<212> TYPE: PRT
<213> ORGANISM: Homo sapiens

<400> SEQUENCE: 31

Thr Leu Arg Ser Ser Gly Asp Phe Ser Arg Tyr Arg Ile Tyr
1               5                   10

<210> SEQ ID NO 32
<211> LENGTH: 11
<212> TYPE: PRT
<213> ORGANISM: Homo sapiens

<400> SEQUENCE: 32

Tyr Lys Ser Asp Ala Asp Lys His Gln Gly Ser
1               5                   10

<210> SEQ ID NO 33
<211> LENGTH: 9
<212> TYPE: PRT
<213> ORGANISM: Homo sapiens

<400> SEQUENCE: 33

Met Val Trp Ser Ser Gly Ala Trp Tyr
1               5

<210> SEQ ID NO 34
<211> LENGTH: 123
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Gln or Val
<220> FEATURE:
<221> NAME/KEY: MOD_RES
<222> LOCATION: (11)..(11)
<223> OTHER INFORMATION: Val or Leu
<220> FEATURE:
<221> NAME/KEY: MOD_RES
<222> LOCATION: (75)..(75)
<223> OTHER INFORMATION: Ser or Arg

<400> SEQUENCE: 34

Xaa Val Gln Leu Val Gln Ser Gly Ala Glu Xaa Lys Lys Pro Gly Ser

```
                1               5                  10                 15
            Ser Val Lys Val Ser Cys Lys Ala Ser Gly Gly Thr Phe Ser Ser Tyr
                           20                 25                 30
            Ala Ile Ser Trp Val Arg Gln Ala Pro Gly Gln Gly Leu Glu Trp Met
                           35                 40                 45
            Gly Arg Ile Ile Pro Ile Leu Gly Thr Ser Asn Tyr Ala Gln Lys Phe
                   50                 55                 60
            Gln Gly Arg Val Thr Ile Thr Ala Asp Glu Xaa Thr Ser Thr Ala Tyr
            65                 70                 75                 80
            Met Glu Leu Ser Ser Leu Arg Ser Glu Asp Thr Ala Val Tyr Tyr Cys
                           85                 90                 95
            Ala Arg Arg Ser Ser Leu Ala Ala Ala Asp Arg Gly Ala Phe Asp Ile
                           100                105                110
            Trp Gly Gln Gly Thr Met Val Thr Val Ser Ser
                       115                120
```

<210> SEQ ID NO 35
<211> LENGTH: 108
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Arg, Gly or Ala
<220> FEATURE:
<221> NAME/KEY: MOD_RES
<222> LOCATION: (28)..(28)
<223> OTHER INFORMATION: Thr or Arg
<220> FEATURE:
<221> NAME/KEY: MOD_RES
<222> LOCATION: (29)..(29)
<223> OTHER INFORMATION: Ser, Arg or Thr
<220> FEATURE:
<221> NAME/KEY: MOD_RES
<222> LOCATION: (32)..(32)
<223> OTHER INFORMATION: Ala or Thr
<220> FEATURE:
<221> NAME/KEY: MOD_RES
<222> LOCATION: (33)..(33)
<223> OTHER INFORMATION: Asn or Ser
<220> FEATURE:
<221> NAME/KEY: MOD_RES
<222> LOCATION: (37)..(37)
<223> OTHER INFORMATION: His or Gln
<220> FEATURE:
<221> NAME/KEY: MOD_RES
<222> LOCATION: (44)..(44)
<223> OTHER INFORMATION: Val or Ile
<220> FEATURE:
<221> NAME/KEY: MOD_RES
<222> LOCATION: (47)..(47)
<223> OTHER INFORMATION: Met or Ile
<220> FEATURE:
<221> NAME/KEY: MOD_RES
<222> LOCATION: (50)..(50)
<223> OTHER INFORMATION: Lys or Glu
<220> FEATURE:
<221> NAME/KEY: MOD_RES
<222> LOCATION: (51)..(51)
<223> OTHER INFORMATION: Asn or Asp
<220> FEATURE:
<221> NAME/KEY: MOD_RES
<222> LOCATION: (57)..(57)
<223> OTHER INFORMATION: Val or Ile
<220> FEATURE:
<221> NAME/KEY: MOD_RES
<222> LOCATION: (65)..(65)
<223> OTHER INFORMATION: Ser or Arg
<220> FEATURE:
<221> NAME/KEY: MOD_RES
<222> LOCATION: (68)..(68)

```
<223> OTHER INFORMATION: Asn or Thr
<220> FEATURE:
<221> NAME/KEY: MOD_RES
<222> LOCATION: (92)..(92)
<223> OTHER INFORMATION: Ser or Asn
<220> FEATURE:
<221> NAME/KEY: MOD_RES
<222> LOCATION: (93)..(93)
<223> OTHER INFORMATION: Ser or Thr
<220> FEATURE:
<221> NAME/KEY: MOD_RES
<222> LOCATION: (95)..(95)
<223> OTHER INFORMATION: Asn, Lys or His
<220> FEATURE:
<221> NAME/KEY: MOD_RES
<222> LOCATION: (96)..(96)
<223> OTHER INFORMATION: His or Pro
<220> FEATURE:
<221> NAME/KEY: MOD_RES
<222> LOCATION: (97)..(97)
<223> OTHER INFORMATION: Val or Trp

<400> SEQUENCE: 35

Ser Ser Glu Leu Thr Gln Asp Pro Ala Val Ser Val Ala Leu Xaa Gln
1               5                   10                  15

Thr Val Arg Ile Thr Cys Gln Gly Asp Ser Leu Xaa Xaa Tyr Tyr Xaa
            20                  25                  30

Xaa Trp Tyr Gln Xaa Lys Pro Gly Gln Ala Pro Xaa Leu Val Xaa Tyr
        35                  40                  45

Gly Xaa Xaa Asn Arg Pro Ser Gly Xaa Pro Asp Arg Phe Ser Gly Ser
    50                  55                  60

Xaa Ser Gly Xaa Thr Ala Ser Leu Thr Ile Thr Gly Ala Gln Ala Glu
65                  70                  75                  80

Asp Glu Ala Asp Tyr Tyr Cys Asn Ser Arg Asp Xaa Xaa Gly Xaa Xaa
                85                  90                  95

Xaa Val Phe Gly Gly Gly Thr Lys Leu Thr Val Leu
            100                 105

<210> SEQ ID NO 36
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Thr or Arg
<220> FEATURE:
<221> NAME/KEY: MOD_RES
<222> LOCATION: (7)..(7)
<223> OTHER INFORMATION: Ser, Arg or Thr
<220> FEATURE:
<221> NAME/KEY: MOD_RES
<222> LOCATION: (10)..(10)
<223> OTHER INFORMATION: Ala or Thr
<220> FEATURE:
<221> NAME/KEY: MOD_RES
<222> LOCATION: (11)..(11)
<223> OTHER INFORMATION: Asn or Ser

<400> SEQUENCE: 36

Gln Gly Asp Ser Leu Xaa Xaa Tyr Tyr Xaa Xaa
1               5                   10

<210> SEQ ID NO 37
<211> LENGTH: 7
<212> TYPE: PRT
<213> ORGANISM: Homo sapiens
<220> FEATURE:
<221> NAME/KEY: MOD_RES
```

```
<222> LOCATION: (2)..(2)
<223> OTHER INFORMATION: Lys or Glu
<220> FEATURE:
<221> NAME/KEY: MOD_RES
<222> LOCATION: (3)..(3)
<223> OTHER INFORMATION: Asn or Asp

<400> SEQUENCE: 37

Gly Xaa Xaa Asn Arg Pro Ser
1               5

<210> SEQ ID NO 38
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Ser or Asn
<220> FEATURE:
<221> NAME/KEY: MOD_RES
<222> LOCATION: (6)..(6)
<223> OTHER INFORMATION: Ser or Thr
<220> FEATURE:
<221> NAME/KEY: MOD_RES
<222> LOCATION: (8)..(8)
<223> OTHER INFORMATION: Asn, Lys or His
<220> FEATURE:
<221> NAME/KEY: MOD_RES
<222> LOCATION: (9)..(9)
<223> OTHER INFORMATION: His or Pro
<220> FEATURE:
<221> NAME/KEY: MOD_RES
<222> LOCATION: (10)..(10)
<223> OTHER INFORMATION: Val or Trp

<400> SEQUENCE: 38

Asn Ser Arg Asp Xaa Xaa Gly Xaa Xaa Xaa Val
1               5                   10

<210> SEQ ID NO 39
<211> LENGTH: 123
<212> TYPE: PRT
<213> ORGANISM: Homo sapiens

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Thr Ser Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ser Ser Leu Ala Ala Ala Asp Arg Gly Ala Phe Asp Ile
            100                 105                 110

Trp Gly Gln Gly Thr Met Val Thr Val Ser Ser
        115                 120

<210> SEQ ID NO 40
<211> LENGTH: 5
<212> TYPE: PRT
```

```
<213> ORGANISM: Homo sapiens

<400> SEQUENCE: 40

Ser Tyr Ala Ile Ser
1               5

<210> SEQ ID NO 41
<211> LENGTH: 17
<212> TYPE: PRT
<213> ORGANISM: Homo sapiens

<400> SEQUENCE: 41

Arg Ile Ile Pro Ile Leu Gly Thr Ser Asn Tyr Ala Gln Lys Phe Gln
1               5                   10                  15

Gly

<210> SEQ ID NO 42
<211> LENGTH: 14
<212> TYPE: PRT
<213> ORGANISM: Homo sapiens

<400> SEQUENCE: 42

Arg Ser Ser Leu Ala Ala Asp Arg Gly Ala Phe Asp Ile
1               5                   10

<210> SEQ ID NO 43
<211> LENGTH: 108
<212> TYPE: PRT
<213> ORGANISM: Homo sapiens

<400> SEQUENCE: 43

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
            100                 105

<210> SEQ ID NO 44
<211> LENGTH: 11
<212> TYPE: PRT
<213> ORGANISM: Homo sapiens

<400> SEQUENCE: 44

Gln Gly Asp Ser Leu Arg Ser Tyr Tyr Ala Ser
1               5                   10

<210> SEQ ID NO 45
<211> LENGTH: 7
<212> TYPE: PRT
<213> ORGANISM: Homo sapiens

<400> SEQUENCE: 45
```

-continued

Gly Lys Asn Asn Arg Pro Ser
1               5

<210> SEQ ID NO 46
<211> LENGTH: 11
<212> TYPE: PRT
<213> ORGANISM: Homo sapiens

<400> SEQUENCE: 46

Asn Ser Arg Asp Ser Ser Gly Asn His Val Val
1               5                   10

<210> SEQ ID NO 47
<211> LENGTH: 123
<212> TYPE: PRT
<213> ORGANISM: Homo sapiens
<220> FEATURE:
<223> OTHER INFORMATION: Bbbt0626 VH

<400> SEQUENCE: 47

Gly Val Gln Leu Val Gln Ser Gly Ala Glu Leu Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Thr Ser Asn Tyr Ala Gln Lys Phe
    50                  55                  60

Gln Gly Arg Val Thr Ile Thr Ala Asp Glu Arg Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ser Ser Leu Ala Ala Ala Asp Arg Gly Ala Phe Asp Ile
            100                 105                 110

Trp Gly Gln Gly Thr Met Val Thr Val Ser Ser
        115                 120

<210> SEQ ID NO 48
<211> LENGTH: 122
<212> TYPE: PRT
<213> ORGANISM: Homo sapiens

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gly Thr Tyr
            20                  25                  30

Ser Ile Thr Trp Val Arg Gln Ala Pro Gly Gln Gly Leu Glu Trp Met
        35                  40                  45

Gly Asp Ile Val Pro Ile Phe Gly Thr Pro Asn Tyr Ala Gln Asn Phe
    50                  55                  60

Gln Gly Arg Val Thr Ile Ser Ala Asp Val Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Arg Gly Ser Tyr Tyr Gly Arg Gly Gly Trp Phe Asp Pro Trp
            100                 105                 110

Gly Arg Gly Thr Leu Val Thr Val Ser Ser
        115                 120

<210> SEQ ID NO 49
<211> LENGTH: 5
<212> TYPE: PRT
<213> ORGANISM: Homo sapiens

<400> SEQUENCE: 49

Thr Tyr Ser Ile Thr
1               5

<210> SEQ ID NO 50
<211> LENGTH: 17
<212> TYPE: PRT
<213> ORGANISM: Homo sapiens

<400> SEQUENCE: 50

Asp Ile Val Pro Ile Phe Gly Thr Pro Asn Tyr Ala Gln Asn Phe Gln
1               5                   10                  15

Gly

<210> SEQ ID NO 51
<211> LENGTH: 13
<212> TYPE: PRT
<213> ORGANISM: Homo sapiens

<400> SEQUENCE: 51

Arg Gly Ser Tyr Tyr Gly Arg Gly Gly Trp Phe Asp Pro
1               5                   10

<210> SEQ ID NO 52
<211> LENGTH: 122
<212> TYPE: PRT
<213> ORGANISM: Homo sapiens

<400> SEQUENCE: 52

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gly Thr Tyr
            20                  25                  30

Ser Ile Thr Trp Val Arg Gln Ala Pro Gly Gln Gly Leu Glu Trp Met
        35                  40                  45

Gly Asp Ile Val Pro Ile Phe Gly Thr Pro Asn Tyr Ala Gln Asn Phe
    50                  55                  60

Gln Gly Arg Val Thr Ile Ser Ala Asp Val Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Arg Gly Ser Tyr Tyr Gly Arg Gly Gly Trp Phe Asp Pro Trp
            100                 105                 110

Gly Arg Gly Thr Leu Val Thr Val Ser Ser
        115                 120

<210> SEQ ID NO 53
<211> LENGTH: 5
<212> TYPE: PRT
<213> ORGANISM: Homo sapiens

<400> SEQUENCE: 53

Thr Tyr Ser Ile Thr
1               5

<210> SEQ ID NO 54
<211> LENGTH: 17
<212> TYPE: PRT
<213> ORGANISM: Homo sapiens

<400> SEQUENCE: 54

Asp Ile Val Pro Ile Phe Gly Thr Pro Asn Tyr Ala Gln Asn Phe Gln
1               5                   10                  15

Gly

<210> SEQ ID NO 55
<211> LENGTH: 13
<212> TYPE: PRT
<213> ORGANISM: Homo sapiens

<400> SEQUENCE: 55

Arg Gly Ser Tyr Tyr Gly Arg Gly Gly Trp Phe Asp Pro
1               5                   10

<210> SEQ ID NO 56
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 'Gly Gly Gly
      Gly Ser' repeating units
<220> FEATURE:
<223> OTHER INFORMATION: See specification as filed for detailed
      description of substitutions and preferred embodiments

<400> SEQUENCE: 56

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
        35                  40                  45

Gly Ser
    50

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Gly Gly Gly Ser Gly Gly Gly Gly Ser Gly Gly Gly Gly Ser
1               5                   10                  15

<210> SEQ ID NO 58
<211> LENGTH: 98
<212> TYPE: PRT
<213> ORGANISM: Homo sapiens

<400> SEQUENCE: 58

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
50                      55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                    85                  90                  95

Ala Lys

<210> SEQ ID NO 59
<211> LENGTH: 11
<212> TYPE: PRT
<213> ORGANISM: Homo sapiens

<400> SEQUENCE: 59

Trp Gly Gln Gly Thr Thr Val Thr Val Ser Ser
1               5                   10

<210> SEQ ID NO 60
<211> LENGTH: 102
<212> TYPE: PRT
<213> ORGANISM: Homo sapiens

<400> SEQUENCE: 60

Gln Ala Val Leu Thr Gln Pro Ala Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
            35                  40                  45

Leu Leu Arg Tyr Lys Ser Asp Ser Asp Lys Gln Gln Gly Ser Gly Val
50                      55                  60

Pro Ser Arg Phe Ser Gly Ser Lys Asp Ala Ser Ala Asn Ala Gly Ile
65                      70                  75                  80

Leu Leu Ile Ser Gly Leu Gln Ser Glu Asp Glu Ala Asp Tyr Tyr Cys
                    85                  90                  95

Met Ile Trp His Trp Val
            100

<210> SEQ ID NO 61
<211> LENGTH: 10
<212> TYPE: PRT
<213> ORGANISM: Homo sapiens

<400> SEQUENCE: 61

Phe Gly Gly Gly Thr Lys Leu Thr Val Leu
1               5                   10
```

ANTIBODIES TO ALPHA-SYNUCLEIN AND USES THEREOF

CROSS-REFERENCES TO RELATED APPLICATIONS

This application is a continuation of U.S. application Ser. No. 16/170,468, filed Oct. 25, 2018 (now U.S. Pat. No. 10,889,639), which is a continuation of U.S. application Ser. No. 15/611,416, filed Jun. 1, 2017 (now U.S. Pat. No. 10,160,800), which claims the benefit of priority from U.S. Provisional Application No. 62/344,746, filed Jun. 2, 2016. The foregoing applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 24, 2018, is named 1848081-0002-091-103_SL.txt and is 45,626 bytes in size.

BACKGROUND

The present invention relates to α-synuclein antibodies and their use in the prevention or treatment of disease, in particular alpha-synucleinopathies, and more particularly Parkinson's disease (PD).

Alpha-synucleinopathies, also known as Lewy body diseases (LBDs), are a family of neurodegenerative diseases that all have at their core alpha-synuclein as the key pathological hallmark (Jellinger, Mov Disord (2003), 18 Suppl 6: S2-12; and Spillantini and Goedert, Ann N Y Acad Sci (2000), 920: 16-27; both of which are incorporated herein by reference). Alpha-synucleinopathies include Parkinson's disease (PD), dementia with Lewy bodies (DLB) and multiple system atrophy (MSA).

PD is a slowly progressive age-related movement disorder affecting greater than 1% of people over 65 years old. PD is the second most common neurodegenerative condition after Alzheimer's disease.

A defining hallmark pathology of alpha-synucleinopathies are Lewy bodies and Lewy neurites, which are insoluble inclusions of aggregated proteins found inside neurons of the brain revealed upon post-mortem histopathological examination.

The presence of Lewy pathology and neuronal loss in non-motor brain regions such as the basal forebrain, mesopontine system, amygdala, neocortex, dorsal motor nucleus of the vagus nerve, olfactory bulbs, locus coeruleus, and the brainstem, may cause cognitive deficits and dementia, hyposmia, sleep disturbances including rapid eye movement sleep behaviour disorder (RBD), mood disorders including depression and anxiety, autonomic dysfunction including cardiovascular and gastrointestinal problems such as constipation, and fatigue and somnolence. Some of these non-motor symptoms appear to characterise the premotor or prodromal phase of the disease (Kalia et al. Lancet (2015), 386(9996): 896-912; incorporated herein by reference).

The presence of Lewy pathology and neuronal loss in motor brain regions, including most notably the death of dopaminergic neurons in the substantia nigra, may cause resting tremor, rigidity, bradykinesia and postural instability (Spillantini and Goedert, Ann N Y Acad Sci (2000), 920: 16-27; incorporated herein by reference).

Alpha-synuclein (also called "α-synuclein" or "α-syn") protein is the major structural component of Lewy bodies and Lewy neurites. Alpha-synuclein is a small acidic protein made up of 140 amino acids (14 kDa). Human natural wild-type alpha-synuclein has the amino acid sequence SEQ ID NO: 1 as described under UniProtKB accession number P37840. Unless otherwise apparent from the context, reference to alpha-synuclein or its fragments includes the natural human wild-type amino acid sequence indicated above, and human allelic variants thereof, in particular those associated with Lewy body disease (e.g., E46K, A30P, H50Q, G51D and A53T, where the first letter indicates the amino acid in SEQ ID NO: 1, the number is the codon position in SEQ ID NO: 1, and the second letter is the amino acid in the allelic variant). Such variants can optionally be present individually or in any combination. The induced mutations E83Q, A90V, A76T, which enhance alpha-synuclein aggregation, can also be present individually or in combination with each other and/or with human allelic variants E46K, A30P, H50Q, G51D and A53T. At the structural level, alpha-synuclein contains three distinct regions: an amphipathic N-terminal alpha-helix domain that has lipid and membrane binding properties (residues 1-60), a central hydrophobic amyloid-binding domain that encodes the non-amyloid-beta component (NAC) of plaques (residues 61-95), and an acidic proline-rich C-terminal tail (residues 96-140). Residues 71-82 of the NAC domain are believed to be key to the aggregation/fibrillation properties of alpha-synuclein by enabling the protein to switch from a random coil structure to a beta-sheet structure (Bisaglia et al. FASEB J (2009), 23(2): 329-40; incorporated herein by reference). Although the C-terminal domain is free of significant secondary structure it contains a key phosphorylation site at residue Ser129 and a number of tyrosine residues that are nitrated in cytosolic alpha-synuclein inclusions. N-terminal and C-terminal truncated forms of alpha-synuclein also exist. Post-translational modifications to the protein can affect alpha-synuclein aggregation and toxicity (Oueslati et al. Prog Brain Res (2010), 183: 115-45; incorporated herein by reference).

Alpha-synuclein is abundant in the central nervous system (CNS)/brain where it is found both intracellularly in neurons and glia and also extracellularly in cerebrospinal fluid (CSF) (Mollenhauer et al. J Neural Transm (2012), 119(7): 739-46; incorporated herein by reference) and the interstitial fluid (ISF) that bathes and surrounds the cells of the brain (Emmanouilidou et al. PLoS One (2011), 6(7): e22225; incorporated herein by reference). Alpha-synuclein is a synaptic protein predominantly expressed in neurons of the neocortex, hippocampus, substantia nigra, thalamus, and cerebellum (Iwai et al. Neuron (1995), 14: 467-475; incorporated herein by reference). Under physiological conditions, it is located in neuronal synaptic terminals and is specifically up-regulated at presynaptic terminals during acquisition-related synaptic rearrangement (Fortin et al. J Neurosci (2005), 25: 10913-10921; incorporated herein by reference).

In-vitro studies have shown that alpha-synuclein monomers may form the starting point for the aggregation process. The monomer can aggregate into a variety of small oligomeric species that are then stabilised by beta-sheet interactions, going on to form protofibrils which can polymerise into insoluble fibrillary structures reminiscent of those identified in Lewy bodies (Cremades et al. Cell (2012), 149(5): 1048-59; incorporated herein by reference).

Under pathological conditions, aberrant alpha-synuclein aggregation may be key to the pathological changes seen in alpha-synucleinopathies (Lashuel et al. Nature (2002), 418: 291; and Tsigelny et al. FEBS Journal (2007), 274: 1862-1877; both of which are incorporated herein by reference). In vitro and in vivo studies have shown that the neurotoxic effects of alpha-synuclein appear to be elicited by small soluble oligomeric conformers or protofibrils (Winner et al. Proc Natl Acad Sci USA (2011), 108(10): 4194-9; and Danzer et al. J Neurosci (2007), 27(34): 9220-32; both of which are incorporated herein by reference). While fibrillar aggregates of alpha-synuclein are characteristic of PD, oligomeric forms of alpha-synuclein are the toxic species (Danzer et al. J Neurosci (2007), 27(34): 9220-32; Lashuel et al. Nature (2002), 418: 291; and Winner et al. Proc Natl Acad Sci USA (2011), 108: 4194-4199; each of which are incorporated herein by reference).

Alpha-synuclein oligomers can be released to the extracellular environment and taken up by neighboring cells in a "propagation" mechanism (Angot and Brundin, Parkinsonism Relat Disord (2009), 15 Suppl 3: S143-147; Desplats et al. Proc Natl Acad Sci USA (2009), 106: 13010-13015; and Lee et al. J Biol Chem (2010), 285: 9262-9272; each of which are incorporated herein by reference). Aggregates of alpha-synuclein can propagate misfolding through a prion-like spreading mechanism (Lee et al. Nat Rev Neurol (2010), 6: 702-706; Luk et al. J Exp Med (2012), 209(5): 975-86; and Luk et al. Science (2012), 338(6109): 949-53; each of which are incorporated herein by reference). Alpha-synuclein can therefore induce neurodegeneration by either oligomer toxicity or propagation and prion-like spreading.

It is now well established and accepted that cells including neurons can secrete various forms of alpha-synuclein (monomers, oligomers, aggregates) under normal conditions and also under conditions of cellular stress, the secretion of monomeric and aggregated forms of alpha-synuclein is elevated under conditions of cellular stress, and through this release of alpha-synuclein into the extracellular milieu, pathological transmissible forms of alpha-synuclein may be propagated between neurons (Recasens and Dehay, Front Neuroanat (2014), 8: 159; incorporated herein by reference).

The effects of alpha-synuclein in PD may extend beyond the immediate damage to vulnerable neuronal cells. Like most neurodegenerative diseases there is also a pro-inflammatory cellular response observed (Lee et al. J Biol Chem (2010), 285: 9262-9272; incorporated herein by reference). Circulating alpha-synuclein and/or activated astrocytes can activate microglia, leading to increased generation of reactive oxygen species, nitric oxide and cytokine production, and further exacerbating neurodegeneration (Lee et al. J Biol Chem (2010), 285: 9262-9272; incorporated herein by reference).

A variety of different experimental models have demonstrated cell-to-cell transmission of alpha-synuclein in cultured cells, or in vivo spreading and propagation of alpha-synuclein pathologies. Lewy body pathology has been observed within embryonic mesencephalic neuronal grafts more than 10 years after the grafts were therapeutically transplanted into the striatum of PD patients. Specifically, grafted neurons contained a number of Lewy body-like inclusions that stained positively for alpha-synuclein, indicating that host-to-graft transmission of alpha-synuclein pathology had occurred (Li et al. Nat Med (2008), 14(5): 501-3; and Kordower et al. Nat Med (2008), 14(5): 504-6; both of which are incorporated herein by reference).

Further, preformed recombinant alpha-synuclein fibrils and alpha-synuclein oligomers can be internalised by cultured cells and neurons, and the direct transfer of alpha-synuclein from donor to recipient cells with the formation of alpha-synuclein inclusions similar to Lewy pathology has been demonstrated (Danzer et al. J Neurosci (2007), 27(34): 9220-32; Volpicelli-Daley et al. Neuron (2011), 72(1): 57-71; and Luk et al. Proc Natl Acad Sci USA (2009), 106(47): 20051-6; each of which are incorporated herein by reference). Injection of preformed synthetic alpha-synuclein fibrils or Lewy body-like alpha-synuclein containing material extracted from the brains of aged alpha-synuclein transgenic mice into the brains of asymptomatic recipient mice promotes the formation of Lewy body-like pathology in host neurons of the recipient animals along with neurodegeneration and neurological deficits (Luk et al. J Exp Med (2012), 209(5): 975-86; and Luk et al. Science (2012), 338(6109): 949-53; both of which are incorporated herein by reference). Alpha-synuclein containing Lewy body extracts isolated from PD brains inoculated into the substantia nigra or striatum of macaque monkeys and mice is rapidly taken up by host cells (within 24 hours) followed by a slower loss of striatal dopaminergic terminals, with cell loss evident after more than a year (Recasens et al. Ann Neurol (2014), 75(3): 351-62; incorporated herein by reference). Similarly, inoculation of mice with brain homogenates derived from patients with the synucleinopathies DLB or MSA triggers alpha-synuclein Lewy-like pathology in the host mice (Watts et al. Proc Natl Acad Sci USA (2013), 110(48): 19555-60; and Masuda-Suzukake et al. Brain (2013), 136 (Pt 4): 1128-38; both of which are incorporated herein by reference). Finally, transfer and transmission of both monomeric and oligomeric alpha-synuclein from the olfactory bulb to interconnected brain structures has been demonstrated in mice (Rey et al. Acta Neuropathol (2013), 126(4): 555-73; incorporated herein by reference).

Passive immunotherapy approaches with antibodies targeting alpha-synuclein have been tested in numerous preclinical alpha-synucleinopathy mouse models (Lawand et al. Expert Opin Ther Targets (2015): 1-10; incorporated herein by reference). Specifically, a study using a monoclonal antibody directed against alpha-synuclein (9E4) has shown in vivo clearance of alpha-synuclein aggregates and pathology, behavioural motor improvements, and neuroprotective effects (WO 2014/058924; which is incorporated herein by reference).

Further studies using passive immunisation of alpha-synuclein transgenic mice developed as experimental models of PD/DLB, with the 9E4 monoclonal antibody have shown the antibody to clear alpha-synuclein pathology, decrease synaptic and axonal deficits, abrogate loss of striatal tyrosine hydroxylase fibres, and significantly reduce memory deficits and motor function impairments (Games et al. J Neurosci (2014), 34(28): 9441-54; Bae et al. J Neurosci (2012), 32(39): 13454-69; and Masliah et al. PLoS One (2011), 6(4): e19338; each of which are incorporated herein by reference). Further it has been demonstrated that passive administration of anti-alpha-synuclein monoclonal antibodies in wild-type mice that were injected intrastriatally with synthetic alpha-synuclein preformed fibrils (pffs) led to robust reduction in Lewy pathology, prevention of dopamine neuron loss in the substantia nigra, and a significant improvement in motor impairments that are manifest in the mouse model after pffs treatment (Tran et al. Cell Rep (2014), 7(6): 2054-65; incorporated herein by reference).

Additionally, one of the major challenges associated with treating disorders of the CNS with large molecule therapeutics, such as antibodies, is getting these drugs into the affected tissue. The passage of large molecules into the brain and spinal cord is largely restricted by the blood-brain barrier (BBB). The BBB protects and regulates the homeostasis of the brain and prevents the free passage of molecules into most parts of the brain, thereby limiting the treatment of many brain diseases. Transport of essential molecules such as nutrients, growth factors, and hormones is achieved via a series of specific transporters and receptors that regulate passage across the brain endothelial cells. The delivery of biologics and other drugs to the brain therefore represents a significant challenge. Additionally, transport mechanisms appear to exist that rapidly remove antibodies from the brain, presumably to prevent inflammatory responses due to engagement of Fc with effector ligands that promote a pro-inflammatory response.

Over the last decade, reports of antibody transport across the BBB have emerged where binding to the extracellular domain of the transporter molecules facilitates transcytosis of the receptor antibody complex across the endothelial cell layer.

The BBB is mainly comprised of brain capillary endothelial cells, which have specialized characteristics, such as tight junctions, to limit transport of molecules into the brain (Reese et al. 1967, J. Cell Biol. 34: 207-217; Brightman et al. 1969, J. Cell Biol. 40: 648-677; Rubin et al. 1999, Ann. Rev. Neurosci. 22: 11-28), although other cell types, such as pericytes, astrocytes, and neuronal cells, also play an important role in the function of the BBB. Typically, less than 0.1% of a peripherally dosed antibody reaches the brain (Boado et al. 2010, Mol. Pharm. 7: 237-244; Pepinsky et al. 2011, Nat. Neurosci. 8: 745-751). The BBB functions as a physical, metabolic and immunological barrier (Gaillard et al. 2003, Microvasc. Res. 65: 24-31).

Antibody transport across the BBB can be enhanced by triggering receptor mediated transcytosis on brain endothelial cells. Through this process, engagement of antigens on the luminal side of the endothelial cell can induce the internalization and shuttling of the antibody across the cell, and then its subsequent release into the tissue.

Current drug therapies for PD are mainly focused on treating the motor-related symptoms of the disease. There are currently no marketed or available therapies that can treat or prevent alpha-synucleinopathy.

Accordingly, there is a need in the art for a therapy for treating alpha-synucleinopathies, particularly in humans.

SUMMARY OF THE INVENTION

The present invention is concerned with isolated antibodies to human alpha-synuclein. The invention provides antibodies or antigen-binding fragments thereof that have one or more of the functional properties of the aslo0452 ngl-3 antibody. For example:

The invention provides an antibody or antigen-binding fragment thereof that specifically binds the C-terminal region of human α-synuclein. The invention provides an antibody or antigen-binding fragment thereof that specifically binds the region comprising about amino acid 102 to about amino acid 130 of human α-synuclein (e.g., SEQ ID NO: 1). In some embodiments, the antibody or antigen-binding fragment thereof specifically binds to a region comprising about amino acid 120 to about amino acid 130 of human α-synuclein (SEQ ID NO: 1). In some embodiments, the antibody or antigen-binding fragment thereof binds to an epitope that is not the same as the antibody bound by the 9E4 antibody.

The invention provides an antibody or antigen-binding fragment thereof that binds human α-synuclein but not human β-synuclein or human γ-synuclein.

The invention provides an antibody or antigen-binding fragment thereof that binds to human, rat and cynomolgus α-synuclein.

The invention provides an antibody or antigen-binding fragment thereof that binds to human α-synuclein with high affinity. In one embodiment, the antibody, or antigen-binding fragment thereof, of the invention binds to alpha-synuclein with a $K_D$ of less than 500 picoMolar (pM), less than 400 pM, less than 300 pM, less than 200 pM, less than 150 pM, less than 120 pM, less than 110 pM or 106 pM or less as measured for example using Octet analysis. In one embodiment, the antibody, or antigen-binding fragment thereof, of the invention binds to alpha-synuclein with a $K_D$ of less than 400 picoMolar (pM), less than 300 pM, less than 250 pM, less than 200 pM, less than 150 pM, less than 120 pM, less than 110 pM, less than 100 pM, less than 80 pM or 74 pM or less as measured for example using KinExA analysis.

The invention provides an antibody or antigen-binding fragment thereof that binds to native endogenous human α-synuclein.

The invention provides an antibody or antigen-binding fragment thereof that binds to monomeric forms of human α-synuclein.

The invention provides an antibody or antigen-binding fragment thereof that binds to aggregates of human α-synuclein.

The invention provides an antibody or antigen-binding fragment thereof that binds disease relevant, pathological forms of α-synuclein.

The invention provides an antibody or antigen-binding fragment thereof of the invention that reduces α-synuclein levels in the brain interstitial fluid. In particular, the antibody or antigen-binding fragment thereof according to the invention reduces free unbound α-synuclein levels in the brain interstitial fluid.

The invention provides an antibody or antigen-binding fragment thereof of the invention that reduces α-synuclein levels in the cerebrospinal fluid. In particular, the antibody or antigen-binding fragment thereof according to the invention reduces free unbound α-synuclein levels in the cerebrospinal fluid.

As used herein, the terms "free unbound α-synuclein" refer to α-synuclein that is not bound to the antibody or antigen-binding fragment thereof according to the invention. Said free unbound α-synuclein can apply to α-synuclein in its monomeric or oligomeric form, or in aggregated form. These terms generally apply to any pathologic form of α-synuclein.

The invention provides an antibody or antigen-binding fragment thereof that reduces α-synuclein spreading in vivo.

In one embodiment, the antibody or antigen-binding fragment thereof of the present invention competes with antibody aslo0452 ngl-3 for binding to human α-synuclein.

In one embodiment, the antibody or antigen-binding fragment thereof of the present invention binds to the same epitope on human α-synuclein as antibody aslo0452 ngl-3.

In one embodiment, the antibody or antigen-binding fragment thereof of the present invention derives from antibody asyn0087 comprising a variable heavy chain region (VH) of amino acid sequence of SEQ ID NO: 2 and a variable light chain region (VL) of amino acid sequence SEQ ID NO: 3, as disclosed herewith.

In a particular embodiment, the antibody or antigen-binding fragment thereof of the present invention derives from antibody asyn0087, wherein said antibody or antigen-binding fragment has a $K_D$ of less than 500 mM and binds the same epitope as any one of antibodies asyn0087, aslo0452 ngl-3 and aslo0543, described herewith.

As used herewith, "H-CDR" stands for a complementary determining region (CDR) on the heavy chain region, and "L-CDR" stands for a complementary determining region (CDR) on the light chain region of an antibody or antigen-binding fragment thereof.

In one embodiment, the antibody or antigen-binding fragment thereof according to the invention comprises at least one CDR selected from:
(i) H-CDR1 of SEQ ID NO: 5,
(ii) H-CDR2 of SEQ ID NO: 6,
(iii) H-CDR3 of SEQ ID NO: 7,
(iv) L-CDR1 of SEQ ID NO: 9,
(v) L-CDR2 of SEQ ID NO: 10,
(vi) L-CDR3 of SEQ ID NO: 11.

In a further embodiment, the CDR3 of the heavy chain of the antibody or antigen-binding fragment thereof according to the invention is CDR3 of SEQ ID NO: 16 of the heavy chain of antibody aslo0452 ngl-3; and/or the CDR3 of the light chain of the antibody or antigen-binding fragment thereof according to the invention is CDR3 of SEQ ID NO: 21 of the light chain of antibody aslo0452 ngl-3.

In one embodiment, the antibody or antigen-binding fragment thereof of the present invention has at least one, at least two, at least three, at least four, at least five or all of the CDRs selected from the CDRs of antibody aslo0452 ngl-3, i.e. at least one CDR selected from any one of SEQ ID NO: 5, SEQ ID NO: 15, SEQ ID NO: 16, SEQ ID NO: 20, SEQ ID NO: 10, SEQ ID NO: 21.

In one embodiment, the CDR3 of the heavy chain of the antibody or antigen-binding fragment thereof of the present invention is CDR3 of the heavy chain of antibody aslo0452 ngl-3; and/or the CDR3 of the light chain of the antibody or antigen-binding fragment thereof of the present invention is CDR3 of the light chain of antibody aslo0452 ngl-3.

In one embodiment, the CDR3 of the heavy chain of the antibody or antigen-binding fragment thereof of the present invention is CDR3 of the heavy chain of antibody aslo0452 ngl-3.

In one embodiment, the CDR3 of the light chain of the antibody or antigen-binding fragment thereof of the present invention is CDR3 of the light chain of antibody aslo0452 ngl-3.

In one embodiment, the CDR3 of the heavy chain of the antibody or antigen-binding fragment thereof of the present invention is CDR3 of the heavy chain of antibody aslo0452 ngl-3 and the CDR3 of the light chain of the antibody or antigen-binding fragment thereof of the present invention is CDR3 of the light chain of antibody aslo0452 ngl-3.

The present invention provides an antibody or antigen-binding fragment thereof having the six CDRs of antibody aslo0452 ngl-3.

Thus, in one embodiment, the antibody, or antigen-binding fragment thereof according to the invention comprises:
a) three heavy chain CDRs having sequences:
  (i) H-CDR1 of SEQ ID NO: 5,
  (ii) H-CDR2 of SEQ ID NO: 15; and
  (iii) H-CDR3 of SEQ ID NO: 16, and
b) three light chain CDRs having sequences:
  (i) L-CDR1 of SEQ ID NO: 20,
  (ii) L-CDR2 of SEQ ID NO: 10, and
  (iii) L-CDR3 of SEQ ID NO: 21.

The present invention provides an antibody or antigen-binding fragment thereof of the present invention comprising a variable heavy chain having at least 80%, 85%, 90%, 95%, 96%, 97%, 98%, 99%, or 100% identity to the nucleotide sequence defined by SEQ ID NO: 13 and a variable light chain having at least 80%, 85%, 90%, 95%, 96%, 97%, 98%, 99%, or 100% identity to the nucleotide sequence defined by SEQ ID NO: 18.

The present invention provides an antibody or antigen-binding fragment thereof of the present invention comprising a variable heavy chain having at least 80%, 85%, 90%, 95%, 96%, 97%, 98%, 99%, or 100% identity to the amino acid sequence defined by SEQ ID NO: 14 and a variable light chain having at least 80%, 85%, 90%, 95%, 96%, 97%, 98%, 99%, or 100% identity to the amino acid sequence defined by SEQ ID NO: 19.

The present invention provides an antibody or antigen-binding fragment thereof of the present invention comprising a variable heavy chain having the amino acid sequence of SEQ ID NO: 14 and a variable light chain having the amino acid sequence of SEQ ID NO: 19.

In a particular embodiment, the antibody or antigen-binding fragment thereof according to the invention comprises a variable heavy chain having a sequence defined by SEQ ID NO: 4 and a variable light chain having a sequence defined by SEQ ID NO: 8.

In a further particular embodiment, the antibody or antigen-binding fragment thereof according to the invention comprises a variable heavy chain having a sequence defined by SEQ ID NO: 4 and a variable light chain having a sequence defined by SEQ ID NO: 8, and binds to human α-synuclein with a $K_D$ of less than 500 pM and binds the same epitope as asyn0087, aslo0452 ngl-3 or aslo0543.

In another embodiment, the antibody or antigen-binding fragment thereof according to the invention comprises a variable heavy chain having at least 80%, 85%, 90%, 95%, 96%, 97%, 98%, 99%, or 100% identity to the sequence defined by SEQ ID NO: 14 and a variable light chain having at least 80%, 85%, 90%, 95%, 96%, 97%, 98%, 99%, or 100% identity to the sequence defined by SEQ ID NO: 19.

In a particular embodiment, the antibody or antigen-binding fragment thereof according to the invention comprises a variable heavy chain having a sequence defined by SEQ ID NO: 14 and a variable light chain having a sequence defined by SEQ ID NO: 19.

In a further embodiment, the antibody, or antigen-binding fragment thereof according to the invention comprises a variable heavy chain having at least 80%, 85%, 90%, 95%, 96%, 97%, 98%, 99%, or 100% identity to the sequence defined by SEQ ID NO: 14 and a variable light chain having at least 80%, 85%, 90%, 95%, 96%, 97%, 98%, 99%, or 100% identity to the sequence defined by SEQ ID NO: 19 and further comprises:
a) three heavy chain CDRs having sequences:
  (i) H-CDR1 of SEQ ID NO: 5,
  (ii) H-CDR2 of SEQ ID NO: 15; and
  (iii) H-CDR3 of SEQ ID NO: 16, and
b) three light chain CDRs having sequences:
  (i) L-CDR1 of SEQ ID NO: 20,
  (ii) L-CDR2 of SEQ ID NO: 10; and
  (iii) L-CDR3 of SEQ ID NO: 21.

The present invention also provides an antibody or antigen-binding fragment thereof comprising a variable heavy chain having a nucleotide sequence defined by SEQ ID NO: 13 and a variable light chain having a nucleotide sequence defined by SEQ ID NO: 18.

The present invention provides an antibody or antigen-binding fragment thereof comprising a variable heavy chain having an amino acid sequence defined by SEQ ID NO: 14 and a variable light chain having an amino acid sequence defined by SEQ ID NO: 19.

Also provided is an antibody or antigen-binding fragment thereof of the present invention comprising a heavy chain having an amino acid sequence defined by SEQ ID NO: 12 and a light chain having an amino acid sequence defined by SEQ ID NO: 17.

In another embodiment, the antibody or antigen-binding fragment thereof according to the invention comprises a variable heavy chain having at least 80%, 85%, 90%, 95%, 96%, 97%, 98%, 99%, or 100% identity to the sequence defined by SEQ ID NO: 24 and a variable light chain having at least 80%, 85%, 90%, 95%, 96%, 97%, 98%, 99%, or 100% identity to the sequence defined by SEQ ID NO: 30.

In a particular embodiment, the antibody or antigen-binding fragment thereof according to the invention comprises a variable heavy chain having a sequence defined by SEQ ID NO: 24 and a variable light chain having a sequence defined by SEQ ID NO: 30.

In a further embodiment, the antibody, or antigen-binding fragment thereof according to the invention comprises a variable heavy chain having at least 80%, 85%, 90%, 95%, 96%, 97%, 98%, 99%, or 100% identity to the sequence defined by SEQ ID NO: 24 and a variable light chain having at least 80%, 85%, 90%, 95%, 96%, 97%, 98%, 99%, or 100% identity to the sequence defined by SEQ ID NO: 30 and further comprises:
  c) three heavy chain CDRs having sequences:
    (iv) H-CDR1 of SEQ ID NO: 25,
    (v) H-CDR2 of SEQ ID NO: 26; and
    (vi) H-CDR3 of SEQ ID NO: 27, and
  d) three light chain CDRs having sequences:
    (iv) L-CDR1 of SEQ ID NO: 31,
    (v) L-CDR2 of SEQ ID NO: 32; and
    (vi) L-CDR3 of SEQ ID NO: 33.

The present invention also provides an antibody or antigen-binding fragment thereof comprising a variable heavy chain having a nucleotide sequence defined by SEQ ID NO: 24 and a variable light chain having a nucleotide sequence defined by SEQ ID NO: 30.

The present invention provides an antibody or antigen-binding fragment thereof comprising a variable heavy chain having an amino acid sequence defined by SEQ ID NO: 24 and a variable light chain having an amino acid sequence defined by SEQ ID NO: 30.

Also provided is an antibody or antigen-binding fragment thereof of the present invention comprising a heavy chain having an amino acid sequence defined by SEQ ID NO: 22 and a light chain having an amino acid sequence defined by SEQ ID NO: 28.

In one embodiment, the antibody or antigen-binding fragment thereof of the present invention as defined anywhere above is an IgA, IgD, IgE, IgM, IgG such as IgG1, IgG2, IgG3, or IgG4 antibody or antigen-binding fragment thereof.

In another embodiment, the antibody or antigen-binding fragment thereof of the present invention has a modified Fc region. Suitable modifications are well known to those skilled in the art and may include inter alia modifications to increase or decrease half-life, ablate, reduce or enhance effector function, provide substituted cysteines with free thiols for conjugation. Examples of such modifications are YTE to increase half-life and/or TM to reduce effector function. In some embodiments, any of the antibodies or antigen-binding fragments disclosed herein comprise mutations M252Y/S254T/T256E (YTE) in the Fc region of the antibody (Dall' Acqua et al., 2006, J. Biol. Chem, 281: 23514-23524). In some embodiments, any of the antibodies or antigen-binding fragments disclosed herein comprise a triple mutation (abbreviated herein as "TM") in the Fc region corresponding to the L234F/L235E/P331S mutation disclosed in Oganesyan et al. Acta Crystallogr D Biol Crystallogr, (2008) 64: 700-704. In an embodiment the antibody or antigen-binding fragment thereof of the present invention may be an IgG1 TM antibody or antigen-binding fragment thereof. In another embodiment the antibody or antigen-binding fragment thereof of the present invention may comprise a Fc region having YTE mutations.

In another embodiment the antibody, or antigen-binding fragment thereof, of the present invention may be coupled to a blood-brain barrier (BBB) transporter moiety, wherein the BBB transporter moiety is capable of transporting the antibody, or antigen binding fragment thereof, across the BBB.

In an embodiment the BBB transporter moiety may be an antibody. In an embodiment the BBB antibody may form a multispecific construct with an anti-α-synuclein antibody or antigen binding fragment thereof. The BBB transporter moiety may comprise an immunoglobulin variable heavy chain complementarity-determining region-1 (VH-CDR1), an immunoglobulin variable heavy chain complementarity-determining region-2 (VH-CDR2), an immunoglobulin variable heavy chain complementarity-determining region-3 (VH-CDR3), an immunoglobulin variable light chain complementarity-determining region-1 (VL-CDR1), an immunoglobulin variable light chain complementarity-determining region-2 (VL-CDR2), and an immunoglobulin variable light chain complementarity-determining region-3 (VL-CDR3); wherein the VH-CDR1 comprises SEQ ID NO. 40 or 49, VH-CDR2 comprises SEQ ID NO. 41 or 50, VH-CDR3 comprises SEQ ID NO. 42 or 51, VL-CDR1 comprises SEQ ID NO. 36, 44 or 53, VL-CDR2 comprises SEQ ID NO. 37, 45 or 54 and VL-CDR3 comprises SEQ ID NO. 38, 46 or 55.

In some embodiments, the transporter moiety comprises an immunoglobulin variable heavy chain (VH) region comprising SEQ ID NO: 47 or SEQ ID NO: 39. In some embodiments, the transporter moiety comprises an immunoglobulin variable light chain (VL) region comprising SEQ ID NO: 43.

Additionally, the transporter moiety can be selected from a complete antibody, an Fv fragment, a Fab fragment, a Fab' fragment, a F(ab')2 fragment, a disulfide-linked (dsFv) fragment, a single chain Fv (scFV) fragment, an sc(Fv)2 fragment, a diabody, a triabody, a tetrabody, a minibody, and a single chain antibody. In a particular embodiment, the transporter moiety comprises an scFV fragment comprising a VH domain and a VL domain fused together via a linker. In some instances, the linker can be (Gly4Ser)$^n$ (SEQ ID NO: 56), wherein n is a positive integer selected from the group consisting of 1, 2, 3, 4, 5, 6, 7, 8, 9 and 10.

In some embodiments, any transporter molecule of the invention can be combined as described herein with any alpha-synuclein binding molecule of the invention to provide a multi-specific binding molecule of the invention.

The invention provides the antibody or antigen-binding fragment thereof of the present invention as defined anywhere above, for use as a medicament.

The invention also provides the antibody or antigen-binding fragment thereof of the present invention as defined anywhere above for use in the prevention or treatment of an α-synucleinopathy.

In one embodiment, the α-synucleinopathy is selected from Parkinson's disease (PD), dementia with Lewy bodies (DLB), and multiple system atrophy (MSA).

In one embodiment, the α-synucleinopathy is Parkinson's disease (PD).

The invention provides a method of treating or preventing a disease, in particular a disease associated with the central nervous system, in a patient, the method comprising administering to the patient the antibody or antigen-binding fragment thereof of the present invention as defined anywhere above.

In one embodiment, the disease is an α-synucleinopathy.

In one embodiment, the α-synucleinopathy is selected from Parkinson's disease (PD), dementia with Lewy bodies (DLB), and multiple system atrophy (MSA).

In one embodiment, the α-synucleinopathy is Parkinson's disease (PD).

The invention provides a pharmaceutical composition comprising the antibody or antigen-binding fragment thereof of the present invention as defined anywhere above, and a pharmaceutically acceptable excipient.

The phrase "pharmaceutically acceptable excipient" includes any and all solvents, dispersion media, coatings, antibacterial agents and antifungal agents, isotonic agents, and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions. The pharmaceutical compositions may also be included in a container, pack, or dispenser together with instructions for administration.

A pharmaceutical composition of the invention is formulated to be compatible with its intended route of administration. Methods to accomplish the administration are known to those of ordinary skill in the art. The administration may, for example, be intravenous, intraperitoneal, intramuscular, intracavity, subcutaneous or transdermal.

The invention provides an isolated nucleic acid molecule encoding the antibody or antigen-binding fragment thereof of the present invention as defined anywhere above.

In a particular embodiment, the present invention provides an isolated nucleic acid molecule comprising SEQ ID NO: 13 and/or SEQ ID NO: 18.

In another particular embodiment, the present invention provides an isolated nucleic acid molecule comprising SEQ ID NO: 23 and/or SEQ ID NO: 29.

Once provided with this information, one of skill in the art could readily obtain nucleic acid molecules encoding the disclosed antibodies or antigen-binding fragments thereof. The nucleic acids may comprise DNA or RNA and may be wholly or partially synthetic or recombinant. Reference to a nucleotide sequence encompasses a DNA molecule with the specified sequence, and encompasses a RNA molecule with the specified sequence in which U is substituted for T, unless context requires otherwise.

The nucleic acids molecules of the invention comprise a coding sequence for a CDR, a VH domain, and/or a VL domain disclosed herein.

The present disclosure also provides constructs in the form of plasmids, vectors, phagemids, transcription or expression cassettes which comprise at least one nucleic acid molecule encoding the antibody or antigen-binding fragment thereof of the present invention as defined anywhere above, in particular encoding a CDR, a VH domain, and/or a VL domain disclosed herein.

The disclosure further provides a host cell which comprises one or more constructs as above.

Also provided are nucleic acids encoding any one or more CDR (H-CDR1, H-CDR2, H-CDR3, L-CDR1, L-CDR2, or L-CDR3), VH or VL domain disclosed herein, as well as methods of making of the encoded products. The method comprises expressing the encoded product from the encoding nucleic acid. Expression may be achieved by culturing under appropriate conditions recombinant host cells containing the nucleic acid. Following production by expression a VH or VL domain, or specific binding member may be isolated and/or purified using any suitable technique, then used as appropriate.

Antigen-binding fragments, VH and/or VL domains and encoding nucleic acid molecules and vectors may be isolated and/or purified from their natural environment, in substantially pure or homogeneous form, or, in the case of nucleic acid, free or substantially free of nucleic acid or genes of origin other than the sequence encoding a polypeptide with the required function.

Systems for cloning and expression of a polypeptide in a variety of different host cells are well known in the art. For cells suitable for producing antibodies, see Gene Expression Systems, Academic Press, eds. Fernandez et al., 1999. Briefly, suitable host cells include bacteria, plant cells, mammalian cells, and yeast and baculovirus systems. Mammalian cell lines available in the art for expression of a heterologous polypeptide include Chinese hamster ovary cells, HeLa cells, baby hamster kidney cells, NS0 mouse myeloma cells, and many others. A common bacterial host is *E. coli*. Any protein expression system compatible with the invention may be used to produce the disclosed antibodies. Suitable expression systems include transgenic animals described in Gene Expression Systems, Academic Press, eds. Fernandez et al., 1999.

Suitable vectors can be chosen or constructed, so that they contain appropriate regulatory sequences, including promoter sequences, terminator sequences, polyadenylation sequences, enhancer sequences, marker genes and other sequences as appropriate. Vectors may be plasmids or viral, e.g., phage, or phagemid, as appropriate. For further details see, for example, Sambrook et al., Molecular Cloning: A Laboratory Manual, 2nd ed., Cold Spring Harbor Laboratory Press, 1989. Many known techniques and protocols for manipulation of nucleic acid, for example, in preparation of nucleic acid constructs, mutagenesis, sequencing, introduction of DNA into cells and gene expression, and analysis of proteins, are described in detail in Current Protocols in Molecular Biology, 2nd Edition, eds. Ausubel et al., John Wiley & Sons, 1992.

A further aspect of the disclosure provides a host cell comprising a nucleic acid as disclosed here, in particular a vector comprising a nucleic acid molecule encoding the antibody or antigen-binding fragment thereof of the present invention as defined anywhere above.

A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, electroporation and transfection using bacteriophage. The introduction of the nucleic acid into the cells may be followed by causing or allowing expression from the nucleic acid, e.g., by culturing host cells under conditions for expression of the gene.

BRIEF DESCRIPTION OF THE FIGURES AND SEQUENCE LISTING

The present invention will now be described in more detail with reference to the attached Figures and sequence listing, in which are shown:

Key to SEQ ID NOs:

TABLE 1

Affinity determination of key anti-α-synuclein antibodies for human α-syn performed on two affinity measurement platforms.

| Name | Description | SEQ ID NO: |
|---|---|---|
| human alpha synuclein | amino acid sequence | 1 |
| asyn0087 | VH amino acid sequence | 2 |
|  | VL amino acid sequence | 3 |
| General sequence of an antibody derived from asyn0087 | VH amino acid sequence | 4 |
|  | H-CDR1 amino acid sequence | 5 |
|  | H-CDR2 amino acid sequence | 6 |
|  | H-CDR3 amino acid sequence | 7 |
|  | VL amino acid sequence | 8 |
|  | L-CDR1 amino acid sequence | 9 |
|  | L-CDR2 amino acid sequence | 10 |
|  | L-CDR3 amino acid sequence | 11 |
| aslo0452 ngl-3 | Heavy chain amino acid sequence | 12 |
|  | VH nucleotide sequence | 13 |
|  | VH amino acid sequence | 14 |
|  | H-CDR1 amino acid sequence | 5 |
|  | H-CDR2 amino acid sequence | 15 |
|  | H-CDR3 amino acid sequence | 16 |
|  | Light chain amino acid sequence | 17 |
|  | VL nucleotide sequence | 18 |
|  | VL amino acid sequence | 19 |
|  | L-CDR1 amino acid sequence | 20 |
|  | L-CDR2 amino acid sequence | 10 |
|  | L-CDR3 amino acid sequence | 21 |
| aslo0543 | Heavy chain amino acid sequence | 22 |
|  | VH nucleotide sequence | 23 |
|  | VH amino acid sequence | 24 |
|  | H-CDR1 amino acid sequence | 25 |
|  | H-CDR2 amino acid sequence | 26 |
|  | H-CDR3 amino acid sequence | 27 |
|  | Light chain amino acid sequence | 28 |
|  | VL nucleotide sequence | 29 |
|  | VL amino acid sequence | 30 |
|  | L-CDR1 amino acid sequence | 31 |
|  | L-CDR2 amino acid sequence | 32 |
|  | L-CDR3 amino acid sequence | 33 |
| General BBB transporter | VH amino acid sequence | 34 |
|  | VL amino acid sequence | 35 |
|  | L-CDR1 amino acid sequence | 36 |
|  | L-CDR2 amino acid sequence | 37 |
|  | L-CDR3 amino acid sequence | 38 |
| BBBt0626gl | VH amino acid sequence | 39 |
|  | H-CDR1 amino acid sequence | 40 |
|  | H-CDR2 amino acid sequence | 41 |
|  | H-CDR3 amino acid sequence | 42 |
|  | VL amino acid sequence | 43 |
|  | L-CDR1 amino acid sequence | 44 |
|  | L-CDR2 amino acid sequence | 45 |
|  | L-CDR3 amino acid sequence | 46 |
| BBBt0626 | VH amino acid sequence | 47 |
|  | H-CDR1 amino acid sequence | 40 |
|  | H-CDR2 amino acid sequence | 41 |
|  | H-CDR3 amino acid sequence | 42 |
|  | VL amino acid sequence | 43 |
|  | L-CDR1 amino acid sequence | 44 |
|  | L-CDR2 amino acid sequence | 45 |
|  | L-CDR3 amino acid sequence | 46 |
| BBBt0632gl | VH amino acid sequence | 48 |
|  | H-CDR1 amino acid sequence | 49 |
|  | H-CDR2 amino acid sequence | 50 |
|  | H-CDR3 amino acid sequence | 51 |
|  | VL amino acid sequence | 52 |
|  | L-CDR1 amino acid sequence | 52 |
|  | L-CDR2 amino acid sequence | 54 |
|  | L-CDR3 amino acid sequence | 55 |

Figure legends:

FIG. 1: Schematic of HTRF® assay.

FIG. 2: Comparison of amino acid sequences of asyn0087, aslo0452ngl-3 and aslo0543 heavy chain variable region (VH) (SEQ ID NOs: 2, 14 and 24, respectively) and light chain variable region (VL) (SEQ ID NOs: 3, 19, and 30, respectively). The underlined amino acids correspond to the CDRs.

FIGS. 3A-3D: Nucleotide and Amino Acid Sequence of aslo0452 ngl-3. FIGS. 3A and 3B show the variable heavy chain and variable light chain nucleotide and amino acid sequences, respectively, of aslo0452 ngl-3. FIG. 3A discloses SEQ ID Nos: 13 and 14, respectively, in order of appearance. FIG. 3B discloses SEQ ID Nos: 18 and 19, respectively, in order of appearance. FIGS. 3C and 3D show the alignment of these sequences to the closest human germline sequences. FIG. 3C shows the alignment of aslo0452 ngl-3 variable heavy chain domain amino acid sequence (SEQ ID NO: 14) to germline IGHV3-23 (SEQ ID NO: 58) and JH6 sequences (SEQ ID NO: 59). FIG. 3D shows the alignment of aslo0452 ngl-3 variable light chain domain amino acid sequence (SEQ ID NO: 19) to germline IGLV5-45 (SEQ ID NO: 60) and JL2 (SEQ ID NO: 61), 3 sequences. The complementarity determining regions (CDRs) are underlined and labelled. Differences from the germline are highlighted in bold and outlined. All non-Vernier residues in the light chain framework regions are human germline amino acids. Vernier residues (*) have not been changed to match the germline amino acids.

Figure 4A:
Figure 4B:
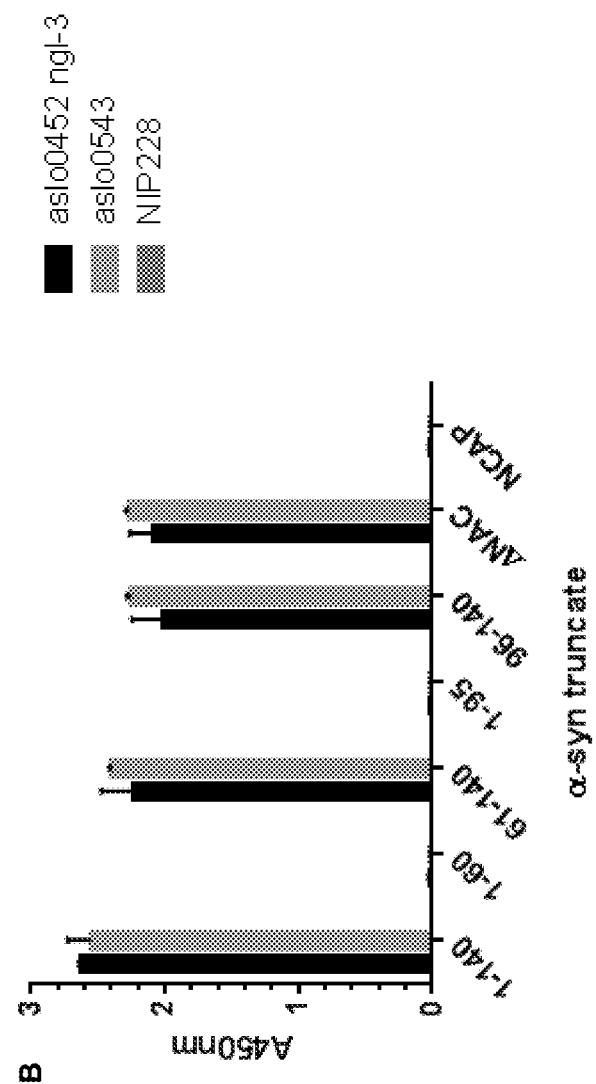

FIGS. 4A and 4B: Epitope binding of lead isolate clones using a panel of α-syn truncates. ELISA wells are coated with a range of commercially available α-syn truncates representing the various defined regions of the protein: 1-140: full length α-syn, 1-60: N-terminal region only, 61-140: non-amyloid component of plaques (NAC) plus C-terminal region, 1-95: N-terminal and NAC regions, 96-140: C-terminal region only, ANAC: NAC region deleted, NCAP: is an alternatively spliced form of α-syn missing amino acids 103-129 (rPeptide). Primary antibodies used for detection were (FIG. 4A) Asyn087; and (FIG. 4B) Aslo0452 ngl-3 (black bars), aslo0543 (light grey bars) and NIP228 isotype matched control (dark grey bars). Binding is detected with either an anti-human IgG Eu$^{3+}$ secondary antibody (FIG. 4A) or an anti-human IgG-HRP secondary antibody (FIG. 4B).

Figure 5:
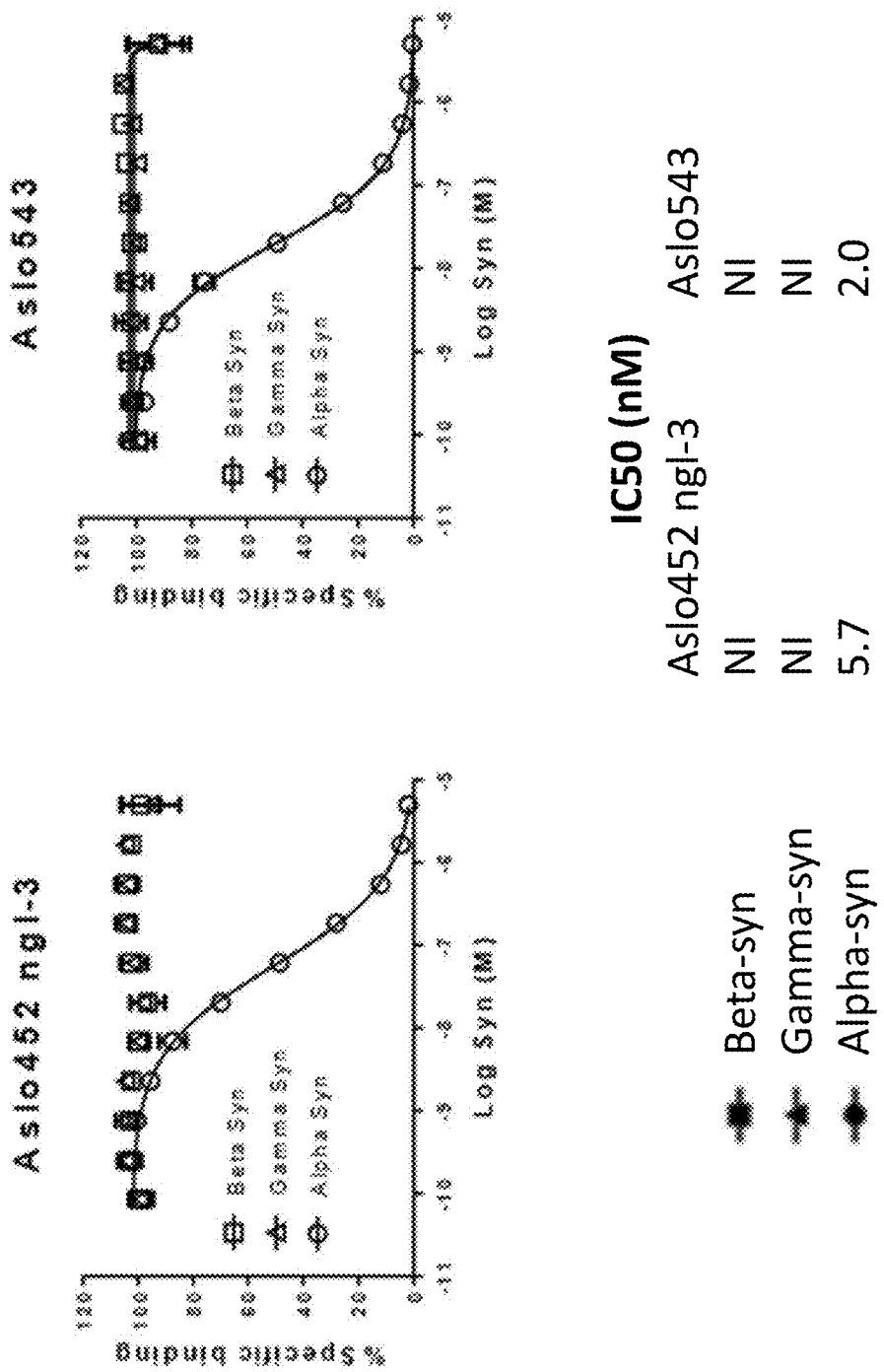

FIG. 5: Specificity of aslo0452 ngl-3 and aslo0543 for α-syn Relative to Synuclein Family Members using a DEL-FIA Epitope Competition assay. Using the epitope competition HTRF assay, the specificity of the affinity optimized aslo0452 ngl-3 and aslo0543 clones for α-syn was determined by titration of unlabeled α-syn, β-syn and γ-syn. From this $IC_{50}$ values were determined.

Figure 6:
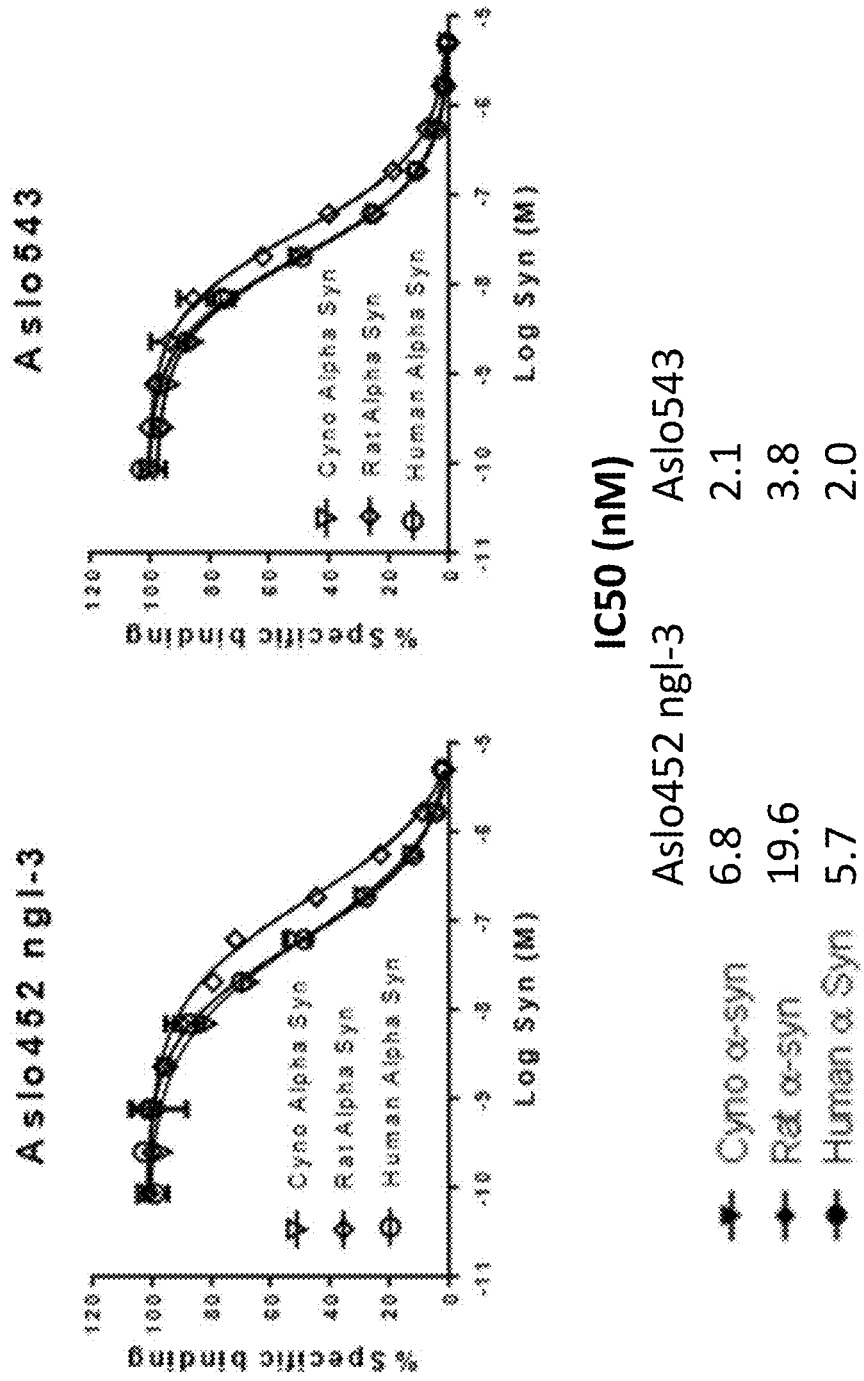

FIG. 6: Specificity of aslo0452 ngl-3 and aslo0543 for human, cynomolgus monkey and rat α-syn using a HTRF Epitope Competition assay. Using the epitope competition HTRF assay, the species cross-reactivity profile of the affinity optimized clones was determined in a similar assay by titration of unlabeled α-syn and derivation of $IC_{50}$ values for each species of α-syn.

FIGS. 7A and 7B: Representative Flow Cytometry Results demonstrating that affinity optimized clones bind to Native human α-syn in a Human neuroblastoma cell line. FIGS. 7A, 7C, 7E and 7G show binding to α-syn negative human breast cancer cell line, BT20. FIGS. 7B, 7D, 7F and 7H show binding to the α-syn positive human neuroblastoma cell line, SHSY5Y. FIGS. 7A-7D: The primary human antibodies used in this study were asyn0087 and Hu IgG control. Human antibody binding was detected using a secondary anti-Human IgG-FITC (Jackson). FIGS. 7E-7H: The primary human antibodies used in this study were aslo0452 ngl-3, aslo0543, and NIP228 isotype matched IgG1 TM control. Human antibody binding was detected using a secondary anti-Human IgG-FITC (Jackson). The primary mouse antibodies used were 4D6 (Covance), and an isotype matched negative control (R&D Systems). Mouse antibody binding was detected using a secondary anti-mouse IgG-FITC (Sigma).

Figure 8:
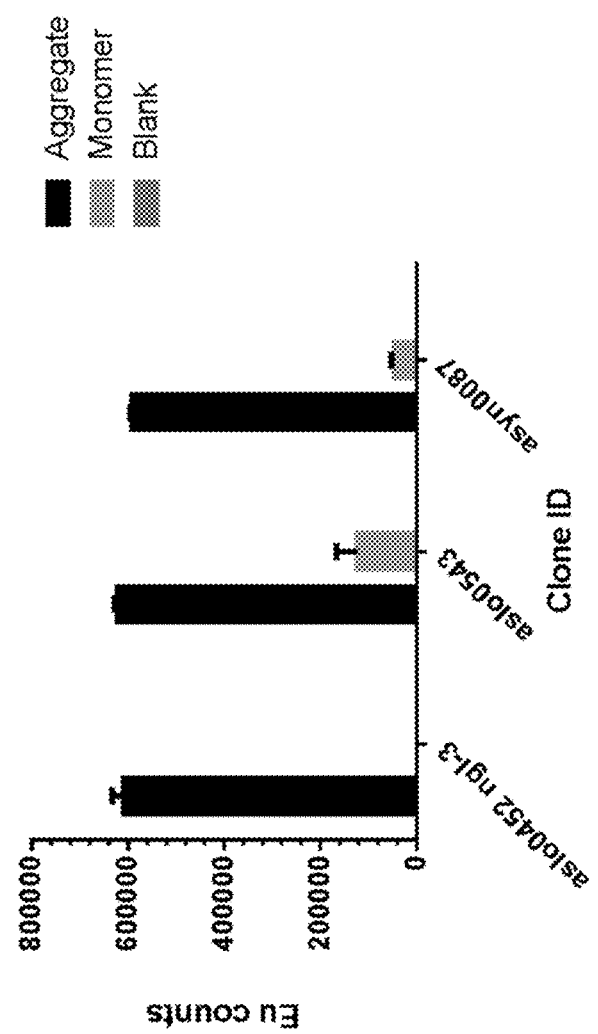

FIG. 8: Specificity of optimized anti-α-syn IgGs for aggregated human α-syn by DELFIA ELISA. The graph shows that aslo0452 ngl-3 and aslo0543, two high affinity α-syn specific clones, and the lead antibody asyn0087 detected captured aggregated forms of α-syn (black bars) but did not detect captured monomeric α-syn.

FIGS. 9A-9P: Specificity of affinity optimised clones in disease relevant tissues by immunohistochemistry. FIGS. 9A-9P show staining with aslo0452 ngl-3, asyn0087 and aslo0543, respectively. FIGS. 9A-9C show aslo0452 ngl-3 staining both Lewy bodies (FIGS. 9A-9B) and Lewy neurites (FIG. 9C) of the substantia nigra in PD brain tissue. FIG. 9D shows aslo0452 ngl-3 shows low level staining of α-syn in cells from the temporal cortex in a normal brain section. FIGS. E-G show aslo0452 ngl-3 staining Lewy bodies, Lewy neurites and Lewy dots of the amygdala in PD brain tissue. FIG. H shows an isotype matched control antibody demonstrating no staining in the amygdala in PD brain tissue. FIG. 9I-9M show asyn0087 staining of the Locus Coeruleus in PD brain tissue; pathological features identified are Lewy bodies (FIG. 9I-9L), neuronal aggregates (FIG. J), Lewy neurites (FIG. K), and Pale bodies (FIG. 9M). FIGS. 9N-9O show aslo0543 staining Lewy bodies and Lewy neurites in the substantia nigra in PD brain tissue. FIG. 9P shows aslo0543 low level staining of α-syn in cells from the temporal cortex in a normal brain section.

Figure 10A:
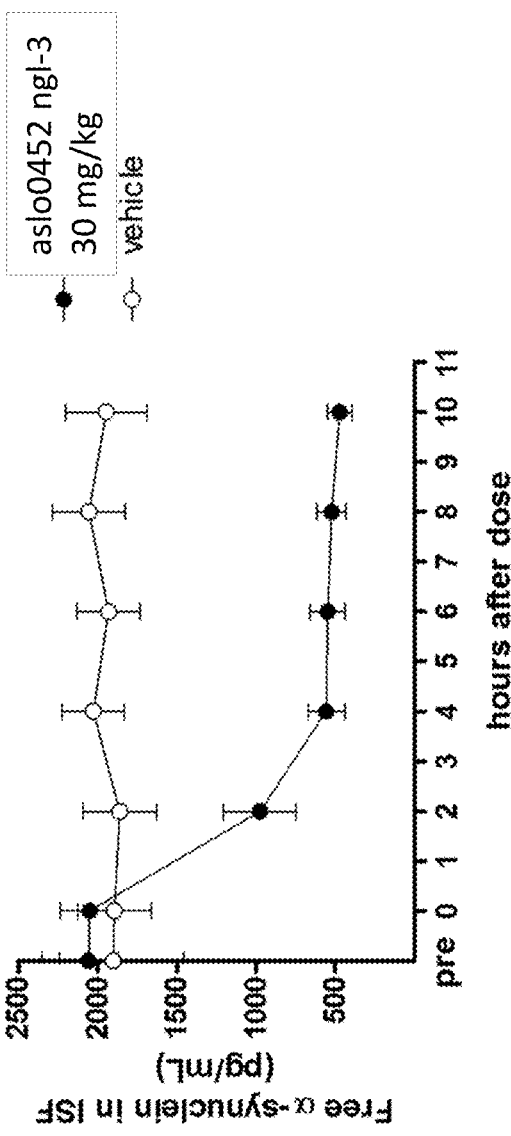
Figure 10B:
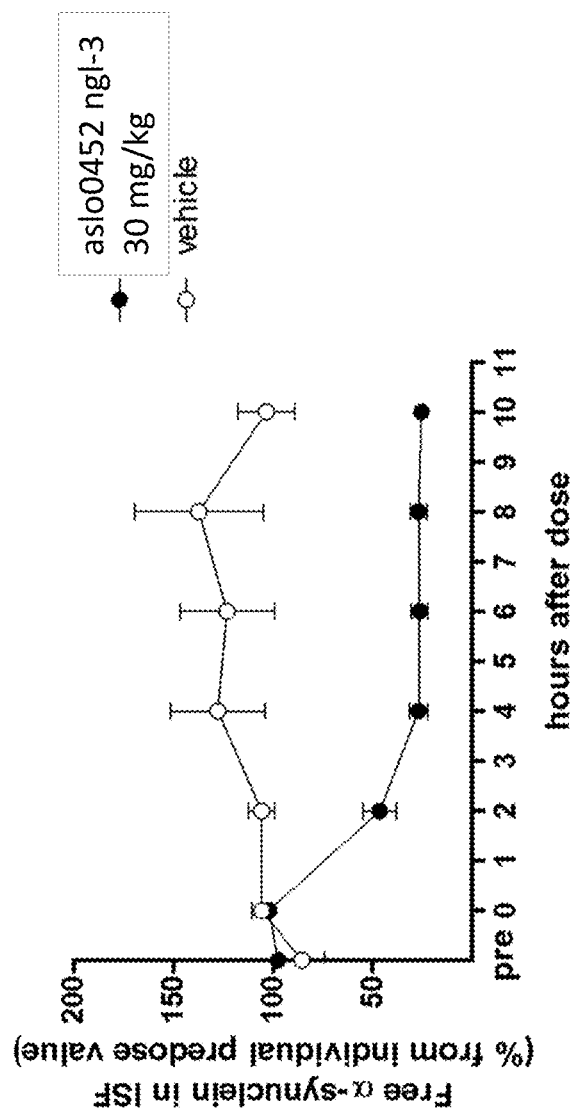

FIGS. 10A and 10B: Systemic administration of aslo0452 ngl-3 rapidly lowers free-asyn levels in prefrontal cortex of rats. Mean±SEM absolute (FIG. 10A) or relative (FIG. 10B) free α-synuclein concentration in ISF of aslo0452 ngl-3 (30 mg/kg intravenously; closed symbols) or vehicle (open symbols) treated rats.

Figure 11A:
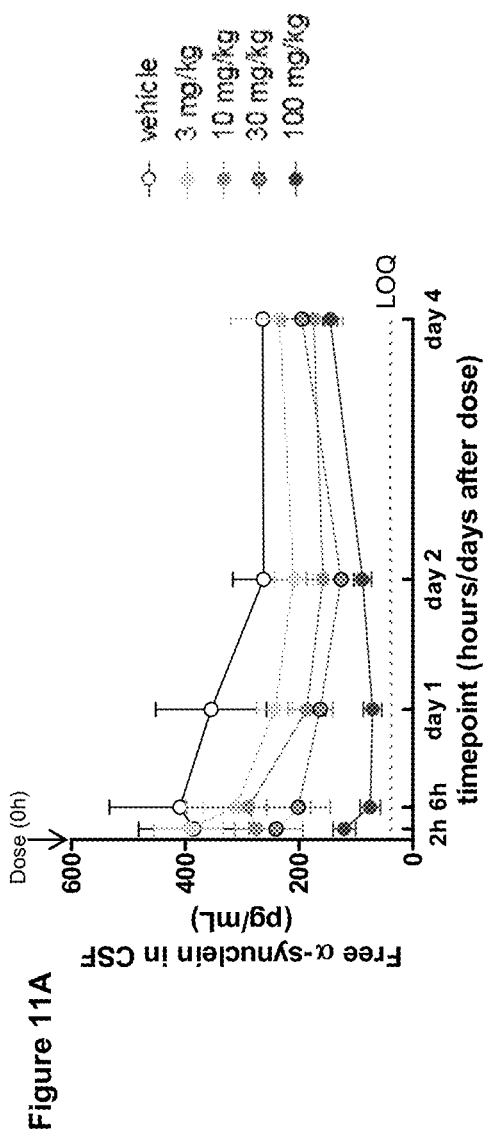
Figure 11B:
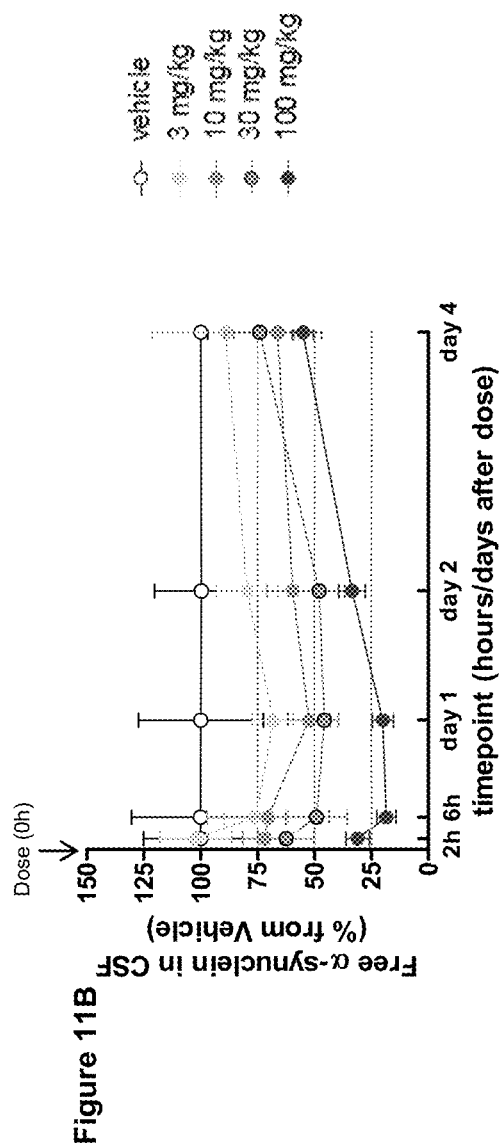

FIGS. 11A and 11B: Aslo0452 ngl-3 dose and time-dependently lowers free-asyn levels in CSF of rats upon systemic administration. Mean±SEM absolute (FIG. 11A) or relative (FIG. 11B) free α-synuclein concentration in CSF of aslo0452 ngl-3 (3, 10, 30, 100 mg/kg intravenously; closed symbols) or vehicle (open symbols) treated rats.

FIGS. 12A-12C: The anti-alpha-synuclein antibodies aslo0452 ngl-3 and aslo0452 ngl-3-D265A block ipsilateral-to-contralateral alpha-synuclein spreading. (FIG. 12A): non-tg mice injected with LV-α-syn into the right hippocampus (black arrows) were passively immunised with weekly doses of anti-alpha-synuclein mouse IgG1 antibodies: aslo0452 ngl-3, aslo0452 ngl-3 D265A, 9E4, or with NIP228 isotype control antibody, for 13 weeks, followed by determination of alpha-synuclein spreading by immunocytochemistry with SYN-1 and automated image analysis. (FIG. 12B): Quantification of alpha-synuclein immunoreactivity data obtained from immunocytochemical analysis of ipsilateral hippocampal coronal sections represented in A. Each column is the mean±SEM value of 10 independent antibody treatments (n=10 mice per antibody treatment group). *P<0.05 vs NIP228; 1-way ANOVA with Dunnett's post-test. (FIG. 12C): Quantification of alpha-synuclein immunoreactivity data obtained from immunocytochemical analysis of contralateral hippocampal coronal sections represented in panel A. Each column is the mean±SEM value of 10 independent antibody treatments (n=10 mice per antibody treatment group). *P<0.05 vs NIP228; 1-way ANOVA with Dunnett's post-test.

FIGS. 13A-13C: The anti-alpha-synuclein antibodies aslo0452 ngl-3 and aslo0452 ngl-3-D265A reduce deposition and dissemination of lentivirally-expressed alpha-synuclein along axons. (FIG. 13A): non-tg mice injected with LV-α-syn into the right hippocampus were passively immunised with weekly doses of anti-alpha-synuclein mouse IgG1 antibodies: aslo0452 ngl-3, aslo0452 ngl-3 D265A, 9E4, or with NIP228 isotype control antibody, for 13 weeks, followed by immunocytochemical analysis of alpha-synuclein deposits along ipsilateral and contralateral trans-hippocampal axons (black arrows). (FIG. 13B): Quantification of ipsilateral axonal alpha-synuclein deposits determined by immunocytochemistry with SYN-1 and automated image analysis. Each column is the mean±SEM value of 10 independent antibody treatments (n=10 mice per antibody treatment group). *P<0.05 vs NIP228; 1-way ANOVA with Dunnett's post-test. (FIG. 13C): Quantification of contralateral axonal alpha-synuclein deposits determined by immunocytochemistry with SYN-1 and automated image analysis. Each column is the mean±SEM value of 10 independent antibody treatments (n=10 mice per antibody treatment group). *P<0.05 vs NIP228; 1-way ANOVA with Dunnett's post-test.

FIGS. 14A-14C: The anti-alpha-synuclein antibodies aslo0452 ngl-3 and aslo0452 ngl-3-D265A reduce alpha-synuclein deposition in CA1 hippocampal neurons and layer 5 neocortical neurons. (FIG. 14A): Non-tg mice injected with LV-α-syn into the right hippocampus were passively immunised with weekly doses of anti-alpha-synuclein mouse IgG1 antibodies: aslo0452 ngl-3, aslo0452 ngl-3 D265A, 9E4, or with NIP228 isotype control antibody, for 13 weeks, followed by immunocytochemical analysis of alpha-synuclein deposits in ipsilateral CA1 hippocampal neurons and ipsilateral layer 5 neocortical neurons (black arrows). (FIG. 14B): Quantification of alpha-synuclein deposits in ipsilateral layer 5 neocortical neurons determined by immunocytochemistry with SYN-1 and automated image analysis. Data shown represents the number of alpha-synuclein positive cells (neurons) per 0.1 sq mm. Each column is the mean±SEM value of 10 independent antibody treatments (n=10 mice per antibody treatment group). *P<0.05 vs NIP228; 1-way ANOVA with Dunnett's post-test. (FIG. 14C): Quantification of alpha-synuclein deposits in ipsilateral CA1 hippocampal neurons determined by immunocytochemistry with SYN-1 and automated image analysis. Data shown represents the number of alpha-synuclein positive cells (neurons) per 0.1 sq mm. Each column is the mean±SEM value of 10 independent antibody treatments (n=10 mice per antibody treatment group). *P<0.05 vs NIP228; 1-way ANOVA with Dunnett's post-test.

FIGS. 15A-15C: aslo0452 ngl-3 and aslo0452 ngl-3-D265A antibodies block alpha-synuclein spreading in alpha-synuclein transgenic mice. (FIG. 15A): α-syn tg mice injected with LV-α-syn into the right hippocampus (black arrows) were passively immunised with weekly doses of anti-alpha-synuclein mouse IgG1 antibodies: aslo0452 ngl-3, aslo0452 ngl-3 D265A, 9E4, or with NIP228 isotype control antibody, for 13 weeks, followed by determination of alpha-synuclein spreading by immunocytochemistry with SYN-1 and automated image analysis. (FIG. 15B): Quantification of alpha-synuclein immunoreactivity data obtained from immunocytochemical analysis of ipsilateral hippocampal coronal sections represented in panel A. Each column is the mean±SEM value of 10 independent antibody treatments (n=10 mice per antibody treatment group). *P<0.05 vs NIP228; 1-way ANOVA with Dunnett's post-test. (FIG. 15C): Quantification of alpha-synuclein immunoreactivity data obtained from immunocytochemical analysis of contralateral hippocampal coronal sections represented in panel A. Each column is the mean±SEM value of 10 independent antibody treatments (n=10 mice per antibody treatment group). *P<0.05 vs NIP228; 1-way ANOVA with Dunnett's post-test.

FIGS. 16A-16C: aslo0452 ngl-3 and aslo0452 ngl-3-D265A antibodies reduce deposition and dissemination of lentivirally-expressed alpha-synuclein along axons in transgenic mice. (FIG. 16A): α-syn tg mice injected with LV-α-syn into the right hippocampus were passively immunised with weekly doses of anti-alpha-synuclein mouse IgG1 antibodies: aslo0452 ngl-3, aslo0452 ngl-3 D265A, 9E4, or with NIP228 isotype control antibody, for 13 weeks, followed by immunocytochemical analysis of alpha-synuclein deposits along ipsilateral and contralateral trans-hippocampal axons (black arrows). (FIG. 16B): Quantification of ipsilateral axonal alpha-synuclein deposits determined by immunocytochemistry with SYN-1 and automated image analysis. Each column is the mean±SEM value of 10 independent antibody treatments (n=10 mice per antibody treatment group). *P<0.05 vs NIP228; 1-way ANOVA with Dunnett's post-test. (FIG. 16C): Quantification of contralateral axonal alpha-synuclein deposits determined by immunocytochemistry with SYN-1 and automated image analysis. Each column is the mean±SEM value of 10 independent antibody treatments (n=10 mice per antibody treatment group). *P<0.05 vs NIP228; 1-way ANOVA with Dunnett's post-test.

FIGS. 17A-17D: aslo0452 ngl-3 and aslo0452 ngl-3-D265A antibodies reduce alpha-synuclein deposition in CA1 hippocampal neurons and layer 5 neocortical neurons in alpha-synuclein transgenic mice. (FIG. 17A): α-syn tg mice injected with LV-α-syn into the right hippocampus were passively immunised with weekly doses of anti-alpha-synuclein mouse IgG1 antibodies: aslo0452 ngl-3, aslo0452 ngl-3 D265A, 9E4, or with NIP228 isotype control antibody, for 13 weeks, followed by immunocytochemical analysis of alpha-synuclein deposits in ipsilateral CA1 hippocampal neurons and ipsilateral layer 5 neocortical neurons (black arrows). (FIG. 17B): Quantification of alpha-synuclein deposits in ipsilateral layer 5 neocortical neurons determined by immunocytochemistry with SYN-1 and automated image analysis. Data shown represents the number of alpha-synuclein positive cells (neurons) per 0.1 sq mm. Each column is the mean±SEM value of 10 independent antibody treatments (n=10 mice per antibody treatment group). *P<0.05 vs NIP228; 1-way ANOVA with Dunnett's post-test. (FIG. 17C): Quantification of alpha-synuclein deposits in ipsilateral CA1 hippocampal neurons determined by immunocytochemistry with SYN-1 and automated image analysis. Data shown represents the number of alpha-synuclein positive cells (neurons) per 0.1 sq mm. Each column is the mean±SEM value of 10 independent antibody treatments (n=10 mice per antibody treatment group). *P<0.05 vs NIP228; 1-way ANOVA with Dunnett's post-test. (FIG. 17D): Quantification of alpha-synuclein deposits in contralateral CA1 hippocampal neurons determined by immunocytochemistry with SYN-1 and automated image analysis. Data shown represents the number of alpha-synuclein positive cells (neurons) per 0.1 sq mm. Each column is the mean±SEM value of 10 independent antibody treatments (n=10 mice per antibody treatment group). *P<0.05 vs NIP228; 1-way ANOVA with Dunnett's post-test.

Figure 18:
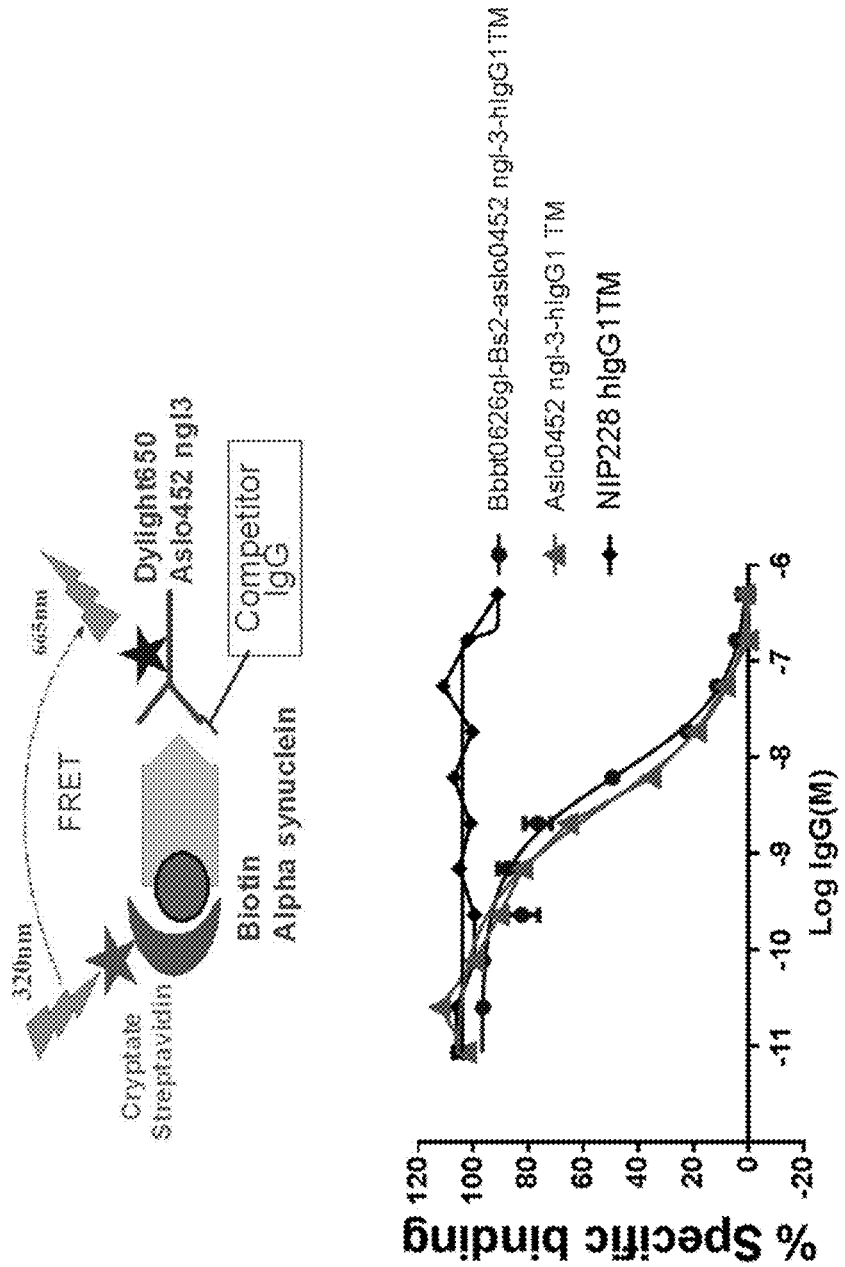

FIG. 18 Epitope competition of aslo0452-ngl3-hIgG1TM with BBBt0626gl-ScFv-Bs2-also0452-ngl-3-hIgG1TM demonstrates in a HTRF assay that the incorporation of a BBB moiety does not alter the binding specificity of aslo0452-ngl3-hIgG1TM. Dylight650 labelled anti-alpha-synuclein antibody, aslo0452hgl3-hIgG1TM binds to biotinylated alpha synuclein which in turn is bound to cyrptate labelled streptavidin. After excitation of the cyrptate an energy transfer (FRET) occurs and when in the presence of the dylight650 labelled aslo0452hgl3-hIgG1TM, the dylight650 is excited and results in a fluorescene. If a competitor IgG is present then the binding of the dylight650 labelled aslo0452 is blocked and excitation of the dylight650 labelled aslo0452 is prevented, resulting in a decrease of fluorescent signal. Unlabelled aslo0452 and Bbbt0626-Bs2-also0452 hIgG1TM both are able to similarly compete dylight650 labelled aslo0452-ngl3-hIgG1TM.

Figure 19:
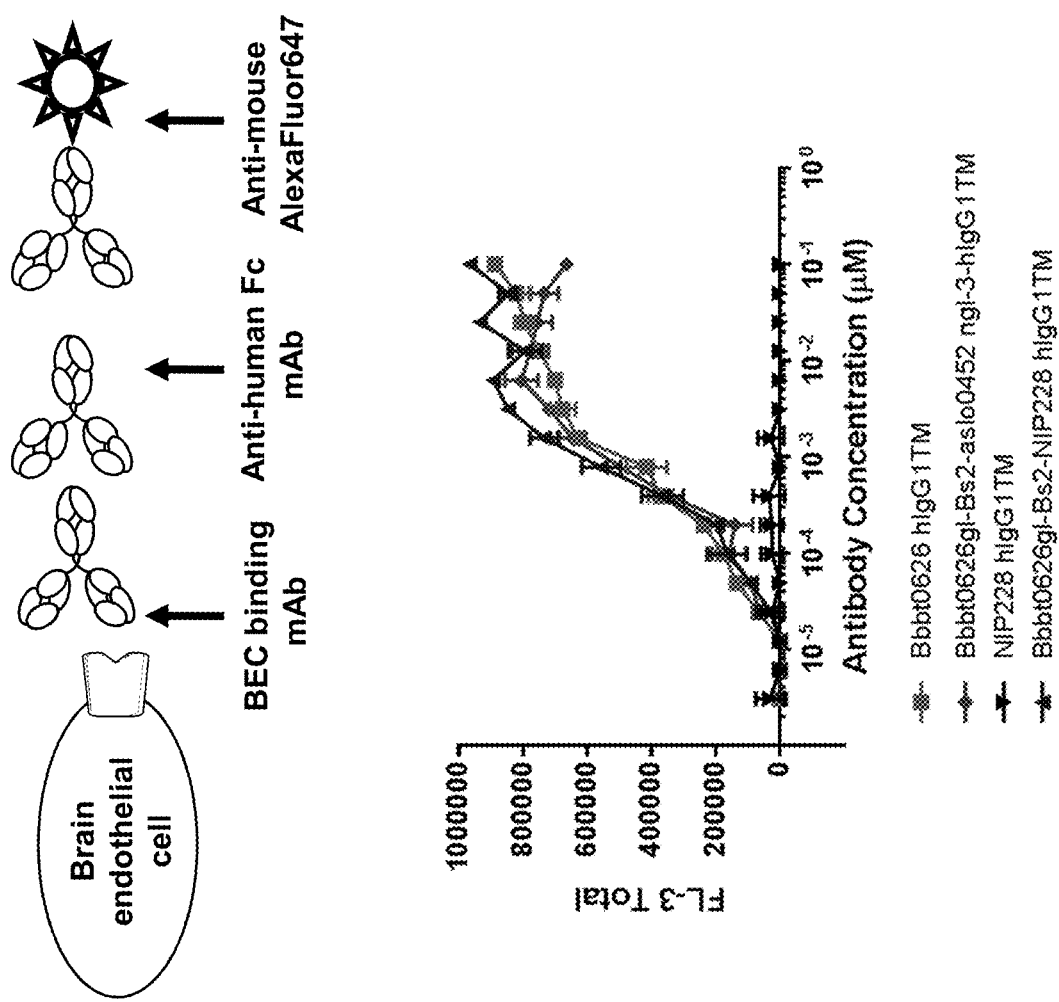

FIG. 19 Mouse brain endothelial cell binding of BBBt0626gl-BS2-aslo0452-ngl-3-hIgG1TM demonstrates effective target engagement of the BBB moiety when coupled to aslo0452-ngl3-hIgG1TM. FMAT (Fluorescence Micro-volume Assay Technology) or Mirror-ball assay technologies have both been used to determine specific binding of antibodies to brain endothelial cells. This assay measures the binding of human IgGs to mouse brain endothelial cells (b.End3). B.End3 cells are bound similarly by Bbbt0626 hIgG1TM, Bbbt0626glscFv-Bs2-aslo0452-hIgG1TM and Bbbt0626glscFv-Bs2-NIP228 hIgG1TM, but not by the control antibody NIP228 hIgG1TM. This binding is detected with a mouse anti-Fc mAb (human specific) which in turn is detected with an Alexafluor647 labelled goat anti-mouse Fc.

DETAILED DESCRIPTION OF THE INVENTION

The present invention is based upon the surprising and unexpected discovery of aslo0452 ngl-3 and aslo0543 antibodies. This discovery has led to a new group of antibodies having characteristics shared by the aslo0452 ngl-3 and aslo0543 antibodies, as well as sub-groups of antibodies having characteristics of aslo0452 ngl-3 and aslo0543, respectively.

In one embodiment, the antibody or antigen-binding fragment thereof of the present invention derives from antibody asyn0087 comprising a variable heavy chain region (VH) of amino acid sequence of SEQ ID NO: 2 and a variable light chain region (VL) of amino acid sequence SEQ ID NO: 3, as disclosed herewith.

In a particular embodiment, the antibody or antigen-binding fragment thereof of the present invention derives from antibody asyn0087, wherein said antibody or antigen-binding fragment has a $K_D$ of less than 500 nM and binds the same epitope as any one of antibodies asyn0087, aslo0452ngl-3 and aslo0543, described herewith.

Like asyn0087, the aslo0452 ngl-3 and aslo0543 antibodies bind the C-terminal region (residues 96-140) of human α-synuclein. More specifically aslo0452 ngl-3 and aslo0543 antibodies or antigen-binding fragment thereof binds the region comprised between about amino acid 102 and about amino acid 130 of human α-synuclein (e.g., SEQ ID NO: 1). In some embodiments, any of the antibodies or antigen-binding fragments disclosed herein bind the region comprised between about amino acid 120 and about 130 of human α-synuclein (e.g., SEQ ID NO: 1). In some embodiments, any of the antibodies or antigen-binding fragments disclosed herein bind an epitope that is not the same epitope as the epitope bound by the 9E4 antibody.

The aslo0452 ngl-3 and aslo0543 antibodies are selective for α-synuclein. The antibody or antigen-binding fragment thereof does not bind to other synuclein family members such as β-synuclein or γ-synuclein. More specifically, the antibody or antigen-binding fragment thereof is specific for human α-synuclein.

The aslo0452 ngl-3 and aslo0543 antibodies bind to human, rat or cynomolgus alpha-synuclein. The ability of aslo0452 ngl-3 and aslo0543 to bind to human, cynomolgus monkey and rat alpha-synuclein is indicative of binding to a different epitope on human alpha-synuclein as compared to antibodies that do not bind to human, cynomolgus monkey and rat alpha-synuclein. The aslo0452 ngl-3 and aslo0543 antibodies are thus capable of being used for in vivo safety evaluation and investigation in cynomolgus monkey and rat models of disease.

The aslo0452 ngl-3 and aslo0543 antibodies bind to human α-synuclein with high affinity. The aslo0452 ngl-3 and aslo0543 antibodies bind to alpha-synuclein with a $K_D$ of less than 500 picomolar (pM), less than 400 pM, less than 300 pM, less than 150 pM, less than 120 pM, less than 115 pM, less than 110 pM or 106 pM or less as measured for example using Octet analysis (see, e.g., Example 9). The aslo0452 ngl-3 and aslo0543 antibodies bind to alpha-synuclein with a $K_D$ of less than 300 picoMolar (pM), less than 250 pM, less than 200 pM, less than 150 pM, less than 120 pM, less than 110 pM or 108 pM, less than 100 pM, less than 80 pM or 74 pM or less as measured for example using KinExA analysis (for a reference KinExA analysis protocol, see, e.g., Example 9).

The aslo0452 ngl-3 Fab fragment binds to human α-synuclein with high affinity. The aslo0452 ngl-3 Fab fragment binds to alpha-synuclein with a $K_D$ of less than 300 picoMolar (pM), less than 200 pM, less than 180 pM, 174 pM or less as measured for example using KinExA analysis (see, e.g., Example 9.3).

The aslo0452 ngl-3 and aslo0543 antibodies bind to native endogenous human α-synuclein. The aslo0452 ngl-3 and aslo0543 antibodies bind to aggregates of human α-synuclein. In particular, the antibodies therefore bind to an epitope that is not required for aggregation. The aslo0452 ngl-3 and aslo0543 antibodies are capable of sequestering both monomeric and aggregated forms of alpha-synuclein. The antibody or antigen-binding fragment thereof of the invention are capable of binding monomeric and aggregated forms of alpha-synuclein.

The aslo0452 ngl-3 and aslo0543 antibodies bind disease relevant, pathological forms of α-synuclein, e.g. Lewy bodies, Lewy neurites, Lewy dots in Parkinson's disease brain tissues. Minimal staining is observed in normal (non-diseased) brain.

The aslo0452 ngl-3 antibody reduces α-synuclein levels in the brain interstitial fluid. In particular, the aslo0452 ngl-3 antibody reduces free unbound α-synuclein levels in the brain interstitial fluid.

The aslo0452 ngl-3 antibody reduces α-synuclein levels in the cerebrospinal fluid. In particular, the aslo0452 ngl-3 antibody reduces free unbound α-synuclein levels in the cerebrospinal fluid. The aslo0452 ngl-3 antibody reduces α-synuclein spreading in vivo. This novel function of inhibiting alpha-synuclein spreading is indicative of binding to a different epitope on human alpha-synuclein as compared to antibodies that do not inhibit spreading.

In some embodiments, any of the antibodies or antigen-binding fragments thereof disclosed herein have any one or more of the functional properties of aslo0452 ngl-3, e.g., any of the aslo0452 ngl-3 functional properties recited herein. In some embodiments, any of the antibodies or antigen-binding fragments thereof disclosed herein have any one or more of the functional properties of aslo0543, e.g., any of the aslo0543 functional properties recited herein.

In one embodiment, the antibody or antigen-binding fragment thereof of the present invention competes with antibody aslo0452 ngl-3 and/or aslo0543 for binding to human α-synuclein. In another embodiment, the antibody or antigen-binding fragment thereof of the present invention binds to the same epitope on human α-synuclein as antibody aslo0452 ngl-3 and/or aslo0543.

It can readily be determined whether an antibody or antigen-binding fragment thereof binds to the epitope of the reference antibody or antigen-binding fragment as defined above. Such methods are a matter of routine in the art. For example, an antibody can be compared to another by biochemical competition assay whereby, two antibodies (one labelled for detection purposed and one not) are incubated simultaneously with a given antigen. If a binding signal is achieved for the labelled antibody then the two antibodies are said to recognize distinct, non-overlapping epitopes on the protein of interest. If no binding signal is obtained then, conversely, they would be characterized as having overlapping epitopes on the protein sequence because binding of one antibody sterically hinders binding of the second antibody. Further, the amino acid location of a given epitope can also be identified using modified proteins such as truncates, linear peptide sequences derived from an antigen's primary amino sequence, species orthologues, and by proteolytic digest and mass spec analysis of an antibody bound to a given protein. These methodologies serve to generate a region of interaction between antibody and antigen.

Additional routine experimentation (such as peptide mutation and binding analyses) can be carried out to confirm whether any observed lack of binding is in fact due to binding the epitope of the invention or if some other phenomenon (such as steric hindrance) is responsible. Such experiments can be carried out using ELISA, RIA, Biacore, flow cytometry or other known antibody binding assays.

For example, for fine mapping of a specific epitope, mathematical models of the epitope:paratope interface can be derived from data generated through solving the structure of the antigen:antibody complex using a high resolution imaging method such as co-crystallization with X-ray diffraction. To confirm the relevance of the mathematical model derived, in terms of identifying key contact residues defining the epitope, point mutagenesis of the antigen must be performed subsequently and an analysis of the effect on strength of binding between antigen and antibody caused by such mutations established. Using this combination of methods an exact map of key contact residues comprising the epitope can be established.

Antibodies or antigen-binding fragments thereof which bind to the epitope of the antibody or antigen-binding fragment thereof of the invention may be generated by producing variants of the antibody or antigen-binding fragment thereof of the invention. Such variant antibodies or antigen-binding fragments thereof may have CDRs sharing a high level of identity with the CDRs of the antibody or antigen-binding fragment thereof of the invention. For instance, in some embodiments, any of the CDRs disclosed herein of any of the antibodies or antigen-binding fragments disclosed herein may differ by 1 or 2 amino acid residues as compared to any one or more of the specific CDR sequences referred to herein (e.g., any one or more of the CDRs having SEQ ID NOs: 5, 15, 16, 20, 10 and 21). Additionally, such antibodies may have one or more variations (e.g. a conservative amino acid substitution) in the framework regions.

In one embodiment, the antibodies or antigen-binding fragments thereof of the invention have variations in the CDR amino acid sequences that maintain at least 80%, at least 85%, at least 90%, at least 92%, at least 93%, at least 94%, at least 95%, at least 96%, at least 97%, at least 98% and up to 99% sequence identity to the CDRs of antibody aslo0452 ngl-3.

In particular, conservative amino acid substitutions are contemplated. Conservative replacements are those that take place within a family of amino acids that have related side chains. Genetically encoded amino acids are generally divided into families: (1) acidic: aspartate, glutamate; (2) basic: lysine, arginine, histidine; (3) non-polar: alanine, valine, leucine, isoleucine, proline, phenylalanine, methionine, tryptophan; and (4) uncharged polar: glycine, asparagine, glutamine, cysteine, serine, threonine, tyrosine. These families can be further categorised: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. Thus, in general one could expect that an isolated replacement of a leucine with an isoleucine or valine, an aspartate with a glutamate, a threonine with a serine, or a similar replacement of an amino acid with a structurally related amino acid, will not have a major effect on the binding function or properties of the resulting antibody, especially if the replacement does not involve an amino acid within a CDR site.

In one embodiment, the antibody or antigen-binding fragment thereof according to the invention comprises at least one CDR selected from:
  (i) H-CDR1 of SEQ ID NO: 5,
  (ii) H-CDR2 of SEQ ID NO: 6,
  (iii) H-CDR3 of SEQ ID NO: 7,
  (iv) L-CDR1 of SEQ ID NO: 9,
  (v) L-CDR2 of SEQ ID NO: 10,
  (vi) L-CDR3 of SEQ ID NO: 11.

In one embodiment, the antibody or antigen-binding fragment thereof of the present invention has at least one CDR selected from the CDRs of antibody aslo0452 ngl-3, i.e. at least one CDR selected from any one of SEQ ID NO: 5, SEQ ID NO: 15, SEQ ID NO: 16, SEQ ID NO: 20, SEQ ID NO: 10, SEQ ID NO: 21.

In another embodiment, the CDR3 of the heavy chain of the antibody or antigen-binding fragment thereof of the present invention is CDR3 of the heavy chain of antibody aslo0452 ngl-3; and/or the CDR3 of the light chain of the antibody or antigen-binding fragment thereof of the present invention is CDR3 of the light chain of antibody aslo0452 ngl-3. Thus, in one embodiment, the CDR3 of the heavy chain of the antibody or antigen-binding fragment thereof according to the invention is CDR3 of SEQ ID NO: 16 of the heavy chain of antibody aslo0452 ngl-3; and/or the CDR3 of the light chain of the antibody or antigen-binding fragment thereof according to the invention is CDR3 of SEQ ID NO: 21 of the light chain of antibody aslo0452 ngl-3.

In a further embodiment, the CDR3 of the heavy chain of the antibody or antigen-binding fragment thereof of the present invention is CDR3 of the heavy chain of antibody aslo0452 ngl-3.

In one embodiment, the CDR3 of the light chain of the antibody or antigen-binding fragment thereof of the present invention is CDR3 of the light chain of antibody aslo0452 ngl-3.

In one embodiment, the antibody or antigen-binding fragment thereof of the invention has the six CDRs of antibody aslo0452 ngl-3 i.e. three heavy chain CDRs having amino acid sequences SEQ ID NO: 5, SEQ ID NO: 15 and SEQ ID NO: 16; and three light chain CDRs having amino acid sequences SEQ ID NO: 20, SEQ ID NO: 10 and SEQ ID NO: 21.

The present invention provides an antibody or antigen-binding fragment thereof of the present invention comprising a variable heavy chain having at least 80%, 85%, 90%, 95%, 96%, 97%, 98%, 99%, or 100% identity to the nucleotide sequence defined by SEQ ID NO: 13 and a variable light chain having at least 80%, 85%, 90%, 95%, 96%, 97%, 98%, 99%, or 100% identity to the nucleotide sequence defined by SEQ ID NO: 18.

The present invention also provides an antibody or antigen-binding fragment thereof comprising a variable heavy chain having a nucleotide sequence defined by SEQ ID NO: 13 and a variable light chain having a nucleotide sequence defined by SEQ ID NO: 18.

The present invention provides an antibody or antigen-binding fragment thereof of the present invention comprising a variable heavy chain having at least 80%, 85%, 90%, 95%, 96%, 97%, 98%, 99%, or 100% identity to the amino acid sequence defined by SEQ ID NO: 14 and a variable light chain having at least 80%, 85%, 90%, 95%, 96%, 97%, 98%, 99%, or 100% identity to the amino acid sequence defined by SEQ ID NO: 19.

In one embodiment, the antibody, or antigen-binding fragment thereof, comprises (i) a variable heavy chain having at least 80%, 85%, 90%, 95%, 96%, 97%, 98%, 99%, or 100% identity to the amino acid sequence defined by SEQ ID NO: 14 and a variable light chain having at least 80%, 85%, 90%, 95%, 96%, 97%, 98%, 99%, or 100% identity to the amino acid sequence defined by SEQ ID NO: 19, and (ii) the six CDRs of antibody aslo0452 ngl-3.

The present invention provides an antibody or antigen-binding fragment thereof according to the invention comprising a variable heavy chain having the amino acid sequence of SEQ ID NO: 14 and a variable light chain having the amino acid sequence of SEQ ID NO: 19.

In one embodiment, the antibody or antigen-binding fragment thereof according to the invention has the six CDRs of antibody aslo0543.

Thus, in one embodiment, the antibody, or antigen-binding fragment thereof according to the invention comprises:
  a) three heavy chain CDRs having sequences:
    (i) H-CDR1 of SEQ ID NO: 25,
    (ii) H-CDR2 of SEQ ID NO: 26; and
    (iii) H-CDR3 of SEQ ID NO: 27, and b) three light chain CDRs having sequences:
   (i) L-CDR1 of SEQ ID NO: 31,
   (ii) L-CDR2 of SEQ ID NO: 32; and
   (iii) L-CDR3 of SEQ ID NO: 33.

In a further embodiment, the antibody, or antigen-binding fragment thereof according to the invention comprises a variable heavy chain having at least 80%, 85%, 90%, 95%, 96%, 97%, 98%, 99%, or 100% identity to the sequence defined by SEQ ID NO: 14 and a variable light chain having at least 80%, 85%, 90%, 95%, 96%, 97%, 98%, 99%, or 100% identity to the sequence defined by SEQ ID NO: 19 and further comprises:
   a) three heavy chain CDRs having sequences:
      (vii) H-CDR1 of SEQ ID NO: 25,
      (viii) H-CDR2 of SEQ ID NO: 26; and
      (ix) H-CDR3 of SEQ ID NO: 27, and
   b) three light chain CDRs having sequences:
      (vii) L-CDR1 of SEQ ID NO: 31,
      (viii) L-CDR2 of SEQ ID NO: 32; and
      (ix) L-CDR3 of SEQ ID NO: 33.

The present invention also provides an antibody or antigen-binding fragment thereof comprising a variable heavy chain having a nucleotide sequence defined by SEQ ID NO: 23 and a variable light chain having a nucleotide sequence defined by SEQ ID NO: 29.

The present invention also provides an antibody or antigen-binding fragment thereof of the present invention comprising a variable heavy chain having the amino acid sequence of SEQ ID NO: 24 and a variable light chain having the amino acid sequence of SEQ ID NO: 30.

In a further embodiment, the antibody, or antigen-binding fragment thereof, comprises a heavy chain having an amino acid sequence defined by SEQ ID NO: 22 and a light chain having an amino acid sequence defined by SEQ ID NO: 28.

The framework region and CDRs or an antibody may be precisely defined (see, Kabat et al. Sequences of Proteins of Immunological Interest, Fifth Edition, U.S. Department of Health and Human Services (1991), 91-3242, 1991; and Chothia et al. J. Mol. Biol. (1987), 196:901-917, both of which are incorporated herein by reference).

Minor variations in the amino acid sequences of antibody or antigen-binding fragment thereof of the invention are contemplated as being encompassed by the present invention, providing that the variations in the amino acid sequence(s) maintain at least 75%, more preferably at least 80%, at least 90%, at least 95%, and most preferably at least 99% sequence identity to the antibody or antigen-binding fragment thereof of the invention as defined anywhere herein. In particular, conservative amino acid replacements are contemplated.

The invention also provides a single chain amino acid sequence comprising the light chain of an antibody or antigen-binding fragment thereof of the present invention as defined anywhere herein. The invention also provides a single chain amino acid sequence comprising the heavy chain of an antibody or antigen-binding fragment thereof of the present invention as defined anywhere herein.

Optimal alignment of sequences for comparison may be conducted, for example, by the local homology alignment algorithm of Smith and Waterman (Smith and Waterman, Adv. Appl. Math. 2 (1981), 484; incorporated herein by reference), by the algorithm of Needleman & Wunsch (Needleman & Wunsch, J. Mol. Biol. (1970), 48: 443; incorporated herein by reference) by the search for similarity method of Pearson & Lipman (Pearson & Lipman, Proc Natl Acad Sci USA (1988), 85: 2444; incorporated herein by reference), by computer implementations of these algorithms (GAP, BESTFIT, FASTA, and TFASTA—Sequence Analysis Software Package of the Genetics Computer Group, University of Wisconsin Biotechnology Center, 1710 University Avenue, Madison, Wis. 53705), or by visual inspection (see Current Protocols in Molecular Biology, F. M. Ausbel et al, eds, Current Protocols, a joint venture between Greene Publishing Associates, In. And John Wiley & Sons, Inc. (1995 Supplement) Ausbubel; incorporated herein by reference).

Examples of algorithms suitable for determining percent sequence similarity or identity are the BLAST and BLAST 2.0 algorithms (see Altschul et al. J. Mol. Biol. (1990), 215(3): 403-410; and "www.ncbi.nlm.nih.gov" of the National Center for Biotechnology Information; both of which are incorporated herein by reference).

In one embodiment, the antibody or antigen-binding fragment thereof of the invention is isolated. In another embodiment, the antibody or antigen-binding fragment thereof of the invention is purified.

In one embodiment, the antibody or antigen-binding fragment thereof of the invention is a monoclonal antibody. In another embodiment, the antibody or antigen-binding fragment thereof of the invention is a humanised antibody. In yet another embodiment, the antibody or antigen-binding fragment thereof of the invention is a human antibody.

In one embodiment, the antibody or antigen-binding fragment thereof of the present invention is an IgA, IgD, IgE, IgM or IgG, such as IgG1, IgG2, IgG3, and IgG4, antibody or antigen-binding fragment thereof.

In another embodiment, the antibody or antigen-binding fragment thereof of the invention has reduced binding affinity to IgG Fc receptors. Thus the antibody or antigen-binding fragment of the invention has a low immunogenic effect. In one embodiment, the antibody or antigen-binding fragment thereof is an IgG1 TM antibody or antigen-binding fragment thereof. IgG1 TM is a IgG1 triple mutant, which contains 3 point mutations (L234F/L235E/P331S) in the Fc domain that reduce the binding affinity of the antibody or antigen-binding fragment thereof to Fc-gamma receptors (FcγRs) (Oganesyan et al. Acta Crystallogr D Biol Crystallogr, (2008) 64: 700-704; incorporated herein by reference). In some embodiments, the antibody-mediated prevention of alpha-synuclein spreading by the antibodies of the invention thus does not require Fc-associated effector functions as a key mechanism of action.

Antigen-binding fragments include Fab, Fv, scFv, dAb, Fd, Fab', F(ab')$_2$ or an isolated complementarity determining region (CDR) having sufficient framework to bind. A Fab fragment may be a monovalent fragment consisting of the VL, VH, CL and CH1 domains. A F(ab')$_2$ fragment may be a bivalent fragment comprising two Fab fragments linked by a disulfide bridge at the hinge region. A Fc fragment may consist of the CH2 and CH3 domains. A Fv fragment may consist of the VL and VH domains of a single arm of an antibody. A dAb fragment (Ward et al. Nature (1989), 341: 544-546; incorporated herein by reference) may consist of a VH domain. An isolated complementarity determining region (CDR) having sufficient framework to bind may be an antigen binding portion of a variable region.

An antigen binding portion of a light chain variable region and an antigen binding portion of a heavy chain variable region, e.g., the two domains of the Fv fragment, VL and VH, can be joined, using recombinant methods, by a synthetic linker that enables them to be made as a single protein chain in which the VL and VH regions pair to form monovalent molecules (known as single chain Fv (scFv); see e.g., Bird et al. Science (1988), 242(4877): 423-426; and Huston et al. Proc Natl Acad Sci USA (1988), 85: 5879-5883; both of which are incorporated herein by reference). These are obtained using conventional techniques known to those with skill in the art, and the portions are screened for utility in the same manner as are intact antibodies.

Antibodies or antigen-binding fragments thereof of the invention may have any or all of the advantageous properties as defined above or combinations thereof. In particular, antibodies or antigen-binding fragments thereof of the invention may be selective for alpha-synuclein and be able to slow or prevent cell-to-cell transmission and spreading of alpha-synuclein in vivo.

The functionality of the resulting antibody or antigen-binding fragment thereof of the invention and in particular (i) its ability to bind the epitope of alpha-synuclein; and (ii) its ability to slow or prevent cell-to-cell transmission and spreading of alpha-synuclein in vivo can readily be determined by assaying its specific activity using the techniques described herein in the Examples.

This disclosure provides compositions for delivery of the antibody or antigen-binding fragment thereof according to the invention across the blood-brain barrier (BBB) using a transporter molecule that can cross brain endothelial cells while associated with said antibody or fragment, e.g., while fused or conjugated to said antibody or fragment. BBB sequences are provided herein.

As used herein, the term "payload" is used as shorthand for antibody or antigen-binding fragment thereof as described herewith whose transport across the BBB can be facilitated by a transporter molecule as provided herein. In particular embodiments, the "payload" covers the heavy chain variable region of the antibodies of the invention, more particularly the heavy chain variable region of also0452 ngl-3 or aslo0543.

A payload can be part of the transporter molecule, e.g., as a fusion polypeptide, or joined to the polypeptide through disulfide bonds or other covalent bonds. Alternatively the payload can be associated with the transporter molecule in any way that will allow the transporter molecule to facilitate its transport across the BBB, as further described below. In certain aspects the payload remains part of the transporter molecule following BBB transport, and retains central nervous system (CNS) activity in that form. Alternatively the payload can be associated with the transporter molecule during BBB transport, but in a way that allows it to disassociate with the transporter molecule following BBB transport.

The disclosure further provides methods for the treatment or diagnosis of a disease or disorder of the CNS, in particular an α-synucleinopathy, comprising the use of such transporter molecules associated with an antibody or antigen binding fragment thereof according to the invention.

In certain aspects, this disclosure provides an isolated transporter molecule comprising an immunoglobulin-derived polypeptide. In certain aspects the polypeptide is a mimetic or non-mimetic of the camelid antibody FC5, identified and isolated using Fluorescence Micro-volume Assay Technology (FMAT) to detect binding to brain microvascular endothelial cells (BMVEC), e.g., mouse B.End3 cells. In certain aspects, the immunoglobulin-derived polypeptide is an antibody or an active fragment thereof, where "active" means that the transporter molecule can, e.g., bind to BMVEC in one or more species, e.g., mouse BMVEC, rat BMVEC, cynomolgus monkey BMVEC, or human BMVEC, internalize into BMVEC of one or more species, and/or cross the blood brain barrier either alone, or associated with a payload.

In some embodiments, the BBB transporter molecule is a BBB transporter molecule described in U.S. Provisional Patent Application No. 62/094,503, which is incorporated herein by reference in its entirety. In certain aspects, the transporter molecule comprises one or more of Bbbt0241, Bbbt0626, Bbbt0626gl, Bbbt0632, BBBt0632gl Bbbt0654, Bbbt0726, Bbbt0727, Bbbt0732, Bbbt0754, Bbbt0674, Bbbt0755, Bbbt0643, Bbbt0579 or Bbbt0671 as described in U.S. Provisional Patent Application No. 62/094,503, which is incorporated herein by reference in its entirety.

In a particular embodiment, the BBB transporter molecule is Bbbt0626 or BBBt0632.

In certain embodiments, the BBB transporter molecule is germlined, e.g., Bbbt0626gl is a germlined version of Bbbt0626, called "Bbbt0626gl".

In a further particular embodiment, the BBB transporter molecule is BBBt0632gl or Bbbt0626gl.

In certain aspects, the transporter molecule does not bind to BMVEC but is still capable of transporting across the BBB as indicated in in vitro transcytosis assay.

With reference to the BBB transporter molecules, the VH CDRs sequences described correspond to the classical Kabat numbering locations, namely Kabat H-CDR1 is at positions 31-35, H-CDR2 is a positions 50-65, and H-CDR3 is at positions 95-102. L-CDR2 and L-CDR3 also correspond to classical Kabat numbering locations, namely positions 50-56 and 89-97, respectively. As used herein, the terms "L-CDR1" or "light chain CDR1" correspond to sequences located at Kabat positions 23-34 in the VL (in contrast, the classical L-CDR1 location according to the Kabat numbering schema corresponds to positions 24-34).

In certain aspects, the immunoglobulin-derived polypeptide comprises immunoglobulin heavy chain complementarity determining regions (CDRs). For example the immunoglobulin-derived polypeptide can include an immunoglobulin heavy chain complementarity-determining region-1 (H-CDR1), an immunoglobulin heavy chain complementarity-determining region-2 (H-CDR2), an immunoglobulin heavy chain complementarity-determining region-3 (H-CDR3). In certain aspects, the immunoglobulin-derived polypeptide can further comprise, or alternatively comprise, immunoglobulin light chain CDRs. For example, the immunoglobulin-derived polypeptide can include an immunoglobulin light chain complementarity-determining region-1 (L-CDR1), an immunoglobulin light chain complementarity-determining region-2 (L-CDR2), and an immunoglobulin light chain complementarity-determining region-3 (L-CDR3).

In certain aspects, the immunoglobulin-derived polypeptide contains an H-CDR1, an H-CDR2, an H-CDR3, an L-CDR1, an L-CDR2, and an L-CDR3 with the following amino acid sequences, respectively:
  (a) SEQ ID NO: 40 as H-CDR1, SEQ ID NO: 41 as H-CDR2, SEQ ID NO: 42 as H-CDR3, SEQ ID NO: 36 as L-CDR1, SEQ ID NO: 37 as L-CDR2, and SEQ ID NO: 38 as L-CDR3, wherein the CDRs are similar to those of Bbbt0626 and Bbbt0626gl;
  (b) SEQ ID NO: 40 as H-CDR1, SEQ ID NO: 41 as H-CDR2, SEQ ID NO: 42 as H-CDR3, SEQ ID NO: 44 as L-CDR1, SEQ ID NO: 45 as L-CDR2, and SEQ ID NO: 46 as L-CDR3, wherein the CDRs are identical to those of Bbbt0626 and Bbbt062gl.

In certain aspects, the immunoglobulin-derived polypeptide contains an H-CDR1, an H-CDR2, an H-CDR3, an L-CDR1, an L-CDR2, and an L-CDR3 with the following amino acid sequences, respectively:

(a) SEQ ID NO: 49 as H-CDR1, SEQ ID NO: 50 as H-CDR2, SEQ ID NO: 51 as H-CDR3, SEQ ID NO: 53 as L-CDR1, SEQ ID NO: 54 as L-CDR2, and SEQ ID NO: 55 as L-CDR3, wherein the CDRs are similar to those of Bbbt0632gl;

(b) SEQ ID NO: 49 as H-CDR1, SEQ ID NO: 50 as H-CDR2, SEQ ID NO: 51 as H-CDR3, SEQ ID NO: 53 as L-CDR1, SEQ ID NO: 54 as L-CDR2, and SEQ ID NO: 55 as L-CDR3, wherein the CDRs are identical to those of Bbbt0632gl;

In certain alternative embodiments, one or more CDRs as described above are identical to the recited CDRs, except for, e.g., 1, 2, 3, 4, or 5 single amino acid deletions, substitutions, or insertions.

In certain embodiments, the transporter molecule as provided above can cross the blood brain barrier.

In certain aspects, the H-CDR1, the H-CDR2, the H-CDR3, the L-CDR1, the L-CDR2, and the L-CDR3 can be situated in immunoglobulin framework regions to produce an antibody VH and an antibody VL. In certain aspects the framework regions can be human-derived framework regions. In certain aspects the antibody VH and antibody VL are fused together, e.g., through a flexible peptide linker, to form a scFv molecule. In certain aspects the VH and VL further comprise one or more immunoglobulin constant domains, e.g., a CH1 domain, a hinge region, a CH3 domain, a CH3 domain, a CL-kappa domain, and/or a CL lambda domain. In certain aspects the one or more immunoglobulin constant domains are derived from a human immunoglobulin, e.g., a human IgG1 immunoglobulin. In certain aspects the VH, VL, and/or constant domains can comprise mutations to facilitate, e.g., longer or shorter half-life, increased or reduced effector functions, or the ability to attach a payload molecule either via peptide fusion, a disulfide bond, or chemical conjugation.

In certain aspects of the invention are provided antibodies or antigen-binding fragments thereof according to the invention associated with a transporter molecule that can cross brain endothelial cells as described herewith.

In particular aspects, this disclosure provides an antibody or antigen-binding fragment thereof according to the invention associated with a transporter molecule comprising an immunoglobulin-derived polypeptide, where the polypeptide comprises an immunoglobulin heavy chain variable region (VH) region and an immunoglobulin light chain variable region (VL) region. In certain aspects the immunoglobulin-derived polypeptide comprises sequences provided herein, including:

(a) a VH amino acid sequence at least 80%, 84%, 85%, 90%, 95%, 96%, 97%, 98%, or 99% identical to SEQ ID NO: 39 and a VL amino acid sequence at least 80%, 84%, 85%, 90%, 95%, 96%, 97%, 98%, or 99% identical to SEQ ID NO: 43, where SEQ ID NO: 39 and SEQ ID NO: 43 encode the VH and VL regions of Bbbt0626gl, (b) a VH amino acid sequence at least 80%, 84%, 85%, 90%, 95%, 96%, 97%, 98%, or 99% identical to SEQ ID NO: 47 and a VL amino acid sequence at least 80%, 84%, 85%, 90%, 95%, 96%, 97%, 98%, or 99% identical to SEQ ID NO: 43, where SEQ ID NO: 47 and SEQ ID NO: 43 encode the VH and VL regions of Bbbt0626, (c) a VH amino acid sequence at least 80%, 84%, 85%, 90%, 95%, 96%, 97%, 98%, or 99% identical to SEQ ID NO: 48 and a VL amino acid sequence at least 80%, 84%, 85%, 90%, 95%, 96%, 97%, 98%, or 99% identical to SEQ ID NO: 43, where SEQ ID NO: 48 and SEQ ID NO: 43 encode the VH and VL regions of Bbbt0632

In certain aspects, this disclosure provides an antibody or antigen-binding fragment thereof according to the invention associated with a transporter molecule comprising an immunoglobulin-derived polypeptide, where the immunoglobulin-derived polypeptide comprises a VH region and a VL region, where:

(a) the VH region comprises SEQ ID NO: 34 and the VL region comprises SEQ ID NO: 35; or
(b) the VH region comprises SEQ ID NO: 39 and the VL region comprises SEQ ID NO: 43; or
(c) the VH region comprises SEQ ID NO: 39 and the VL region comprises SEQ ID NO: 35; or
(d) the VH region comprises SEQ ID NO: 47 and the VL region comprises SEQ ID NO: 43; or
(e) the VH region comprises SEQ ID NO: 47 and the VL region comprises SEQ ID NO: 35; or
(f) the VH region comprises SEQ ID NO: 48 and the VL region comprises SEQ ID NO: 52

In a further embodiment, the VH and VL regions of the transporter molecule as described above are covalently linked to form a single chain fragment (ScFv).

In certain aspects, the transporter molecule provided herewith has transporter activity, e.g., it can bind to BMVEC from one or more species, e.g., mouse, rat, cynomolgus monkey, or human BMVEC, it can internalize into BMVEC of one or more species, or it can cross the blood brain barrier.

In certain aspects, a transporter molecule as provided herein comprises an immunoglobulin-derived polypeptide, where the immunoglobulin-derived polypeptide comprises an antibody or a BBB-penetrable fragment thereof.

A "BBB-penetrable fragment" as described herein is a fragment of the transporter molecule that can specifically bind to BMVEC of one or more species and cross through BMVEC in vitro or in vivo from the peripheral vasculature into the CNS vasculature. Whether a given fragment is a BBB-penetrable fragment can be tested by a variety of in vitro or in vivo assays known to persons of ordinary skill in the art. For example, the transporter molecule can be tested in an in vitro transcytosis assay, in an in vivo assay such as a diuresis assay, as described in U.S. 62/094,503. Other assays that could be used to measure in vivo delivery of payloads across the BBB include, without limitation, chronic constriction injury (CCI); spared nerve injury model (SNI) or spinal nerve ligation (SNL), all of which can be measured via paw flick, or the Hargreaves method (Hargreaves K, et al., Pain; 1988; 32; 77-88). in certain aspects, a transporter molecule as provided herein can bind to BMVEC from one or more species, e.g., human, cynomolgus monkey, murine, rat, or bovine BMVEC. Binding can be demonstrated in various ways known to persons of ordinary skill in the art, e.g., in a FMAT assay as described in U.S. 62/094,503. In certain aspects, the BMVEC are brain capillary endothelial cells (BCEC). In certain aspects, a transporter molecule as provided herein can pass through a monolayer of BCEC in an in vitro transcytosis assay. In certain aspects, transporter molecule activity can be demonstrated by visualization of the transporter molecule in the CNS. For example, a tritium-labeled transporter molecule can be delivered to a subject, e.g., a mouse peripherally, e.g., intravenously, and then visualized in the CNS via quantitative whole body radiography. In certain aspects, the transporter molecule localizes in specific regions of the CNS, e.g., the cortex of cerebellum, the gray matter of the cerebrum, the gray matter of the spinal cord, the pons, or a combination thereof.

In certain aspects, a transporter molecule as described herein comprises an antibody or BBB-penetrable fragment thereof that comprises or consists of two or more subunits, e.g., a heavy chain or fragment thereof and a light chain or fragment thereof, where the heavy chain and light chain are associated, e.g., as a single fusion protein (e.g., a scFv), or as two subunits held together by one or more disulfide bonds. In certain aspects the heavy chain comprises a VH domain or region and the light chain comprises a VL domain or region.

In one embodiment, the invention provides an antibody or antigen-binding fragment thereof according to the invention associated to a blood-brain barrier transporter molecule as described herewith.

In a particular embodiment, the antibody or antigen-binding fragment thereof according to the invention is associated to a blood-brain barrier transporter molecule, wherein the transporter molecule is a single chain fragment (scFv) comprising:
  i. the heavy chain variable region (VH) of BBBt0626gl of SEQ ID NO: 39 and the light chain variable region (VL) of BBBt0626gl of SEQ ID NO: 43, or
  ii. the heavy chain variable region (VH) of BBBt0626 of SEQ ID NO: 47 and the light chain variable region (VL) of BBBt0626 of SEQ ID NO: 43,
  iii. the heavy chain variable region (VH) of BBBt0632gl of SEQ ID NO: 48 and the light chain variable region (VL) of BBBt0632gl of SEQ ID NO: 52

In certain aspects the heavy chain further comprises a heavy chain constant domain, e.g., a CH1 domain, a hinge, a CH2 domain, and/or a CH3 domain, or fragment thereof. In certain aspects the heavy chain constant domain is an IgG constant domain or fragment thereof, e.g., a human IgG constant domain, e.g., a human IgG1, IgG2, IgG3 or IgG4 constant domain. In certain aspects, the IgG constant domain or fragment thereof comprises an altered glycosylation and/or one or more amino acid substitutions relative to a wild-type IgG constant domain wherein the modified IgG has a particular property, e.g., an increased or decreased half-life compared to the half-life of an IgG having the wild-type IgG constant domain, either increased or decreased effector functions relative to a wild-type IgG constant domain, or the ability to attach heterologous moieties via, e.g., a peptide bond, a disulfide bond, or a chemical conjugation. In certain aspects, the IgG constant domain or fragment thereof has an altered glycosylation relative to a wild-type IgG constant domain wherein the modified IgG has a particular property, e.g., an increased or decreased half-life compared to the half-life of an IgG having the wild-type IgG constant domain, either increased or decreased effector functions relative to a wild-type IgG constant domain.

In some embodiments, the antibody or antigen binding fragment thereof according to the invention is associated with BBBt0626 or BBBt0626gl, as defined herewith, forming bispecific antibody molecules.

In other embodiments, said bispecific antibodies according to the invention comprise the human IgG1 TM backbone (i.e. the heavy chain CH1, CH2, CH3 regions of an IgG1 TM) associated with a single chain fragment (scFv) comprising the VH and VL regions of BBBt0626 or BBBt0626gl grafted to the N-terminus ("BiS2 format") or C-terminus ("BiS3 format") of the heavy chain or N-terminus ("BiS1 format") of the VL, of an anti-α-synuclein antibody according to the invention. BiS format references are as disclosed in DiMasi et al. J Mol Biol. 2009 Oct. 30; 393(3):672-92.

In some embodiments, said bispecific antibodies according to the invention further comprise a light chain comprising the kappa or lambda CL region associated with the VL of an anti-α-synuclein antibody according to the invention.

In particular embodiments, the bispecific antibodies according to the invention comprise the human IgG1 TM backbone associated with:
  (i) a single chain fragment (scFv) of BBBt0626gl comprising the heavy chain variable region (VH) of SEQ ID NO: 39 and the light chain variable region (VL) of SEQ ID NO: 43; or
  (ii) a single chain fragment (scFv) of Bbbt0626 comprising the heavy chain variable region (VH) of SEQ ID NO: 47 and the light chain variable region (VL) of SEQ ID NO: 43,
  wherein said ScFv is grafted to the N-terminus (BiS2 format) or C-terminus (BiS3 format) of the heavy chain of aslo0452 ngl-3 of SEQ ID NO: 12 or N-terminus ("BiS1 format") of the light chain of SEQ ID NO. 17.

In still further particular embodiments, the bispecific antibodies according to the invention comprise the human IgG1 TM backbone associated with a single chain fragment (scFv) of BBBt0626gl comprising (i) the heavy chain variable region (VH) of SEQ ID NO: 39 and (ii) the light chain variable region (VL) of SEQ ID NO: 43; wherein said ScFv is grafted to the N-terminus (BiS2 format) or C-terminus (BiS3 format) of the heavy chain of aslo0452 ngl-3 of SEQ ID NO: 12 or N-terminus ("BiS1 format") of the light chain of SEQ ID NO. 17.

In other particular embodiments, the bispecific antibodies according to the invention comprise the human IgG1 TM backbone associated with:
  (i) a single chain fragment (scFv) of BBBt0626gl comprising the heavy chain variable region (VH) of SEQ ID NO: 39 and the light chain variable region (VL) of SEQ ID NO: 43; or
  (ii) a single chain fragment (scFv) of Bbbt0626 comprising the heavy chain variable region (VH) of SEQ ID NO: 47 and the light chain variable region (VL) of SEQ ID NO: 43,
  wherein said ScFv is grafted to the N-terminus (BiS2 format) or C-terminus (BiS3 format) of the heavy chain of aslo0543 of SEQ ID NO: 22 or N-terminus ("BiS1 format") of the light chain of SEQ ID NO. 28.

The present invention also provides the antibody or antigen-binding fragment thereof of the invention for use as a medicament.

The present invention also provides an antibody or antigen-binding fragment thereof of the invention for use in prevention or treatment of a disease of the central nervous system, in particular an α-synucleinopathy. In one embodiment, the α-synucleinopathy is selected from Parkinson's disease (PD), dementia with Lewy bodies (DLB), and multiple system atrophy (MSA). In a preferred embodiment, the α-synucleinopathy is Parkinson's disease (PD).

The present invention also provides the use of an antibody or the antigen-binding fragment thereof of the invention for the manufacture of a medicament for preventing or treating a disease of the central nervous system, in particular an α-synucleinopathy. In one embodiment, the α-synucleinopathy is selected from Parkinson's disease (PD), dementia with Lewy bodies (DLB), and multiple system atrophy (MSA). In a preferred embodiment, the α-synucleinopathy is Parkinson's disease (PD).

The invention also provides a method of treating or preventing disease in a patient, the method comprising administering to the patient an antibody, or antigen-binding fragment thereof of the invention. In one embodiment, the α-synucleinopathy is selected from Parkinson's disease (PD), dementia with Lewy bodies (DLB), and multiple system atrophy (MSA). In a preferred embodiment, the α-synucleinopathy is Parkinson's disease (PD).

In use, the antibody or antigen-binding fragment thereof of the invention is able to treat or prevent disease progression by inhibiting the propagation and spreading of alpha-synuclein in vivo. The antibody or antigen-binding fragment thereof of the invention thus provides a distinct advantage over other therapeutics. The invention also provides a method of slowing or preventing disease progression in a subject in need thereof, comprising administering the antibody or antigen-binding fragment thereof of the invention to the patient.

In one embodiment, said method of treating disease comprises administering a therapeutically effective amount of the antibody or antigen-binding fragment thereof of the invention. In another embodiment, said method of preventing disease or slowing or preventing disease progression comprises administering a prophylactically effective amount of the antibody or antigen-binding fragment thereof of the invention.

The dosage ranges for administration of the antibody or antigen-binding fragment thereof of the present invention are those to produce the desired therapeutic effect. It will be appreciated that the dosage range required depends on the precise nature of the antibody or antigen-binding fragment thereof or composition, the route of administration, the nature of the formulation, the age of the patient, the nature, extent or severity of the patient's condition, contraindications, if any, and the judgement of the attending physician. Variations in these dosage levels can be adjusted using standard empirical routines for optimisation.

Suitable dosages are in the range of 1 to 50 mg per kg of body weight. They may be in the range of 5 to 30 mg/kg, 10 to 25 mg/kg, or 15 to 20 mg/kg. The unit dosage may be administered daily or less frequently, for example, weekly or monthly.

Administration may be effected by repeated administrations of the antibody or antigen-binding fragment thereof of the invention, for a prolonged period of time. Administration can be concurrent or sequential, and can be effected in any order.

The prevention or treatment defined herein may be applied as a sole therapy or may involve, in addition to the antibody or antigen-binding fragment of the invention, administration of other agents or established therapies normally used in the treatment of α-synucleinopathies (such as L-3,4-dihydroxyphenylalanine (L-DOPA), dopamine (receptor) agonists, catechol-O-methyltransferase (COMT) inhibitors, and/or monoamine oxidase type B (MAO-B) inhibitors). The administration of other agents or established therapies may be in combination with, or as an adjunct to, or in conjunction with, the antibody or antigen-binding fragment of the invention and may be by way of simultaneous, sequential or separate dosing of the individual components of the treatment.

The combination treatment may be carried out in any way as deemed necessary or convenient by the person skilled in the art and for the purpose of this specification, no limitations with regard to the order, amount, repetition or relative amount of the compounds to be used in combination is contemplated.

A therapeutically effective amount refers to the amount or the antibody or antigen-binding fragment thereof, which when administered alone or in combination to a patient for treating disease, or at least one of the clinical symptoms of disease, is sufficient to affect such treatment of the disease, or symptom. The therapeutically effective amount can vary depending, for example, on the antibody and/or symptoms of the disease, the age, weight, and/or health of the patient to be treated, and the judgment of the prescribing physician. An appropriate therapeutically effective amount in any given instance may be ascertained by those skilled in the art or capable of determination by routine experimentation. A therapeutically effective amount is also one in which any toxic or detrimental effects of the antibody or the antibody or antigen-binding fragment thereof are outweighed by the beneficial effects.

A "prophylactically effective amount" is any amount of the antibody or the antibody or antigen-binding fragment thereof that, when administered alone or in combination to a patient, inhibits or delays the onset or reoccurrence of disease, or at least one of the clinical symptoms of disease. In some embodiments, the prophylactically effective amount prevents the onset or reoccurrence of the disease entirely. "Inhibiting" the onset means either lessening the likelihood of the onset of disease, or preventing the onset of disease entirely.

The present invention also provides pharmaceutical compositions comprising an antibody, or antigen-binding fragment thereof of the invention. Accordingly, the present invention provides a pharmaceutical composition comprising an antibody or antigen-binding fragment thereof of the invention, together with a pharmaceutically acceptable excipient. Suitable pharmaceutically acceptable excipients may facilitate processing of the active compounds into preparations suitable for pharmaceutical administration.

Pharmaceutical compositions of the invention may be formulated for, but not limited to parenteral delivery, for example intramuscular, subcutaneous or intravenous. Compositions suitable for intramuscular, subcutaneous or intravenous injection include sterile aqueous solutions.

The pharmaceutical composition may take the form of an aqueous solution and may include physiologically compatible buffers such as Hank's solution, Ringer's solution, or physiologically buffered saline. The pharmaceutical composition may additionally or alternatively contain substances which increase the viscosity of the suspension, such as sodium carboxymethyl cellulose, sorbitol, or dextran. The pharmaceutical composition may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the pharmaceutical composition may contain suitable stabilisers or agents which increase the solubility of the compounds to allow for the preparation of highly concentrated solutions.

The present invention provides an isolated nucleic acid molecule encoding the antibody, or antigen-binding fragment thereof of the invention. The present invention also provides a vector comprising the isolated nucleic acid molecule of the invention. The present invention further provides a host cell comprising the vector of the invention.

Antibodies or antigen-binding fragments of the invention are not limited to a particular method of generation or production. Thus, the invention provides antibodies which have been manufactured from a hybridoma that secretes the antibody, as well as antibodies produced from a recombinantly produced cell that has been transformed or transfected with a nucleic acid or nucleic acids encoding the antibody. Such hybridomas, recombinantly produced cells, and nucleic acids form part of the invention.

EXAMPLES

Example 1: Antibody Production

Anti-α-syn specific antibodies were isolated from phage display libraries using a series of selection cycles on recombinant human α-syn ("hu α-syn"), both passively immobilised onto microtitre wells and free in solution. Naïve human single chain Fv (scFv) phage display libraries cloned into a phagemid vector based on the filamentous phage M13 were used for selections (Lloyd et al., Protein Eng Des Sel. (2009), 22(3):159-68; and Vaughan et al., Nat Biotechnol. (1996), 14(3); 309-14; both of which are incorporated herein by reference).

A representative number of individual clones from the selection outputs after two or three rounds of selection described above were screened initially as soluble scFv fragments in periplasmic E. coli extracts (Kipriyanov et al. J Immunol Methods (1997) 200: 69-77; incorporated herein by reference) in a homogeneous FRET (fluorescence resonance energy transfer) HTRF® (Homogeneous Time-Resolved Fluorescence, Cisbio International) assay for binding to soluble human α-synuclein.

An HTRF® assay (FIG. 1) is a homogeneous assay technology that utilises fluorescence resonance energy transfer between a donor and acceptor fluorophore that are in close proximity (Mathis G Clin Chem (1995) 41: 1391-1397; incorporated herein by reference). This assay was used to measure macromolecular interactions by directly or indirectly coupling one of the molecules of interest to a donor fluorophore, e.g. europium (Eu3+) cryptate, and coupling the other molecule of interest to an acceptor fluorophore XL665, (a stable cross linked allophycocyanin). Excitation of the cryptate molecule (at 337 nm) resulted in fluorescence emission at 620 nm. The energy from this emission was transferred to XL665 in close proximity to the cryptate, resulting in the emission of a specific long-lived fluorescence (at 665 nm) from the XL665. The specific signals of both the donor (at 620 nm) and the acceptor (at 665 nm) were measured, allowing the calculation of a 665/620 nm ratio that compensates for the presence of colored compounds in the assay.

Unpurified anti-α-syn scFv samples were tested for binding to biotinylated α-syn. 5 microlitres of a solution containing 40 nM biotinylated human α-syn combined with 0.8 nM streptavidin terbium (Cisbio International, 610SATLB) was added to a 384 well low volume assay plate (Costar, 3676). Next, 10 microlitres of each dilution of antibody test sample was added to plate. Finally 5 microlitres of a solution containing DC anti-myc (Cisbio International, 661MYCDAB) was added to assay plate. All dilutions were performed in assay buffer containing 0.8 M potassium fluoride (BDH 103444T) and 0.1% bovine serum albumin (BSA, Sigma A9576) in Dulbeccos PBS (Invitrogen, 14190185). Assay plates were incubated for 3 hour at room temperature followed by 16 hour at 4° C. before reading time resolved fluorescence at 620 nm and 665 nm emission wavelengths using an EnVision plate reader (Perkin Elmer).

Data were analysed by calculating the 665/620 nm ratio followed by the % Delta F values for each sample. The 665/620 nm ratio was used to correct for sample interference using the equation below:

$$665/620 \text{ nm ratio} = \left(\frac{665 \text{ nm signal}}{620 \text{ nm signal}}\right) \times 10,000$$

The % Delta F for each sample was then calculated using the equation below:

$$DeltaF\ (\%) = \left(\frac{sample665/620 \text{ nm ratio} - negativecontrol665/620 \text{ nm ratio}}{negativecontrol665/620 \text{ nm ratio}}\right) \times 10,000$$

The negative control (non-specific binding) was defined by replacing test sample with non-tagged human or rat α-syn.

The % Delta F values were subsequently used to calculate % specific binding as described in the equation below:

$$\% \text{ specific binding} = \left(\frac{(\text{Sample Delta } F\% - NSB \text{ Delta } F\%)}{(\text{Total binding } DeltaF\% - NSB\ DeltaF\%)}\right) \times 100$$

$IC_{50}$ values were determined using GraphPad Prism software by curve fitting using a four-parameter logistic equation:

$Y = \text{Bottom} + (\text{Top} - \text{Bottom})/(1 + 10\hat{}((\text{Log } EC50 - X)*\text{Hill Slope}))$ X is the logarithm of concentration.
Y is specific binding
Y starts at Bottom and goes to Top with a sigmoid shape.

Single chain Fv clones which bound to human α-syn as unpurified periplasmic extracts were subjected to DNA sequencing (Osbourn et al, Immunotechnology (1996), 2: 181-196; and Vaughan et al., Nat Biotechnol. (1996), 14(3); 309-14; both of which are incorporated herein by reference). Unique scFv were expressed again in bacteria and purified by affinity chromatography (as described in WO 01/66754; incorporated by reference). The potencies of these samples were determined by a titration of the purified preparation for binding to biotinylated human α-syn in the HTRF assay as described above. Purified scFv preparations that exhibited the strongest α-syn interaction were selected for conversion to IgG format.

By titrating antibody in the HTRF assay, clones were ranked for strength of binding to α-syn. The best α-syn binders were analysed further for both kinetics of binding to α-syn ($k_{off}$) as IgGs on an Octet Red biosensor (see method as described in Example 9), as well as for synuclein family member selectivity (human α-syn, β-syn, γ-syn) (see method as described in Example 4) and for cross-reactivity with murine α-syn (see method as described in Example 5).

Example 2: Derivation of aslo0452 ngl-3

A C-terminally reactive α-syn specific clone, asyn0087, was identified by screening for binding to human α-syn in a DELFIA assay (see method as described in Example 4). Asyn0087 binds specifically to human, cynomolgus monkey and rodent α-syn (see method as described in Example 5). Asyn0087 was reverted to the closest possible human germline sequence (Tomlinson VBASE. MRC Centre of Protein Engineering, Cambridge, UK. 1997; incorporated herein by reference) that did not affect potency by standard mutagenesis techniques prior to optimisation. Following germlining, the clone was reassessed for binding to α-syn. No detrimental effects were observed.

Large scFv-phage libraries derived from the lead clone were created by oligonucleotide-directed mutagenesis of the variable heavy (VH) complementarity determining regions (CDR) 2 and 3 and light (VL) chain CDRs 1 and 3 using standard molecular biology techniques as described in Clarkson and Lowman (2004) (Phage display: A practical approach. Oxford: Oxford University Press; incorporated herein by reference). The libraries were subjected to affinity-based phage display selections performed on soluble biotinylated human α-syn in order to select variants with higher affinity for human α-syn. The selections were performed essentially as described previously in above with the exception of lowering the concentration of soluble biotinylated human α-syn for each round of selection performed.

Representative clones from each selection output were screened initially as soluble scFv fragments in periplasmic E. coli extracts in a HTRF assay for their ability to compete for binding to soluble α-syn against the parental α-syn binding clone asyn0087. The performance of each library in these population screens was used to inform which CDR mutagenesis libraries were added together genetically, or 'recombined' to create new libraries, and these recombined libraries were subjected to further rounds of affinity driven selections performed on soluble biotinylated human α-syn.

For both individual and recombined mutagenesis library derived clones, after sequence analysis of positive binders, the clones were expressed and purified as both scFv fragments and IgG and binding to soluble α-syn reconfirmed by the epitope competition HTRF assays. By titrating antibody in the HTRF epitope competition assay clones were ranked by their $IC_{50}$ values for relative improvement of binding to α-syn compared to the parental IgG asyn0087. The best α-syn binders were analysed further for synuclein family member selectivity (human α-syn, β-syn, γ-syn) and for cross-reactivity with cynomolgus and rat α-syn by both either direct binding HTRF assay or epitope competition HTRF assay.

From these iterative rounds of library recombination and screening two potent α-syn specific, cynomolgus and rat α-syn cross-reactive clones were identified, aslo0452 ngl-1 and aslo0467.

Single point mutagenesis was performed on aslo0452 ngl-1 for each of the CDRs where positive improvements in $IC_{50}$ potency had been observed. Each position in the chosen CDR was mutated individually through all 20 possible amino acid residues, and again screened by epitope competition HTRF assay for improved $IC_{50}$ compared to aslo0452 ngl-1 IgG. Multiple residues across four CDRs (H2, H3, L1 and L3) were identified and combined on both aslo0452 ngl-1 and aslo0467, and again assessed by epitope competition HTRF assay for improved $IC_{50}$ compared to aslo0452 ngl-1. From these experiments the two most improved binders were identified as aslo0452 ngl-3 and aslo0543.

FIG. 2 compares the amino acid sequences of the VH and VL regions of asyn0087, aslo0452 ngl-3 and aslo0543.

Example 2.1: Reformatting of scFv to IgG1 TM

Single chain Fv clones with desirable α-syn binding properties were converted to effector function null whole immunoglobulin G1 TM (IgG1 TM) (Oganesyan et al. Acta Crystallogr D Biol Crystallogr. (2008), 64 (Pt 6):700-4; incorporated herein by reference) antibody format essentially as described by Persic et al. (Persic et al, Gene (1997) 187: 9-18; incorporated herein by reference) with the following modifications. An OriP fragment was included in the expression vectors to facilitate use with CHO-transient cells and to allow episomal replication. The variable heavy (VH) domain was cloned into a vector (pEU1.4) containing the human heavy chain constant domains and regulatory elements to express whole IgG1 TM heavy chain in mammalian cells. Similarly, the variable light (VL) domain was cloned into a vector (pEU4.4) for the expression of the human light chain (lambda) constant domains and regulatory elements to express whole IgG light chain in mammalian cells. To obtain IgGs, the heavy and light chain IgG expressing vectors were transfected into CHO-transient mammalian cells (Daramola et al, Biotechnol Prog (2014) 30: 132-141; incorporated herein by reference). IgGs were expressed and secreted into the medium. Harvests were filtered prior to purification, then IgG was purified using Protein A chromatography. Culture supernatants were loaded on a column of appropriate size of Ceramic Protein A (BioSepra) and washed with 50 mM Tris-HCl pH 8.0, 250 mM NaCl. Bound IgG was eluted from the column using 0.1 M Sodium Citrate (pH 3.0) and neutralized by the addition of Tris-HCl (pH 9.0). The eluted material was buffer exchanged into PBS using Nap10 columns (Amersham, #17-0854-02) and the concentration of IgG was determined spectrophotometrically using an extinction coefficient based on the amino acid sequence of the IgG (Mach et al, Anal Biochem (1992) 200: 74-80; incorporated herein by reference). The purified IgG were analyzed for aggregation and degradation purity using SEC-HPLC and by SDS-PAGE.

The rationale for using IgG1 TM as the candidate drug format is to minimise bystander killing due to immune cell and complement activation (i.e., excessive production of C3a which may cause inflammation). Bystander cell killing may be triggered by the potential accumulation of immune complexes formed by the candidate drug and extracellular α-synuclein which has been demonstrated to interact with lipid membranes (Bartels et al., Biophys. J. (2010), 99: 2116-2124; incorporated herein by reference). The IgG1 TM format was chosen as this has been demonstrated to have negligible binding to Fcγ receptors (FcγR) and reduced C1q-mediated complement activation by immune complexes (Oganesyan et al. Acta Crystallogr D Biol Crystallogr. (2008), 64 (Pt 6):700-4; incorporated herein by reference).

To minimise any potential risk of immunogenicity, the frameworks of aslo0452 ngl-3 are as close to the human germline amino acid sequence as is possible without affecting potency. This means that some amino acids in aslo0452 ngl-3, including the Vernier residues (Foote and Winter, J Mol Biol. (1992), 224(2): 487-99; incorporated herein by reference), are not mutated to the closest human germline sequence. For the $V_H$ domain of aslo0452 ngl-3 there is one Vernier residue in the V region that is not mutated to the human germline IGVH3-23 and IGJH6 sequence (FIG. 3C). For the $V_L$ domain of aslo0452 ngl-3 all framework residues match the human germline IGLV5-45 and IGJL2 or IGJL3 sequence (FIG. 3D).

Example 3: Affinity Optimized Anti-α-syn IgG Epitope Confirmation

Recombinant human alpha-, beta-, and gamma-synuclein, recombinant truncated versions of human alpha-synuclein (aa1-60, aa1-95, aa61-140, 96-140, ΔNAC, and NCAP), and mouse alpha-synuclein were obtained from rPeptide LLC. Crude epitope mapping was performed using the commercially available α-syn truncates.

Briefly, one microgram per milliliter of each truncate was coated to a microtitre well overnight at 4° C. After rinsing the wells in PBS, a 1 µg/ml dilution of each anti-α-syn antibody was added. Following 1 h incubation and washing the bound antibody was detected by addition of an anti-human IgG conjugated to either HRP or $Eu^{3+}$. Subsequent to incubation and washing, the appropriate detection substrate was added (TMB or DELFIA Enhancer solution respectively) and the plate read on a microtitre plate reader.

These epitope binding studies revealed that the lead isolate, asyn0087, recognizes an epitope located in the C-terminal region of the α-syn protein between amino acids 102 and 130 (FIG. 4A). Both aslo0452 ngl-3 and aslo0543 maintain their recognition of the same epitope located in the C-terminal region of the α-syn protein between amino acids 102 and 130 as their parental lead isolate asyn0087 (FIG. 4B).

Example 4: Specificity of aslo0452 ngl-3 and aslo0543 for α-syn Relative to Synuclein Family Members Using an Epitope Competition HTRF Assay It is important for an antibody intended to be used in therapeutic applications to be specific for human α-syn, in order to minimize any potential safety risks related to off target interaction with the other synucleins (β-synuclein and γ-synuclein).

The specificity of aslo0452 ngl-3 and aslo0543 for α-syn over the other synuclein family members, β-syn and γ-syn, was determined using the HTRF epitope competition assay that measured the binding of biotinylated human α-syn to the antibody in solution.

α-syn, β-syn and γ-syn were titrated into the assay, and the selectivity of aslo0452 ngl-3 IgG and aslo0543 IgG was assessed by measuring the degree of inhibition of biotinylated human α-syn binding to aslo0452 ngl-3/aslo0543. $IC_{50}$ values were determined by curve fitting the data to a four parameter logistic equation using PRISM 6® software (Graphpad). More sensitive HTRF assays measuring direct binding of IgG to human α-syn, β-syn and γ-syn were also used to confirm α-syn specificity (data not shown). For the negative control, the antibody test sample was replaced with an isotype control antibody or buffer only.

Representative $IC_{50}$ values obtained with α-syn, β-syn and γ-syn proteins in the aslo0452 ngl-3 and aslo0543 HTRF epitope competition assays are shown in FIG. 5. No binding to β-syn and γ-syn was observed at the concentrations tested (up to 5 µM), demonstrating that aslo0452 ngl-3 and aslo0543 are selective for α-syn.

Example 5: Specificity of aslo0452 ngl-3 for Human, Cynomolgus Monkey and Rat α-syn Using a HTRF Epitope Competition Assay In view of therapeutic applications, it is important that the antibody is cross reactive to cynomolgus α-synuclein and desired that it is cross reactive to rat α-synuclein, to within 10-fold of that observed against human α-syn. This is to enable safety studies to be carried out in both cynomolgus monkey and rat species.

The specificity of aslo0452 ngl-3 and aslo0543 for human, cynomolgus monkey and rat α-syn was determined using the HTRF epitope competition assay that measured the binding of biotinylated human α-syn to aslo0452 ngl-3 in solution.

Human, cynomolgus monkey and rat α-syn were titrated into the assay, and the selectivity of the antibody was assessed by measuring the degree of inhibition of biotinylated human α-syn binding to the antibody. $IC_{50}$ values were determined by curve fitting the data to a four parameter logistic equation using PRISM 6® software (Graphpad). Species cross reactivity of aslo0452 ngl-3 and aslo0543 was also confirmed using a direct binding HTRF assay format (not shown). Aslo0452 ngl-3 (or aslo0543) was titrated into the assay to compete for human or cynomolgus monkey or rat α-syn binding to aslo0452 ngl-3 (or aslo0543) by HTRF assay. For the negative controls, the antibody test sample was replaced with an isotype control antibody or buffer only.

Representative $IC_{50}$ values obtained with human, cynomolgus monkey and rat α-syn proteins in the HTRF epitope competition assay are shown in FIG. 6. Aslo0452 ngl-3 binds to human and cynomolgus α-syn with $IC_{50}$ values of 5.7 nM and 6.8 nM respectively, and binds to rat α-syn with $IC_{50}$ value of 19.6 nM, within 4-fold. Aslo0543 binds to human and cynomolgus α-syn with $IC_{50}$ values of 2.0 nM and 2.1 nM respectively, and binds to rat α-syn with $IC_{50}$ value of 3.8 nM, within 2-fold.

The ability of aslo0452 ngl-3 to bind to human, cynomolgus monkey and rat α-syn is indicative of binding to a different epitope on human alpha-synuclein as compared to antibodies that do not bind to human, and cynomolgus monkey and rat α-syn.

Example 6: Specificity of Affinity Optimized Clones for Native α-syn Measured by Flow Cytometry The specificity of the affinity optimized anti-α-syn IgGs, aslo0452 ngl-3 and aslo0543, for binding to native, endogenous human α-syn was determined by flow cytometry using α-syn positive and negative cell lines.

Briefly, SHSY5Y neuroblastoma cells (α-syn positive) and BT-20 breast cancer cells (α-syn negative) were fixed in 0.01% formaldehyde and then permeabilised with 0.5% (v/v) Tween 20 prior to incubation with anti-α-syn antibodies, positive control or isotype control antibodies. After extensive washes, bound antibody was detected by incubation with an anti-human or anti-mouse IgG-FITC secondary antibody. Following further washes the cells were analyzed with a FACS Canto II apparatus (Becton Dickinson, Franklin Lakes, N.J.) and data analysis was performed using FlowJo Software (Tree Star, Ashland, Oreg.).

Data are plotted as histograms showing the difference between cells stained alone versus primary antibody stained cells. The results in FIG. 7A show a shift in fluorescent signal in the presence of asyn0087 (panel D) in α-syn positive SH-SY5Y cells, compared to isotype control and secondary antibody alone (panel B), indicating recognition of endogenously expressed α-syn. Asyn0087 does not bind to the α-syn negative human breast cancer cell line, BT-20 (panel C). The results in FIG. 7B show a strong shift in fluorescent signal in the presence of either aslo0452 ngl-3 or aslo0543 (panel H) comparable to the positive control antibody, 4D6 on α-syn positive SH-SY5Y cells (panel F) and no shift on α-syn negative BT-20 cells (panel G). This demonstrates that both aslo0452 ngl-3 and aslo0543 bind to native, endogenously expressed intracellular human α-syn.

Example 7: Specificity of Optimized anti-α-syn IgGs for Aggregated Human α-syn by DELFIA ELISA Fibrillar preparations or aggregates of human α-syn were generated as described by Emadi et al. (Emadi et al, Bio-chemistry (2004), 43: 2871-2878; incorporated herein by reference). Briefly, 200 μl of 50 μM recombinant α-syn was aliquoted into a 1.8 ml Sarstedt tube and placed in a 37° C. shaking incubator for 3 days at 280 rpm. The presence of aggregated α-syn was determined by incorporation of Thioflavin T added to a final concentration of 10 μM, incubated in the dark for 1 h at room temperature and fluorescence read at an excitation wavelength of 450 nm and emission wavelength of 485 nm on an Envision microplate reader.

The specificity of the affinity optimized anti-α-syn IgGs, aslo0452 ngl-3 and aslo0543, and the lead antibody asyn0087, for aggregated human α-syn was determined using a DELFIA® antibody capture assay. This assay measured the capture of aggregated human α-syn by aslo0452 ngl-3, aslo0543 or asyn0087 in a pair-wise ELISA. Briefly, a mouse IgG1 version of the anti-α-syn antibody was immobilized onto the well of a 96-well microtitre plate (Nunc). After blocking, aggregated or monomeric human α-syn was incubated in the wells. Following washing, captured human α-syn was detected by addition of the human IgG1 TM version of the same anti-α-syn antibody and subsequently an anti-human IgG-Europium conjugate (Perkin Elmer) or anti-human IgG-HRP conjugate. Subsequent to incubation and washing, the appropriate detection substrate was added (TMB or DELFIA Enhancer solution respectively) and the plate read on a microtitre plate reader.

In this assay, only aggregated human α-syn will be captured and detected since it presents multiple copies of the same epitope on a single aggregate. For monomeric α-syn only one epitope copy is present, therefore the detecting second antibody cannot bind in the presence of the capture antibody. The data are summarized in FIG. 8. The lead isolate, asyn0087, is able to bind to aggregated recombinant human α-syn. Thus the epitope to which asyn0087 binds is not itself involved in aggregation of α-syn. Both aslo0452 ngl-3 and aslo0543 retained their ability to bind to aggregated recombinant human α-syn.

Example 8: Specificity of Optimized anti-α-syn IgGs in Disease Relevant Tissues by Immunohistochemistry The specificity of the affinity optimized anti-α-syn IgGs, aslo0452 ngl-3 and aslo0543, and the lead antibody asyn0087, for disease relevant forms of human α-syn was determined by immunohistochemical staining of Parkinson's disease brain tissue. The results are shown in FIG. 9 and demonstrate that like asyn0087, both aslo0452 ngl-3 and aslo0543 can recognize disease relevant pathological forms of human α-syn in Parkinson's disease brain tissue sections, including Lewy bodies, Lewy neurites, neuronal aggregates, Lewy dots and background brain tissue. No non-specific staining was observed in normal or healthy brain tissue.

Example 9: Anti-α-syn Antibody Affinity Determination

The equilibrium dissociation constants ($K_D$) for anti-α-syn IgGs for human α-syn was determined using two platform technologies: Octet Red (Forte Bio) and KinExA (Sapidyne Instruments).

Both assay systems showed good agreement, indicating that aslo0452 ngl-3 affinity was in the sub-nanomolar range. Table 1 shows the affinity measurements derived for key anti-α-syn clones generated throughout the lead isolation and lead optimisation process.

Example 9.1: Affinity of aslo0452 ngl-3 by Octet

The affinity of aslo0452 ngl-3 IgG for recombinant bacterially expressed monomeric human avi-tag α-syn-Flag-His was estimated using an Octet Red instrument. Aslo0452 ngl-3 was pre-mixed with varying concentrations of each ligand until equilibrium was reached. The amount of free antibody was then measured using the Octet by capturing free aslo0452 ngl-3 using biotinylated α-syn immobilized onto streptavidin coated sensors. The amount of free antibody detected at each α-syn concentration was plotted against the concentration of ligand and the KinExA software was used to calculate the equilibrium dissociation constant ($K_D$). The results shown in Table 1 demonstrate that aslo0452 ngl-3 IgG binds to human α-syn with an affinity of 106 pM.

Example 9.2: Affinity of aslo0452 ngl-3 by KinExA

In addition, the solution phase affinity ($K_D$) of aslo0452 ngl-3 IgG for recombinant bacterially expressed monomeric human biotinylated α-syn was determined using a KinExA instrument (Sapidyne Instruments). Aslo0452 ngl-3 was pre-mixed with varying concentrations of each ligand until equilibrium was reached. The amount of free antibody was then measured using the KinExA by capturing free aslo0452 ngl-3 using α-syn coated beads, washing away unbound material and detecting bound antibody using a fluorescently labelled species specific antibody. The amount of free antibody detected at each α-syn concentration was plotted against the concentration of ligand and the KinExA software was used to calculate the equilibrium dissociation constant ($K_D$). The results shown in Table 1 demonstrate that aslo0452 ngl-3 IgG binds to α-syn with an affinity of 74 pM, showing good agreement with the Octet solution phase affinity assay above.

Example 9.3: Affinity of aslo0452 ngl-3 Fab Fragment by KinExA

The aslo0452 ngl-3 Fab fragment binds α-synuclein with a high affinity. The $K_D$ value of aslo0452 ngl-3 Fab fragment for α-synuclein, as measured by KinExA analysis (as described in the above example for the full antibody), is 174 pM (95% CI: 15-177 pM).

Example 10: Effects of aslo0452 ngl-3 on Free Unbound α-synuclein Levels in the Prefrontal Cortex Interstitial Fluid (ISF) of Male Sprague Dawley Rats Adult male Sprague Dawley rats (293-417 g; Harlan, the Netherlands) were anesthetized and guides were implanted in the prefrontal cortex.

One day before the experiment push pull probes (1-3 MDa polyethylene membrane 4 mm) were implanted in the prefrontal cortex using a stereotaxic frame (coordinates for the probes: AP=−3.4 mm (to bregma), lateral+0.8 mm (to midline), ventral−5.0 mm (to dura), the incisor bar was set at −3.3 mm (all coordinates according to Paxinos and Watson. The rat brain in stereotaxic coordinates, Academic Press, New York, 6th edition 2008). The probes were attached to the skull with a stainless steel screw and dental cement.

On the day of the experiment the push pull microdialysis probes were connected with flexible PEEK tubing (Western Analytical Products Inc. USA; PK005-020) to a microperfusion pump (Harvard) and perfused with artificial CSF (perfusate), containing 147 mM NaCl, 3.0 mM KCl, 1.2 mM CaCl2, and 1.2 mM MgCl2+0.2% BSA at a flow rate of 0.5 µL/min. The outlets of the probes were connected to flexible FEP tubing. After a minimum of two hours of pre-stabilization, aslo0452 ngl-3 formulated in PBS or PBS only (vehicle) were dosed at 30 or 0 mg/kg, respectively. The compound was administered at 2 mL/kg intravenously. Microdialysis samples were collected at 120 minute intervals. Samples were collected into mini-vials (Microbiotech/se AB, Sweden; 4001029). All samples were stored at −80° C.

To determine free α-synuclein concentration in rat ISF the microdialysis samples were first subjected to immunoprecipitation to remove aslo0452 ngl-3. The immunoprecipitation co-precipitates α-synuclein bound to therapeutic antibodies, while unbound "free" α-synuclein remains in the supernatant. A solution of protein A beads (Dynabeads® Protein A) was added to a 96-well non-skirted plate (polypropylene 0.2 mL) and washed twice with TBST (50 mM TBS plus 0.1% Tween 20) using a magnet (DynaMag™96 side) to separate the beads from the solution. Thawed rat ISF microdialysis samples (10 or 20 µL) were added to each well, mixed with beads by pipetting up and down and incubated at 4° C. with tilt rotation for 10 minutes. The beads were then pelleted using the magnet twice to ensure complete removal of the beads. The immunoprecipitated ISF samples were transferred to a 96 well plate from an anti-α-synuclein ELISA kit (Sensolyte™ Quantitative ELISA kit, human/mouse/rat, AnaSpec, US, AS-55550) with sample diluent buffer already added to a total volume of 100 µL. Calibration samples, 100 µL per well, were added to the plate in duplicate and 50 µL of detection antibody working solution was added to each well. The plate was incubated at +4-8° C. overnight while shaking and protected from light and then washed six times with 350 µL of wash buffer. Finally, 100 µl of TMB colour substrate was added to each well and the plate was incubated in 10-15 minutes at room temperature in the dark. To stop the reaction, 50 µL of Stop Solution was added to each well and the plate was read within 2 hours at an absorbance of 450 nm. Quantification was performed by plotting the response of the standard curve as absorbance units on the linear scale versus concentration on the logarithmic scale. A four-parameter function was used for curve fitting.

A time dependent decrease of free α-synuclein was demonstrated in ISF (FIG. 10) after a single intravenous aslo0452 ngl-3 administration of 30 mg/kg.

Example 11: Effects of aslo0452 ngl-3 on Free Unbound α-synuclein Levels in the CSF of Male Sprague Dawley Rats Adult male Sprague Dawley rats were anesthetized and catheters were placed in the cisterna magna to accommodate CSF sampling. A 0.8 cm indwelling cannula was inserted into the cisterna magna, and exteriorized through an incision on top of the skull. The end of the CSF catheter was fixed in position with dental acrylic cement and attached to the skull with three stainless steel screws. The animals were allowed a minimum of 2 days of recovery before the compound was administered.

Aslo0452 ngl-3 was formulated in buffer for dosing at 3, 10, 30 or 100 mg/kg. The compound or vehicle only was administered at 2 mL/kg intravenously.

After collection of at least four clean CSF samples taken over a minimum of two days, the compound was administered. All animals were dosed with either aslo0452 ngl-3 or vehicle on day "0". CSF samples were collected at each indicated time point. All samples were stored at −80° C. until shipment.

To determine free α-synuclein in CSF, α-synuclein bound to aslo0452 ngl-3, is removed by immunoprecipitation (IP) prior to analysis. The IP will co-precipitate α-synuclein bound to therapeutic antibodies, while unbound "free" α-synuclein remains in the supernatant. Determination of free levels of α-synuclein in supernatant is performed using a commercial ELISA kit obtained from Anaspec. The analysis was performed as described for the ISF-results (as described in Example 10).

A dose and time dependent decrease of free α-synuclein was demonstrated in CSF (FIG. 11) after a single intravenous aslo0452 ngl-3 administration in the dose range 3-100 mg/kg.

Example 12: Functional Characterisation of aslo0452 ngl-3 by Reduction of Alpha-synuclein Spreading in a Lentiviral In Vivo Model of Alpha-synucleinopathy The ability of a high affinity anti-alpha-synuclein antibody, aslo0452 ngl-3, to block the spreading of alpha-synuclein was investigated using a lentiviral in vivo mouse model of alpha-synucleinopathy. For this purpose, both non-transgenic wild-type mice (non-tg) and alpha-synuclein overexpressing transgenic mice (α-syn tg) were injected with a lentiviral vector that expresses alpha-synuclein (LV-α-syn) into the right hippocampus, and were then passively immunised weekly for 13 weeks with anti-alpha synuclein mouse IgG1 antibodies including aslo0452 ngl-3, and an isotype control mouse IgG1 NIP228. At the end of the immunisation period the mice were euthanised and their brains were fixed in 4% PFA, then coronally sectioned and analysed by immunocytochemistry with automated image analysis for levels of alpha-synuclein immunoreactivity ipsilateral and contralateral to the site of the LV-α-syn injection.

Surgery and Passive Immunisation

Three-to-four month old non-transgenic wild type mice (non-tg; n=40) and alpha-synuclein transgenic mice (α-syn tg; n=40) received a single unilateral injection into the right hippocampus (−2.0, 1.5, −1.3 from Bregma) of a lentiviral vector expressing alpha-synuclein (LV-α-syn). Two weeks after the LV-α-syn injection surgery, mice received weekly doses of anti-alpha-synuclein mouse IgG1 antibodies: aslo0452 ngl-3 (non-tg n=10; α-syn tg n=10), aslo0452 ngl-3 D265A (non-tg n=10; α-syn tg n=10), 9E4 (non-tg n=10; α-syn tg n=10), or they were dosed with NIP228 isotype control mouse IgG1 (non-tg n=10; α-syn tg n=10).

All mouse IgGs were dosed at 20 mg/kg by the intraperitoneal (IP) route for 13 weeks. Animals were group-housed with a maximum or 4 per cage. Animals were kept on 12/12 light/dark cycle with access to food and water ad libitum. Cages were changed once a week and monitored daily. Any adverse events were reported. All animals tolerated the surgical procedures as well as the immunisations. At the end of the antibody treatment period, mice were euthanised following guidelines for the humane treatment of animals and their brains were serially sectioned in the coronal axes and assessed for neuropathological analysis of alpha-synuclein spreading by immunocytochemical methods.

Alpha-synuclein Immunocytochemistry

Brains were removed, fixed in 4% paraformaldehyde, and sections cut at 40 µm intervals in the coronal axes using a vibratome and stored at −30° C. in cryoprotective medium (30% glycerin, 30% ethylene glycol, 40% PBS). Following PBS washes, and blocking buffer steps, sections were incubated overnight at 4° C. with primary antibody (anti-alpha-synuclein mAb SYN-1 from BD at a dilution of 1:500), washed in PBS and incubated for 1 hour at room temperature with secondary antibody (biotinylated anti-mouse IgG from Vector Laboratories at a dilution of 1:100). Following final PBS wash steps, alpha-synuclein staining was localised using the avidin/biotin-peroxidase complex detection system (Elite ABC, Vector Laboratories). Sections were then analysed with automated image analysis for levels of alpha-synuclein ipsilateral and contralateral to the site of the lentiviral vector (LV-α-syn) injection.

Statistics

Data generated from the automated image acquisition of alpha-synuclein levels across non-tg and α-syn tg treatment groups were analysed using GraphPad Prism Software, San Diego Calif., USA. One way ANOVA was performed with Dunnett's Multiple Comparison post-test. Data shown in figures is presented as mean±standard error of mean (SEM). Differences between groups were considered to be of statistical significance when $p<0.05$. All analyses were performed blinded to the rater. The antibody treatment groups were also blinded to the rater.

Results

In both non-tg mice and α-syn tg mice, alpha-synuclein immunoreactivity on the LV-α-syn-injected ipsilateral side was intense in the neuropil and covered most of the surface of the hippocampus (FIG. 12A, FIG. 15A; NIP228—Ipsilateral). The contralateral non-injected hippocampus of non-tg mice and α-syn tg mice also displayed high levels of alpha-synuclein immunoreactivity, indicating that the lentivirally-expressed alpha-synuclein had spread from the injected right hippocampus to the left hippocampus (FIG. 12A, FIG. 15A; NIP228—Contralateral). In this lentiviral alpha-synuclein injection mouse model, previous experiments have shown that only expressed alpha-synuclein protein spreads to the contralateral side with no evidence of transfer of the lentivirus itself, as determined by PCR analysis (data not shown).

The ipsilateral and contralateral hippocampal levels of lentivirally-expressed alpha-synuclein in non-tg mice that were passively immunised with 9E4 antibody (9E4—mouse version of PRX002 (Prothena)) were almost identical to the ipsilateral and contralateral hippocampal levels of lentivirally-expressed alpha-synuclein in non-tg mice that were passively immunised with NIP228 isotype control mouse IgG1 (FIG. 12 A,B,C; 9E4 compared with NIP228), indicating that 9E4 when dosed at 20 mg/kg weekly for 13 weeks via the IP route does not block the dissemination of alpha-synuclein in this alpha-synuclein spreading model.

In contrast, both the ipsilateral and contralateral hippocampal levels of lentivirally-expressed alpha-synuclein in non-tg mice that were passively immunised with either aslo0452 ngl-3 antibody or an effector null mutant version of aslo0452 ngl-3 (aslo0452-ngl-3-D265A), where replacement of aspartic acid by alanine at position 265 (D265A) in the mouse IgG1 results in loss of interaction between this isotype and low-affinity IgG Fc receptors (FcγRIIB and FcγRIII) found on microglia, were highly significantly lower than the ipsilateral and contralateral hippocampal levels of lentivirally-expressed alpha-synuclein in non-tg mice that were passively immunised with NIP228 isotype control mouse IgG1 (FIG. 12 A,B,C; aslo0452-ngl-3 & aslo0452-ngl-3-D265A compared with NIP228). This indicates that passive immunisation of mice with either aslo0452-ngl-3 or the effector null D265A mutant version of aslo0452-ngl-3 robustly blocks the spreading of alpha-synuclein in this mouse model of alpha-synucleinopathy. Similar results were obtained when the LV-α-syn vector was injected into the right hippocampus of α-syn tg mice; passive immunisation with aslo0452-ngl-3 or aslo0452-ngl-3-D265A but not 9E4 led to a robust and statistically significant reduction in both the ipsilateral and contralateral levels of alpha-synuclein immunoreactivity in the hippocampus when compared to NIP228-treated α-syn tg mice (FIG. 15 A,B,C).

At higher magnification lentivirally-expressed alpha-synuclein immunoreactive deposits were observable along both ipsilateral axons of the injected side and contralateral axons of the non-injected side of non-tg mice (FIG. 13 A; black arrows showing trans-hippocampal axons), suggesting that alpha-synuclein spreading to the contralateral hippocampus may principally occur along axons (trans-axonal spreading). The ipsilateral and contralateral levels of axonal alpha-synuclein deposits in non-tg mice passively immunised with either 9E4 antibody or NIP228 isotype control mouse IgG1 were not significantly different (FIG. 13 A,B,C; 9E4 compared with NIP228), indicating that under our experimental conditions, 9E4 does not impact the levels of axonal alpha-synuclein deposits nor does it reduce the dissemination of alpha-synuclein along axons in this lentiviral-alpha-synucleinopathy spreading model.

In contrast, both the ipsilateral and contralateral levels of axonal alpha-synuclein deposits in non-tg mice passively immunised with either aslo0452 ngl-3 antibody or the effector null mutant version of aslo0452-ngl-3 (aslo0452-ngl-3-D265A), were significantly lower than the levels of axonal alpha-synuclein deposits in non-tg mice treated with NIP228 isotype control mouse IgG1 (FIG. 13 A,B,C; aslo0452-ngl-3 & aslo0452-ngl-3-D265A compared with NIP228), indicating that passive immunisation of mice with either aslo0452-ngl-3 or the effector null D265A mutant version of aslo0452-ngl-3 clears axonal alpha-synuclein deposits and robustly blocks the ipsilateral-to-contralateral transfer of alpha-synuclein along axons in this lentiviral-alpha-synucleinopathy mouse model.

Very similar results were obtained when the LV-α-syn vector was injected into the right hippocampus of α-syn tg mice; passive immunisation with aslo0452-ngl-3 or aslo0452-ngl-3-D265A but not 9E4 led to a robust and statistically significant reduction in both the ipsilateral and contralateral levels of alpha-synuclein immunoreactivity along axons when compared to NIP228-treated α-syn tg mice (FIG. 16 A,B,C).

In LV-α-syn-injected non-tg mice, at higher magnification intense alpha-synuclein immunoreactivity was detected in the neuropil of the ipsilateral hippocampus and to a lesser extent in the neuropil of the ipsilateral neocortex (FIG. 14 A). In addition, intense deposits of alpha-synuclein were detected in a number of identifiable neuronal cell bodies (soma) in the CA1 region of the ipsilateral hippocampus and weaker alpha-synuclein immunoreactivity was detected in layer 5 neurons of the ipsilateral neocortex (FIG. 14; black arrows). While treatment with 9E4 antibody did not significantly alter the number of ipsilateral CA1 hippocampal neurons or ipsilateral layer 5 neocortical neurons containing alpha-synuclein deposits when compared to non-tg mice immunised with NIP228 isotype control mouse IgG (FIG. 14 A,B,C; 9E4 compared with NIP228), non-tg mice treated with either aslo0452 ngl-3 antibody or an effector null mutant version of aslo0452-ngl-3 (aslo0452-ngl-3-D265A) had significantly reduced numbers of ipsilateral CA1 neurons and ipsilateral layer 5 neurons containing alpha-synuclein deposits compared to NIP228 isotype control mouse IgG-treated non-tg mice (FIGS. 14 A,B,C; aslo0452-ngl-3 & aslo0452-ngl-3-D265A compared with NIP228).

Also, the intensity of alpha-synuclein immunoreactivity in the neuropil and neurons of the ipsilateral CA1 region of the hippocampus and ipsilateral layer 5 region of the neocortex was noticeably lower in aslo0452-ngl-3-treated and aslo0452-ngl-3-D265A-treated non-tg mice compared to NIP228 isotype control mouse IgG-treated non-tg mice (FIG. 14A; aslo0452-ngl-3 & aslo0452-ngl-3-D265A compared with NIP228).

Figure 17A:
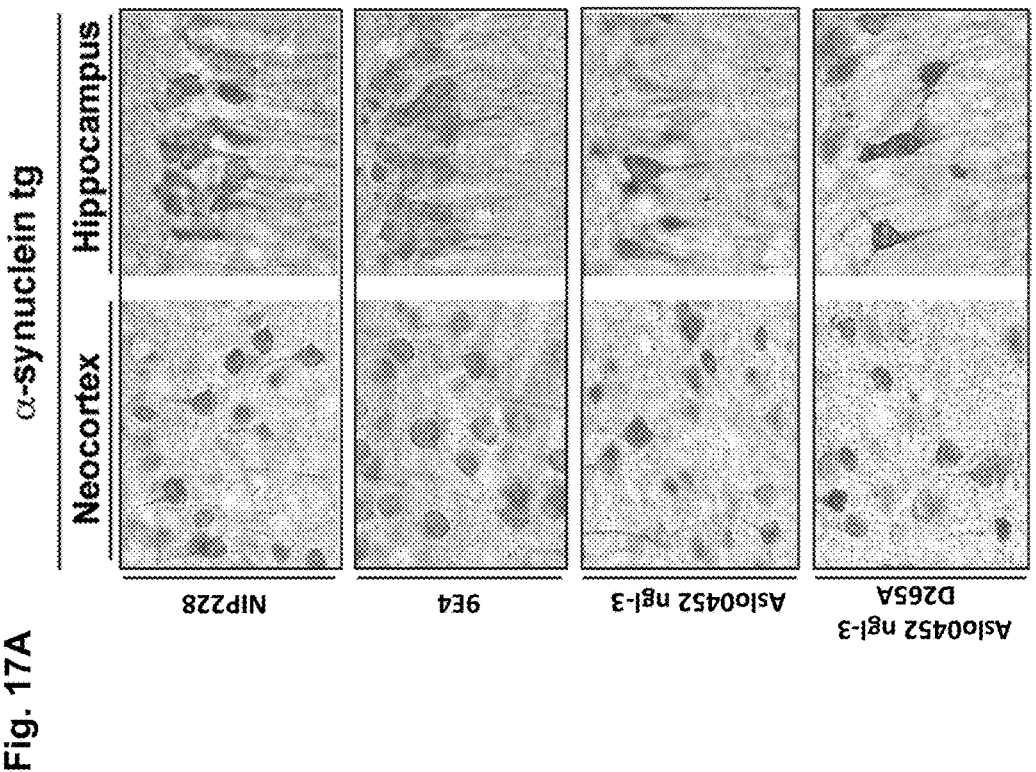
Figure 17B:
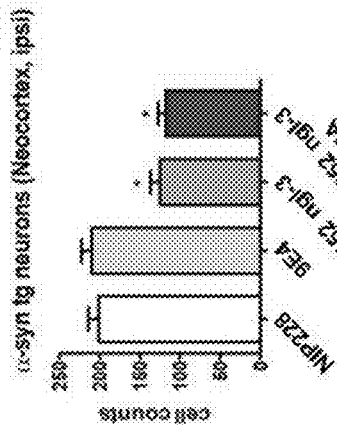
Figure 17C:
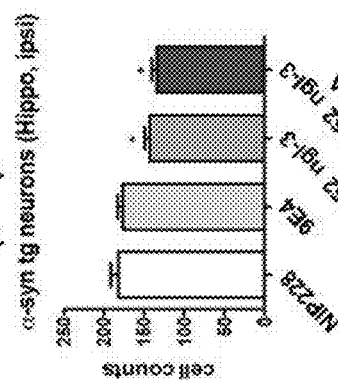
Figure 17D:
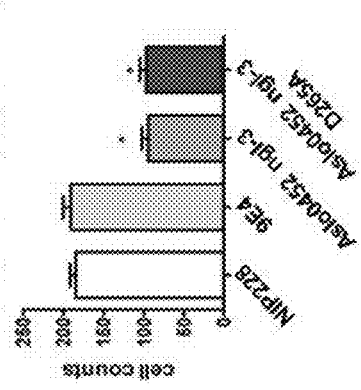

Similar results were obtained when the LV-α-syn vector was injected into the right hippocampus of α-syn tg mice; treatment with aslo0452-ngl-3 or aslo0452-ngl-3-D265A but not 9E4 led to a statistically significant decrease in the numbers of neurons containing strong alpha-synuclein immunoreactivity in the ipsilateral CA1 hippocampal and layer 5 neocortical regions, as well as in the contralateral CA1 hippocampal region, when compared to NIP228-treated α-syn tg mice (FIG. 17A, B, C, D).

It has been demonstrated that passive immunisation of either non-tg wild type mice or α-syn tg mice that have both been stereotactically injected with a lentiviral vector that drives expression of human alpha-synuclein on one side of the hippocampus, with a high affinity anti-alpha-synuclein mouse IgG1 antibody aslo0452-ngl-3 robustly reduces the ipsilateral-to-contralateral trans-axonal spreading of lentivirally expressed alpha-synuclein that is observed in this mouse model of alpha-synuclein propagation. This newly disclosed anti-alpha-synuclein antibody's property of inhibiting alpha-synuclein spreading in vivo is indicative of binding to a different epitope of human alpha-synuclein as compared to antibodies that do not inhibit spreading in the model tested, e.g. 9E4 antibody.

Furthermore, the data showing that an effector null D265A mutant version of aslo0452-ngl-3 is equally effective as aslo0452-ngl-3 at reducing alpha-synuclein spreading in the model indicates that antibody-mediated prevention of alpha-synuclein spreading does not require Fc-associated effector functions as a key mechanism of action, and in particular it indicates that there appears to be no requirement or role for Fc receptors (FcγRIIB and FcγRIII) present on microglia in the antibody-mediated blockade of alpha-synuclein spreading.

In summary, the antibodies of the invention that target alpha-synuclein, as well as the antigen-binding fragment thereof, have the potential to be disease-modifying in PD or DLB or MSA by blocking or slowing the pathological uptake of alpha-synuclein into recipient cells and preventing seeding and transmission of alpha-synuclein pathology between anatomically connected brain regions. In this way, antibodies targeting alpha-synuclein may treat or prevent disease progression and be of therapeutic benefit to patients with synucleinopathies such as PD, DLB or MSA.

Example 13: Generation of 0452 ngl-3-BBBt0626gl Bispecific Antibodies

Exemplary bispecific antibodies according to the invention comprising the human IgG1 TM backbone associated with a single chain fragment (scFv) of BBBt0626gl, grafted to the N-terminus (Bis2 format) or C-terminus (Bis3 format) of the heavy chain of aslo0452 ngl-3 were generated as described below.

A bispecific antibody according to the invention, in a Bis2 format, was generated by synthetically producing a DNA fragment encoding Bbbt0626glscFv-(G4S)x2-aslo0452 ngl-3 VH or Bbbt0626wt-(G4S)x2-aslo452 ngl-3 VH that contained BssHII and BstEII flanking endonuclease restriction sites, upstream of Bbbt0626glscFv or Bbbt0626wt and downstream of aslo0452 ngl-3 VH, respectively. The digested DNA fragments were then directionally cloned into the hIgG1TM vector backbone.

A bispecific antibody according to the invention, in a Bis3 format was generated by PCR amplification followed by directional cloning using restriction endonuclease sites (SfiI and XbaI). Two PCR fragments were generated: (1) amplifying the hIgG1TM-CH3 domain from the SfiI restriction site to the C-terminal end of the CH3 domain and (2) an over lapping PCR fragment with a forward PCR oligo incorporating the C-terminal end of the CH3-(G4S)x3 linker (SEQ ID NO: 57) and the N-terminal end of the Bbbt0626gl scFv along with an oligo amplifying the C-terminal end of the Bbbt0626gl scFv and immediate downstream vector sequence past the XbaI restriction site. Both PCR fragments were stitched together in a pull-through PCR reaction and subsequently directionally cloned into the pEU1_4 (human IgG1TM vector) via the SfiI and XbaI restriction endonuclease sites.

These bispecific antibodies were expressed in a CHO based expression system and the resulting antibodies purified via protein A column purification. All Bbbt0626 derived bispecific antibodies were tested for in vitro binding to mouse brain endothelial cell-line (b.end3) to confirm binding activity of the BBB transporter moiety and also tested for competition of binding of also0452 ngl-3 in an HTRF based epitope competition assay to confirm binding to the aslo0452 ngl-3 epitope.

The invention claimed is:

1. An antibody or antigen-binding fragment thereof that binds human α-synuclein, wherein the antibody or antigen-binding fragment thereof comprises:
   a) three heavy chain CDRs having sequences:
   (i) H-CDR1 of SEQ ID NO: 25,
   (ii) H-CDR2 of SEQ ID NO: 26, and
   (iii) H-CDR3 of SEQ ID NO: 27, and
   b) three light chain CDRs having sequences:
   (i) L-CDR1 of SEQ ID NO: 31,
   (ii) L-CDR2 of SEQ ID NO: 32 and
   (iii) L-CDR3 of SEQ ID NO: 33.

2. The antibody or antigen-binding fragment thereof, according to claim 1, wherein the antibody or antigen-binding fragment thereof is an IgA, IgD, IgE, IgM, IgG1, IgG2, IgG3 or IgG4 antibody or antigen-binding fragment thereof.

3. The antibody or antigen-binding fragment thereof, according to claim 1, wherein the antibody or antigen-binding fragment thereof is an IgG1 antibody or antigen-binding fragment thereof that comprises a L234F/L235E/P331S triple mutation in the Fc region.

4. The antibody or antigen-binding fragment thereof, according to claim 1, wherein the antibody or antigen-binding fragment thereof competes with antibody aslo0452 ngl-3 for binding to human α-synuclein.

5. The antibody or antigen-binding fragment thereof, according to claim 1, wherein the antibody or antigen-binding fragment thereof binds to the same epitope on human α-synuclein as antibody aslo0452 ngl-3.

6. The antibody or antigen-binding fragment thereof according to claim 1, wherein the antibody or antigen-binding fragment thereof is fused with a transporter molecule for delivery across the blood-brain barrier (BBB).

7. The antibody or antigen-binding fragment thereof according to claim 6, wherein the transporter molecule is
   a) an immunoglobulin-derived polypeptide comprising BBBt0626gl or a blood-brain barrier-penetrable fragment thereof, or
   b) BBBt0626 or a blood-brain barrier-penetrable fragment thereof, or
   c) or BBBt0632gl or a blood-brain barrier-penetrable fragment thereof.

8. The antibody or antigen-binding fragment thereof according to claim 7, wherein the transporter molecule is a single chain fragment (scFv) comprising:
   (i) the heavy chain variable region (VH) of BBBt0626gl of SEQ ID NO: 39 and the light chain variable region (VL) of BBBt0626gl of SEQ ID NO: 43, or
   (ii) the heavy chain variable region (VH) of BBBt0626 of SEQ ID NO: 47 and the light chain variable region (VL) of BBBt0626 of SEQ ID NO: 43, or
   (iii) the heavy chain variable region (VH) of BBBt0632gl of SEQ ID NO: 48 and the light chain variable region (VL) of BBBt0632gl of SEQ ID NO: 52.

9. The antibody or antigen-binding fragment thereof of claim 1, wherein the antibody or antigen-binding fragment thereof binds to human α-synuclein with a $K_D$ of less than 500 pM.

10. The antibody or antigen-binding fragment thereof of claim 1, wherein the antibody or antigen-binding fragment thereof reduces cell to cell transfer of α-synuclein in vivo.

11. The antibody or antigen-binding fragment thereof of claim 1, wherein the antibody or antigen-binding fragment thereof binds human α-synuclein but not human β-synuclein or human γ-synuclein.

12. The antibody or antigen-binding fragment thereof of claim 1, wherein the antibody or antigen-binding fragment thereof binds to human, rat and cynomolgus α-synuclein.

13. The antibody or antigen-binding fragment thereof of claim 1, wherein the antibody or antigen-binding fragment thereof binds to native endogenous human α-synuclein.

14. The antibody or antigen-binding fragment thereof of claim 1, wherein the antibody or antigen-binding fragment thereof binds to aggregates of human α-synuclein.

15. The antibody or antigen-binding fragment thereof of claim 1, wherein the antibody or antigen-binding fragment thereof binds pathological forms of α-synuclein.

16. The antibody or antigen-binding fragment thereof of claim 1, wherein the antibody or antigen-binding fragment thereof reduces α-synuclein levels in the brain interstitial fluid and/or in the cerebrospinal fluid.

17. The antibody or antigen-binding fragment thereof of claim 1, wherein the antibody or antigen-binding fragment thereof comprises a variable heavy chain region comprising an amino acid sequence that is at least 90% identical to the amino acid sequence of SEQ ID NO: 24.

18. The antibody or antigen-binding fragment thereof of claim 1, wherein the antibody or antigen-binding fragment thereof comprises a variable heavy chain region comprising an amino acid sequence that is at least 95% identical to the amino acid sequence of SEQ ID NO: 24.

19. The antibody or antigen-binding fragment thereof of claim 1, wherein the antibody or antigen-binding fragment thereof comprises a variable heavy chain region comprising the amino acid sequence of SEQ ID NO: 24.

20. The antibody or antigen-binding fragment thereof of claim 1, wherein the antibody or antigen-binding fragment thereof comprises a variable light chain region comprising an amino acid sequence that is at least 90% identical to the amino acid sequence of SEQ ID NO: 30.

21. The antibody or antigen-binding fragment thereof of claim 1, wherein the antibody or antigen-binding fragment thereof comprises a variable light chain region comprising an amino acid sequence that is at least 95% identical to the amino acid sequence of SEQ ID NO: 30.

22. The antibody or antigen-binding fragment thereof of claim 1, wherein the antibody or antigen-binding fragment thereof comprises a variable light chain region comprising the amino acid sequence of SEQ ID NO: 30.

23. The antibody or antigen-binding fragment thereof of claim 1, wherein the antibody or antigen-binding fragment thereof is an antibody.

24. The antibody or antigen-binding fragment thereof of claim 1, wherein the antibody or antigen-binding fragment thereof comprises a L234F/L235E/P331S triple mutation in the Fc region.

25. The antibody or antigen-binding fragment thereof of claim 1, wherein the antibody or antigen-binding fragment thereof comprises a variable heavy chain region comprising an amino acid sequence that is at least 95% identical to the amino acid sequence of SEQ ID NO: 24 and a variable light chain region comprising an amino acid sequence that is at least 95% identical to the amino acid sequence of SEQ ID NO: 30.

26. The antibody or antigen-binding fragment thereof of claim 1, wherein the antibody or antigen-binding fragment thereof comprises a variable heavy chain region comprising the amino acid sequence of SEQ ID NO: 24 and a variable light chain region comprising the amino acid sequence of SEQ ID NO: 30.

27. The antibody or antigen-binding fragment thereof of claim 1, wherein the antibody or antigen-binding fragment thereof comprises a heavy chain comprising the amino acid sequence of SEQ ID NO: 22 and a light chain comprising the amino acid sequence of SEQ ID NO: 28.

28. A pharmaceutical composition comprising an antibody or antigen-binding fragment thereof, according to claim 1, and a pharmaceutically acceptable excipient.

29. An isolated nucleic acid molecule encoding the antibody or antigen-binding fragment thereof, according to claim 1.

30. The isolated nucleic acid molecule of claim 29, wherein the nucleic acid molecule comprises a nucleotide sequence that is at least 90% identical to the nucleotide sequence of SEQ ID NO: 23.

31. The isolated nucleic acid molecule of claim 29, wherein the nucleic acid molecule comprises a nucleotide sequence that is at least 90% identical to the nucleotide sequence of SEQ ID NO: 29.

32. A host cell comprising a vector comprising the nucleic acid molecule of claim 29.

33. A method of treating an α-synucleinopathy in a patient, the method comprising administering to the patient an antibody or antigen-binding fragment thereof, according to claim 1.

34. The method according to claim 33, wherein the α-synucleinopathy is selected from Parkinson's disease (PD), dementia with Lewy bodies (DLB), and multiple system atrophy (MSA).

35. The method according to claim 34, wherein the α-synucleinopathy is Parkinson's disease (PD).

* * * * *

UNITED STATES PATENT AND TRADEMARK OFFICE
CERTIFICATE OF CORRECTION

| | | |
|---|---|---|
| PATENT NO. | : 11,560,424 B2 | Page 1 of 1 |
| APPLICATION NO. | : 17/111159 | |
| DATED | : January 24, 2023 | |
| INVENTOR(S) | : Schofield et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 217 days.

Signed and Sealed this
Thirty-first Day of December, 2024

Derrick Brent
*Acting Director of the United States Patent and Trademark Office*